(12) United States Patent
Jia et al.

(10) Patent No.: US 11,753,406 B2
(45) Date of Patent: Sep. 12, 2023

(54) SALTS OF A PD-1/PD-L1 INHIBITOR

(71) Applicant: Incyte Corporation, Wilmington, DE (US)

(72) Inventors: Zhongjiang Jia, Kennett Square, PA (US); Pingli Liu, Wilmington, DE (US); David J. Meloni, Bear, DE (US); Yongchun Pan, Wilmington, DE (US); Yongzhong Wu, Glen Mills, PA (US); Jiacheng Zhou, Newark, DE (US); Qun Li, Newark, DE (US)

(73) Assignee: Incyte Corporation, Wilmington, DE (US)

( * ) Notice: Subject to any disclaimer, the term of this patent is extended or adjusted under 35 U.S.C. 154(b) by 220 days.

(21) Appl. No.: 16/987,557

(22) Filed: Aug. 7, 2020

(65) Prior Publication Data

US 2021/0040090 A1 Feb. 11, 2021

Related U.S. Application Data

(60) Provisional application No. 62/884,996, filed on Aug. 9, 2019.

(51) Int. Cl.
*C07D 471/04* (2006.01)
*A61K 9/00* (2006.01)

(52) U.S. Cl.
CPC .......... *C07D 471/04* (2013.01); *A61K 9/0053* (2013.01); *C07B 2200/13* (2013.01)

(58) Field of Classification Search
None
See application file for complete search history.

(56) References Cited

U.S. PATENT DOCUMENTS

| 3,272,781 | A | 9/1966 | Goodrow |
| 4,208,328 | A | 6/1980 | Lavallee et al. |
| 4,789,711 | A | 12/1988 | Monnier et al. |
| 5,077,164 | A | 12/1991 | Ueda et al. |
| 6,114,497 | A | 9/2000 | Tada et al. |
| 6,297,351 | B1 | 10/2001 | Murayama et al. |
| 6,372,907 | B1 | 4/2002 | Lee et al. |
| 6,521,618 | B2 | 2/2003 | Boschelli et al. |
| 6,867,200 | B1 | 3/2005 | Allen et al. |
| 7,320,989 | B2 | 1/2008 | Anderson et al. |
| 7,417,065 | B2 | 8/2008 | Mi et al. |
| 7,491,245 | B2 | 2/2009 | Glenn et al. |
| 7,691,870 | B2 | 4/2010 | Buchstaller et al. |
| 7,851,489 | B2 | 12/2010 | Borzilleri et al. |
| 8,163,743 | B2 | 4/2012 | Baldwin et al. |
| 8,541,424 | B2 | 9/2013 | DeGoey et al. |
| 8,993,604 | B2 | 3/2015 | Byrd et al. |
| 9,085,576 | B2 | 7/2015 | Minatti et al. |
| 9,163,017 | B2 | 10/2015 | DeGoey et al. |
| 9,394,365 | B1 | 7/2016 | Eisenbach-Schwartz et al. |
| 9,540,322 | B2 | 1/2017 | Jorgensen et al. |
| 9,603,950 | B1 | 3/2017 | Li et al. |
| 9,611,261 | B2 | 4/2017 | Minatti et al. |
| 9,643,922 | B2 | 5/2017 | Jorgensen et al. |
| 10,017,520 | B2 | 7/2018 | Koehler et al. |
| 10,202,343 | B2 | 2/2019 | Jorgensen et al. |
| 10,308,644 | B2 | 6/2019 | Wu et al. |
| 10,618,916 | B2 | 4/2020 | Wu et al. |
| 10,669,271 | B2 | 6/2020 | Wu et al. |
| 10,793,505 | B2 | 10/2020 | Wu et al. |
| 10,793,565 | B2 | 10/2020 | Wu et al. |
| 10,800,768 | B2 | 10/2020 | Wu et al. |
| 10,806,785 | B2 | 10/2020 | Liu et al. |
| 10,906,920 | B2 | 2/2021 | Wu et al. |
| 11,124,511 | B2 | 9/2021 | Wu et al. |
| 11,339,149 | B2 | 5/2022 | Wu et al. |
| 11,401,279 | B2 | 8/2022 | Li et al. |
| 11,407,749 | B2 | 8/2022 | Wu et al. |
| 11,414,433 | B2 | 8/2022 | Wu et al. |
| 11,465,981 | B2 | 10/2022 | Wu et al. |
| 2002/0082266 | A1 | 6/2002 | Gallant et al. |
| 2003/0134843 | A1 | 7/2003 | Lubisch et al. |
| 2003/0191115 | A1 | 10/2003 | Pinto et al. |
| 2004/0018986 | A1 | 1/2004 | Pitlik et al. |
| 2004/0058938 | A1 | 3/2004 | Cullmann et al. |
| 2004/0063963 | A1 | 4/2004 | Ueno et al. |
| 2004/0082635 | A1 | 4/2004 | Hashimoto et al. |
| 2004/0186114 | A1 | 9/2004 | Cirillo et al. |
| 2004/0214040 | A1 | 10/2004 | Lee et al. |
| 2005/0187230 | A1 | 8/2005 | Ding et al. |
| 2005/0245536 | A1 | 11/2005 | Hao et al. |
| 2005/0260126 | A1 | 11/2005 | Kudo et al. |
| 2005/0288295 | A1 | 12/2005 | Currie et al. |
| 2006/0004010 | A1 | 1/2006 | Habashita et al. |
| 2006/0084650 | A1 | 4/2006 | Dong et al. |
| 2006/0089362 | A1 | 4/2006 | Seno et al. |
| 2006/0178367 | A1 | 8/2006 | Currie et al. |
| 2006/0183746 | A1 | 8/2006 | Currie et al. |
| 2006/0229337 | A1 | 10/2006 | Brittelli et al. |
| 2006/0270686 | A1 | 11/2006 | Kelly et al. |
| 2007/0099938 | A1 | 5/2007 | Ohmoto et al. |
| 2007/0191395 | A1 | 8/2007 | Kawakami et al. |
| 2008/0045536 | A1 | 2/2008 | Vaccaro et al. |
| 2008/0139557 | A1 | 6/2008 | Blomgren et al. |
| 2008/0153834 | A1 | 6/2008 | Blomgren et al. |
| 2008/0280891 | A1 | 11/2008 | Kelly et al. |

(Continued)

FOREIGN PATENT DOCUMENTS

| CA | 2355249 | 6/2000 |
| CA | 3099994 | 11/2019 |

(Continued)

OTHER PUBLICATIONS

Stahl et al., Handbook of Pharmaceutical Salts: Properties, Selection, and Use, (Wiley, 2002), p. 329-350.*

(Continued)

*Primary Examiner* — Po-Chih Chen
(74) *Attorney, Agent, or Firm* — Fish & Richardson P.C.

(57) ABSTRACT

The present invention relates to salt forms of the PD-1/PD-L1 inhibitor (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl) pyrrolidine-3-carboxylic acid, including methods of preparation thereof, where the compound is useful in the treatment of various diseases including infectious diseases and cancer.

23 Claims, 14 Drawing Sheets

(56) References Cited

U.S. PATENT DOCUMENTS

| | | |
|---|---|---|
| 2009/0163545 A1 | 6/2009 | Goldfarb |
| 2009/0253735 A1 | 10/2009 | Almario-Garcia et al. |
| 2009/0281075 A1 | 11/2009 | Roughton et al. |
| 2009/0281120 A1 | 11/2009 | Nakai et al. |
| 2009/0304821 A1 | 12/2009 | Notoya et al. |
| 2010/0155712 A1 | 6/2010 | Kitamura |
| 2010/0160292 A1 | 6/2010 | Whitney et al. |
| 2010/0160303 A1 | 6/2010 | Liu et al. |
| 2010/0249151 A1 | 9/2010 | Klein et al. |
| 2010/0267775 A1 | 10/2010 | Negoro et al. |
| 2010/0267778 A1 | 10/2010 | Kusuda et al. |
| 2010/0273832 A1 | 10/2010 | Jung et al. |
| 2010/0292227 A1 | 11/2010 | Yoakim et al. |
| 2011/0053915 A1 | 3/2011 | Ivaschenko et al. |
| 2011/0062858 A1 | 3/2011 | Yersin et al. |
| 2011/0065699 A1 | 3/2011 | De Peretti et al. |
| 2011/0065700 A1 | 3/2011 | De Peretti et al. |
| 2011/0065745 A1 | 3/2011 | De Peretti et al. |
| 2011/0124640 A1 | 5/2011 | Liu et al. |
| 2011/0294781 A1 | 12/2011 | Yamamoto et al. |
| 2011/0301145 A1 | 12/2011 | Barbosa, Jr. et al. |
| 2012/0058996 A1 | 3/2012 | Liu et al. |
| 2012/0295884 A1 | 11/2012 | Altmann et al. |
| 2012/0323002 A1 | 12/2012 | Yamamoto et al. |
| 2012/0328569 A1 | 12/2012 | McComas et al. |
| 2013/0096118 A1 | 4/2013 | Liu et al. |
| 2013/0131063 A1 | 5/2013 | Castro et al. |
| 2013/0203741 A1 | 8/2013 | Suzuki et al. |
| 2013/0203747 A1 | 8/2013 | Yoakim et al. |
| 2013/0203754 A1 | 8/2013 | Yang et al. |
| 2013/0253011 A1 | 9/2013 | Jung et al. |
| 2014/0058097 A1 | 2/2014 | Kobayashi et al. |
| 2014/0088117 A1 | 3/2014 | Burch et al. |
| 2014/0128382 A1 | 5/2014 | Wu et al. |
| 2014/0243306 A1 | 8/2014 | Heng et al. |
| 2014/0275058 A1 | 9/2014 | Minatti et al. |
| 2014/0288094 A1 | 9/2014 | Bennett et al. |
| 2014/0378447 A1 | 12/2014 | Okano et al. |
| 2015/0005279 A1 | 1/2015 | Bonafoux et al. |
| 2015/0011751 A1 | 1/2015 | Kawakami et al. |
| 2015/0073024 A1 | 3/2015 | Sasikumar et al. |
| 2015/0181880 A1 | 7/2015 | Takahashi |
| 2015/0210680 A1 | 7/2015 | Kobayashi et al. |
| 2015/0232478 A1 | 8/2015 | Ishida et al. |
| 2015/0239868 A1 | 8/2015 | Pais et al. |
| 2015/0252011 A1 | 9/2015 | Minatti et al. |
| 2015/0258505 A1 | 9/2015 | Hironaka et al. |
| 2015/0291549 A1 | 10/2015 | Chupak et al. |
| 2015/0299227 A1 | 10/2015 | Wolkenberg et al. |
| 2015/0307465 A1 | 10/2015 | Scott et al. |
| 2015/0376172 A1 | 12/2015 | Guba et al. |
| 2016/0015690 A1 | 1/2016 | Babaoglu et al. |
| 2016/0046648 A1 | 2/2016 | Petrukhin et al. |
| 2016/0130251 A1 | 5/2016 | Graupe et al. |
| 2016/0194295 A1 | 7/2016 | Sasikumar et al. |
| 2016/0229816 A1 | 8/2016 | Sato et al. |
| 2016/0280695 A1 | 9/2016 | Minatti et al. |
| 2017/0107216 A1 | 4/2017 | Wu et al. |
| 2017/0145025 A1 | 5/2017 | Li et al. |
| 2017/0174671 A1 | 6/2017 | Wu et al. |
| 2017/0174679 A1 | 6/2017 | Lajkiewicz et al. |
| 2017/0304282 A1 | 10/2017 | Rocco et al. |
| 2017/0320875 A1 | 11/2017 | Li et al. |
| 2017/0342060 A1 | 11/2017 | Lu et al. |
| 2017/0362253 A1 | 12/2017 | Xiao et al. |
| 2018/0016260 A1 | 1/2018 | Yu et al. |
| 2018/0057486 A1 | 3/2018 | Wu et al. |
| 2018/0177784 A1 | 6/2018 | Wu et al. |
| 2018/0177870 A1 | 6/2018 | Liu et al. |
| 2018/0179179 A1 | 6/2018 | Wu et al. |
| 2018/0179197 A1 | 6/2018 | Wu et al. |
| 2018/0179201 A1 | 6/2018 | Wu et al. |
| 2018/0179202 A1 | 6/2018 | Wu et al. |
| 2018/0273519 A1 | 9/2018 | Wu et al. |
| 2019/0040082 A1 | 2/2019 | Xiao et al. |
| 2019/0062345 A1 | 2/2019 | Xiao et al. |
| 2019/0071439 A1 | 3/2019 | Li et al. |
| 2019/0144439 A1 | 5/2019 | Wu et al. |
| 2019/0202824 A1 | 7/2019 | Wu et al. |
| 2019/0225601 A1 | 7/2019 | Wu et al. |
| 2019/0270706 A1 | 9/2019 | Jorgensen et al. |
| 2019/0300524 A1 | 10/2019 | Wu et al. |
| 2019/0345170 A1 | 11/2019 | Wu et al. |
| 2020/0172533 A1 | 6/2020 | Wu et al. |
| 2020/0172541 A1 | 6/2020 | Li et al. |
| 2020/0181126 A1 | 6/2020 | Lu et al. |
| 2020/0255424 A1 | 8/2020 | Wu et al. |
| 2020/0277309 A1 | 9/2020 | Wu et al. |
| 2020/0283423 A1 | 9/2020 | Yu et al. |
| 2020/0325115 A1 | 10/2020 | Wu et al. |
| 2020/0397893 A1 | 12/2020 | Liu et al. |
| 2020/0407357 A1 | 12/2020 | Lajkiewicz et al. |
| 2021/0002276 A1 | 1/2021 | Wu et al. |
| 2021/0017164 A1 | 1/2021 | Lu et al. |
| 2021/0017175 A1 | 1/2021 | Li et al. |
| 2021/0094976 A1 | 4/2021 | Li et al. |
| 2021/0107900 A1 | 4/2021 | Wu et al. |
| 2021/0115025 A1 | 4/2021 | Yu et al. |
| 2021/0115068 A1 | 4/2021 | Wu et al. |
| 2021/0139511 A1 | 5/2021 | Jia et al. |
| 2021/0221819 A1 | 7/2021 | Li et al. |
| 2021/0317139 A1 | 10/2021 | Xiao et al. |
| 2021/0347771 A1 | 11/2021 | Wu et al. |
| 2021/0363137 A1 | 11/2021 | Wu et al. |
| 2021/0380584 A1 | 12/2021 | Wu et al. |
| 2022/0089588 A1 | 3/2022 | Wu et al. |
| 2022/0144830 A1 | 5/2022 | Zhou et al. |
| 2022/0144831 A1 | 5/2022 | Wang et al. |
| 2022/0144832 A1 | 5/2022 | Jia et al. |
| 2022/0193050 A1 | 6/2022 | Yang et al. |
| 2022/0194931 A1 | 6/2022 | Wu et al. |
| 2022/0213090 A1 | 7/2022 | Wu et al. |
| 2022/0340600 A1 | 10/2022 | Li et al. |
| 2022/0348594 A1 | 11/2022 | Wu et al. |

FOREIGN PATENT DOCUMENTS

| | | |
|---|---|---|
| CL | 2018001531 | 7/2018 |
| CL | 2018003734 | 2/2019 |
| CL | 2018003701 | 4/2019 |
| CL | 2018003697 | 5/2019 |
| CL | 2019001744 | 10/2019 |
| CL | 2020002511 | 9/2020 |
| CN | 1344256 | 4/2002 |
| CN | 101891895 | 11/2010 |
| CN | 101910158 | 12/2010 |
| CN | 101993415 | 3/2011 |
| CN | 103933036 | 7/2014 |
| CN | 104045552 | 9/2014 |
| CN | 104211726 | 12/2014 |
| CN | 105164121 | 12/2015 |
| CN | 105705489 | 6/2016 |
| EP | 0361069 | 4/1990 |
| EP | 0644460 | 3/1995 |
| EP | 1505068 | 2/2005 |
| EP | 1644370 | 4/2006 |
| EP | 1942105 | 7/2008 |
| EP | 2233474 | 9/2010 |
| EP | 2402345 | 1/2012 |
| EP | 2871179 | 5/2015 |
| EP | 2824099 | 1/2018 |
| FR | 1425700 | 1/1966 |
| JP | H 10316853 | 12/1998 |
| JP | 2000128986 | 5/2000 |
| JP | 2000128987 | 5/2000 |
| JP | 2000212281 | 8/2000 |
| JP | 2001114893 | 4/2001 |
| JP | 2001163975 | 6/2001 |
| JP | 3461397 | 10/2003 |
| JP | 2003287634 | 10/2003 |
| JP | 2004059761 | 2/2004 |
| JP | 2004091369 | 3/2004 |
| JP | 2004294556 | 10/2004 |
| JP | 2005002330 | 1/2005 |

(56) References Cited

FOREIGN PATENT DOCUMENTS

| | | |
|---|---|---|
| JP | 2005248082 | 9/2005 |
| JP | 2005290301 | 10/2005 |
| JP | 2006-290883 A | 10/2006 |
| JP | 2008218327 | 9/2008 |
| JP | 2010202530 | 9/2010 |
| JP | 2010540452 | 12/2010 |
| JP | 2013084945 | 5/2013 |
| JP | 2014520866 | 8/2014 |
| JP | 2014532066 | 12/2014 |
| JP | 2015155397 | 8/2015 |
| JP | 2015193612 | 11/2015 |
| JP | 2016135778 | 7/2016 |
| JP | 2016532710 | 10/2016 |
| JP | 2019523231 | 8/2019 |
| JP | 2019530732 | 10/2019 |
| JP | 2020504737 | 2/2020 |
| JP | 2020504739 | 2/2020 |
| JP | 2020514271 | 5/2020 |
| JP | 6911031 | 7/2021 |
| KR | 1715090 | 3/2015 |
| KR | 1717601 | 12/2015 |
| KR | 1653560 | 2/2016 |
| TW | 103143948 | 12/2014 |
| TW | 201625527 | 7/2016 |
| WO | WO 98/27108 | 6/1998 |
| WO | WO 1999/018096 | 4/1999 |
| WO | WO 99/44992 A1 | 9/1999 |
| WO | WO 00/35886 | 6/2000 |
| WO | WO 01/07409 | 2/2001 |
| WO | WO 2001/047883 | 7/2001 |
| WO | WO 01/74815 | 10/2001 |
| WO | WO 2002/000196 | 1/2002 |
| WO | WO 02/14321 | 2/2002 |
| WO | WO 02/48147 | 6/2002 |
| WO | WO 02/066477 | 8/2002 |
| WO | WO 02/071827 | 9/2002 |
| WO | WO 02/078700 | 10/2002 |
| WO | WO 02/083672 | 10/2002 |
| WO | WO 02/088124 | 11/2002 |
| WO | WO 03/022845 | 3/2003 |
| WO | WO 03/030901 | 4/2003 |
| WO | WO 03/031587 | 4/2003 |
| WO | WO 2004/006906 | 1/2004 |
| WO | WO 2004/033454 | 4/2004 |
| WO | WO 2004/035588 | 4/2004 |
| WO | WO 2004/085385 | 10/2004 |
| WO | WO 2004/089940 | 10/2004 |
| WO | WO 2005/000833 | 1/2005 |
| WO | WO 2005/005429 | 1/2005 |
| WO | WO 2005/014543 | 2/2005 |
| WO | WO 2005/014599 | 2/2005 |
| WO | WO 2005/023761 | 3/2005 |
| WO | WO 2005/034869 | 4/2005 |
| WO | WO 2005/047290 | 5/2005 |
| WO | WO 2005/063710 | 7/2005 |
| WO | WO 2005/077948 | 8/2005 |
| WO | WO 2005/079802 | 9/2005 |
| WO | WO 2005/080316 | 9/2005 |
| WO | WO 2005/086808 | 9/2005 |
| WO | WO 2005/086904 | 9/2005 |
| WO | WO 2005/097751 | 10/2005 |
| WO | WO 2005/103022 | 11/2005 |
| WO | WO 2005/105798 | 11/2005 |
| WO | WO 2006/034317 | 3/2006 |
| WO | WO 2006/034337 | 3/2006 |
| WO | WO 2006/050803 | 5/2006 |
| WO | WO 2006/053121 | 5/2006 |
| WO | WO 2006/094235 | 9/2006 |
| WO | WO 2006/099075 | 9/2006 |
| WO | WO 2006/125101 | 11/2006 |
| WO | WO 2007/004954 | 1/2007 |
| WO | WO 2007/034282 | 3/2007 |
| WO | WO 2007/038314 | 4/2007 |
| WO | WO 2007/061764 | 5/2007 |
| WO | WO 2007/067711 | 6/2007 |
| WO | WO 2007/069565 | 6/2007 |
| WO | WO 2007/096764 | 8/2007 |
| WO | WO 2007/113226 | 10/2007 |
| WO | WO 2007/146712 | 12/2007 |
| WO | WO 2008/011560 | 1/2008 |
| WO | WO 2008/021745 | 2/2008 |
| WO | WO 2008/027812 | 3/2008 |
| WO | WO 2008/032171 | 3/2008 |
| WO | WO 2008/033854 | 3/2008 |
| WO | WO 2008/033857 | 3/2008 |
| WO | WO 2008/033858 | 3/2008 |
| WO | WO 2008/057254 | 5/2008 |
| WO | WO 2008/062182 | 5/2008 |
| WO | WO 2008/064317 | 5/2008 |
| WO | WO 2008/064318 | 5/2008 |
| WO | WO 2008/071944 | 6/2008 |
| WO | WO 2008/079965 | 7/2008 |
| WO | WO 2008/104077 | 9/2008 |
| WO | WO 2008/104278 | 9/2008 |
| WO | WO 2008/104279 | 9/2008 |
| WO | WO 2008/111299 | 9/2008 |
| WO | WO 2008/114002 | 9/2008 |
| WO | WO 2008/118122 | 10/2008 |
| WO | WO 2008/133274 | 11/2008 |
| WO | WO 2008/134553 | 11/2008 |
| WO | WO 2008/141249 | 11/2008 |
| WO | WO 2009/027733 | 3/2009 |
| WO | WO 2009/038759 | 3/2009 |
| WO | WO 2009/039397 | 3/2009 |
| WO | WO 2009/059162 | 5/2009 |
| WO | WO 2009/062059 | 5/2009 |
| WO | WO 2009/075830 | 6/2009 |
| WO | WO 2009/077197 | 6/2009 |
| WO | WO 2009/079683 | 7/2009 |
| WO | WO 2009/106539 | 9/2009 |
| WO | WO 2009/106597 | 9/2009 |
| WO | WO 2009/123986 | 10/2009 |
| WO | WO 2009/139576 | 11/2009 |
| WO | WO 2009/143156 | 11/2009 |
| WO | WO 2009/146358 | 12/2009 |
| WO | WO 2010/011837 | 1/2010 |
| WO | WO 2010/029950 | 3/2010 |
| WO | WO 2010/056875 | 5/2010 |
| WO | WO 2010/064020 | 6/2010 |
| WO | WO 2010/071885 | 6/2010 |
| WO | WO 2010/075376 | 7/2010 |
| WO | WO 2010/080474 | 7/2010 |
| WO | WO 2010/104306 | 9/2010 |
| WO | WO 2010/115736 | 10/2010 |
| WO | WO 2010/119264 | 10/2010 |
| WO | WO 2010/130034 | 11/2010 |
| WO | WO 2011/002635 | 1/2011 |
| WO | WO 2011/008709 | 1/2011 |
| WO | WO 2011/018170 | 2/2011 |
| WO | WO 2011/044181 | 4/2011 |
| WO | WO 2011/047129 | 4/2011 |
| WO | WO 2011/047319 | 4/2011 |
| WO | WO 2011/050245 | 4/2011 |
| WO | WO 2009/096202 | 5/2011 |
| WO | WO 2011/082400 | 7/2011 |
| WO | WO 2011/097607 | 8/2011 |
| WO | WO 2011/113606 | 9/2011 |
| WO | WO 2011/117264 | 9/2011 |
| WO | WO 2011/140202 | 11/2011 |
| WO | WO 2012/016133 | 2/2012 |
| WO | WO 2012/033735 | 3/2012 |
| WO | WO 2012/034363 | 3/2012 |
| WO | WO 2012/047856 | 4/2012 |
| WO | WO 2012/052730 | 4/2012 |
| WO | WO 2012/052745 | 4/2012 |
| WO | WO 2012/068406 | 5/2012 |
| WO | WO 2012/080376 | 6/2012 |
| WO | WO 2012/088411 | 6/2012 |
| WO | WO 2012/100342 | 8/2012 |
| WO | WO 2012/125886 | 9/2012 |
| WO | WO 2012/129562 | 9/2012 |
| WO | WO 2012/139425 | 10/2012 |
| WO | WO 2012/159565 | 11/2012 |
| WO | WO 2012/166951 | 12/2012 |

(56) References Cited

FOREIGN PATENT DOCUMENTS

| | | |
|---|---|---|
| WO | WO 2012/168733 | 12/2012 |
| WO | WO 2012/175991 | 12/2012 |
| WO | WO 2013/008095 | 1/2013 |
| WO | WO 2013/033901 | 3/2013 |
| WO | WO 2013/040528 | 3/2013 |
| WO | WO 2013/057650 | 4/2013 |
| WO | WO 2013/059594 | 4/2013 |
| WO | WO 2013/120040 | 8/2013 |
| WO | WO 2013/134113 | 9/2013 |
| WO | WO 2013/157021 | 10/2013 |
| WO | WO 2013/163404 | 10/2013 |
| WO | WO 2014/009295 | 1/2014 |
| WO | WO 2014/009296 | 1/2014 |
| WO | WO 2014/017087 | 1/2014 |
| WO | WO 2014/039595 | 3/2014 |
| WO | WO 2014/061693 | 4/2014 |
| WO | WO 2014/081878 | 5/2014 |
| WO | WO 2014/113388 | 7/2014 |
| WO | WO 2014/114532 | 7/2014 |
| WO | WO 2014/121085 | 8/2014 |
| WO | WO 2014/133046 | 9/2014 |
| WO | WO 2014/138484 | 9/2014 |
| WO | WO 2014/138791 | 9/2014 |
| WO | WO 2014/151634 | 9/2014 |
| WO | WO 2014/152536 | 9/2014 |
| WO | WO 2014/159959 | 10/2014 |
| WO | WO 2014/181287 | 11/2014 |
| WO | WO 2014/186035 | 11/2014 |
| WO | WO 2014/210255 | 12/2014 |
| WO | WO 2015/000715 | 1/2015 |
| WO | WO 2015/013635 | 1/2015 |
| WO | WO 2015/018940 | 2/2015 |
| WO | WO 2015/033299 | 3/2015 |
| WO | WO 2015/033301 | 3/2015 |
| WO | WO 2015/034820 | 3/2015 |
| WO | WO 2015/036927 | 3/2015 |
| WO | WO 2015/086498 | 6/2015 |
| WO | WO 2015/086499 | 6/2015 |
| WO | WO 2015/086502 | 6/2015 |
| WO | WO 2015/086512 | 6/2015 |
| WO | WO 2015/095337 | 6/2015 |
| WO | WO 2015/101622 | 7/2015 |
| WO | WO 2015/120364 | 8/2015 |
| WO | WO 2015/150097 | 10/2015 |
| WO | WO 2015/160641 | 10/2015 |
| WO | WO 2015/197028 | 12/2015 |
| WO | WO 2016/044604 | 3/2016 |
| WO | WO 2016/094688 | 6/2016 |
| WO | WO 2016/116525 | 7/2016 |
| WO | WO 2016/118404 | 7/2016 |
| WO | WO 2016/156282 | 10/2016 |
| WO | WO 2017/035405 | 3/2017 |
| WO | WO 2017/066227 | 4/2017 |
| WO | WO 2017/070089 | 4/2017 |
| WO | WO 2017/070320 | 4/2017 |
| WO | WO 2017/087777 | 5/2017 |
| WO | WO 2017/106634 | 6/2017 |
| WO | WO 2017/108569 | 6/2017 |
| WO | WO 2017/109041 | 6/2017 |
| WO | WO 2017/112617 | 6/2017 |
| WO | WO 2017/112730 | 6/2017 |
| WO | WO 2017/192961 | 11/2017 |
| WO | WO 2017/205464 | 11/2017 |
| WO | WO 2017/222976 | 12/2017 |
| WO | WO 2017/223239 | 12/2017 |
| WO | WO 2018/013789 | 1/2018 |
| WO | WO 2018/026971 | 2/2018 |
| WO | WO 2018/044783 | 3/2018 |
| WO | WO 2018/045084 | 3/2018 |
| WO | WO 2016/057500 | 4/2018 |
| WO | WO 2018/116259 | 6/2018 |
| WO | WO 2018/119036 | 6/2018 |
| WO | WO 2018/119221 | 6/2018 |
| WO | WO 2018/119224 | 6/2018 |
| WO | WO 2018/119236 | 6/2018 |
| WO | WO 2018/119263 | 6/2018 |
| WO | WO 2018/119266 | 6/2018 |
| WO | WO 2018/119286 | 6/2018 |
| WO | WO 2018/195321 | 10/2018 |
| WO | WO 2019/023575 | 1/2019 |
| WO | WO 2019/032547 | 2/2019 |
| WO | WO 2019/034172 | 2/2019 |
| WO | WO 2019/191707 | 10/2019 |
| WO | WO 2019/192506 | 10/2019 |
| WO | WO 2019/204609 | 10/2019 |
| WO | WO 2020/086556 | 4/2020 |
| WO | WO 2020/088357 | 5/2020 |
| WO | WO 2020/156323 | 8/2020 |
| WO | WO 2021/030162 | 2/2021 |

OTHER PUBLICATIONS

Alverez et al., "Structure-Activity Study of Bioisosteric Trifluoromethyl and Pentafluorosulfanyl Indole Inhibitors of the AAA ATPase p97," ACS Med Chem., 2015, 6(12):1225-1230.
Brazilian Office Action in Brazilian Application No. BR112018012756-6, dated Jan. 5, 2021, 6 pages.
Chinese Office Action in Chinese Application No. 201680077700.8, dated Jul. 2, 2021, 23 pages.
Chinese Search Report in Chinese Application No. 201780049752.9, dated Dec. 28, 2020, 5 pages.
European Communication in European Application No. 16805690.1, dated Nov. 5, 2020, 4 pages.
Gould et al. "Salt selection for basic drugs," Int J Pharma., 1986, 33(1-3):201-217.
Indian Office Action with Indian Application No. 201917001998, dated Nov. 24, 2020, 7 pages.
Indian Office Action with Indian Application No. 201917028273, dated Feb. 15, 2021, 5 pages.
International Preliminary Report on Patentability in International Application No. PCT/US2019/031728, dated Nov. 17, 2020, 7 pages.
International Search Report and Written Opinion in International Application No. PCT/US2020/059817, dated Mar. 29, 2021, 19 pages.
International Search Report in International Application No. PCT/US2020/053190, dated Jan. 29, 2021, 13 pages.
Japanese Office Action in Japanese Application No. 2019-534122, dated Oct. 19, 2021, 10 pages.
Japanese Office Action in Japanese Application No. 2019-534195, dated Nov. 1, 2021, 9 pages.
Japanese Office Action in Japanese Application No. 2019-534196, dated Nov. 9, 2021, 9 pages.
Mexican Office Action in Mexican Application No. MX/a/2018/007774, dated Apr. 8, 2021, 5 pages.
Mexican Office Action in Mexican Application No. MX/a/2018/016273, dated Mar. 26, 2021, 5 pages.
Miyaura and Suzuki, "Palladium-Catalyzed Cross-Coupling Reactions of Organoboron Compounds," Chem Rev., 1995, 95:2457-2483.
Qin et al., "The Diverse Function of PD-1/PD-L Pathway Beyond Cancer," Frontiers In Imunology, Oct. 2019, 10(2298):1-16.
Sun et al., "Studies on Synthesis and Properties of Some New Dibenzocyclobromonium," Chemical Journal of Chinese Universities, 1998, 19(12), 6 pages (English Abstract).
Taiwan Office Action in Taiwan Application No. 105133530, dated Oct. 15, 2020, 8 pages.
Taiwan Office Action in Taiwan Application No. 105137807, dated Nov. 12, 2020, 12 pages.
Taiwan Office Action in Taiwan Application No. 105141804, dated Nov. 9, 2020, 9 pages.
Ukraine Office Action in Ukraine Application No. a 2019 00525, dated Jan. 14, 2021, 11 pages.
Wuts et al., "Protective Groups in Organic Synthesis," 4th Ed., 2007, 1111 pages.
Abdellaoui et al., "Palladium-catalyzed non-directed C—H bond arylation of difluorobenzenes and dichlorobenzenes bearing benzoxazole or benzothiazole," Catalysis Communications, 2015, 71:13-16.

(56) References Cited

OTHER PUBLICATIONS

Ahmed et al., "Enantioselective Polymerization of Epoxides Using Biaryl-Linked Bimetallic Cobalt Catalysts: A Mechanistic Study," J Am Chem Soc., 2013, 135(50):18901-18911.
Amaya et al., "Synthesis of three-dimensionally arranged bis-biphenol ligand on hexaaryl benzene scaffold and its application for cross-pinacol coupling reaction," Tetrahedron Letters, 2011, 52(35):4567-4569.
Anyika et al., "Point-to-Axial Chirality Transfer-A New Probe for "Sensing" the Absolute Configurations of Monoamines," J Am Chem Soc., 2014, 136(2):550-553.
Arkin et al., "Small-Molecule Inhibitors of Protein-Protein Interactions: Progressing toward the Reality," Chemistry & Biology, Sep. 2014, 21:1102-1114.
Arkin et al., "Small-Molecule Inhibitors of Protein-Protein Interactions: Progressing Towards the Dream," Nature Reviews, Apr. 2004, 3:301-317.
Artz et al., "Host-guest complexation. 28. Hemispherands with four self-organizing units," J Am Chem Soc., 1984, 106(7):2160-2171.
Atzrodt et al., "The Renaissance of H/D Exchange," Angew Chem Int Ed., 2007, 7744-7765.
Australian Office Action in Australian Application No. 2016358100, dated May 8, 2020, 5 pages.
Barakat, "Do We Need Small Molecule Inhibitors for the Immune Checkpoints?" J. Pharma. Care Health Sys., 2014, 1(4):10000e119.
Barber et al, "Restoring function in exhausted CD8 T cells during chronic viral infection," Nature, Feb. 2006, 439:682-687.
Bentley et al., "Antenna Biphenols: Development of Extended Wavelength Chiroptical Reporters," J Org Chem., 2016, 81(3):1185-1191.
Berg, "Modulation of Protein-Protein Interactions with Small Organic Molecules," Angew. Chem. Int. Ed., 2003, 42:2462-2481.
Berge et al., "Pharmaceutical Salts," J. Pharm. Sci., Jan. 1977, 66(1):1-19.
Blank et al, "PD-L1/B7H-1 Inhibits the Effector Phase of Tumor Rejection by T Cell Receptor (TCR) Transgenic CD8+ T Cells," Cancer Res., Feb. 2004, 64(3):1140-5.
Blom et al., "Optimizing Preparative LC-MS Configurations and Methods for Parallel Synthesis Purification", J. Combi. Chem., 2003, 5:670-83.
Blom et al., "Preparative LC-MS Purification: Improved Compound Specific Method Optimization", J. Combi. Chem., Nov. 2004, 6:874-883.
Blom, "Two-Pump At Column Dilution Configuration for Preparative LC-MS", K. Blom, J. Combi. Chem., 2002, 4:295-301.
Bross et al., "Radiation damage to 2-(2'-hydroxyphenyl)benzothiazoles," Radiation Physics and Chemistly, Jul. 1992, 41:379-387.
Buisman et al., "Chiral Cooperativity in Diastereomeric Diphosphite Ligands: Effects on the Rhodium-Catalyzed Enantioselective Hydroformylation of Styrene," Organometallics, 1997, 16(13):2929-2939.
Carter et al, "PD-1:PD-L inhibitory pathway affects both CD4+ and CD8+ T cells and is overcome by IL-2," Eur. J. Immunol., 2002, 32(3):634-643.
Chang et al., "Blocking of the PD-1/PD-L1 Interaction by a d-Peptide Antagonist for Cancer Immunotherapy," Angew. Chem. Int. Ed., 2015, 127(40):11926-11930.
Chang et al., "Blocking of the PD-1/PD-L1 Interaction by a d-Peptide Antagonist for Cancer Immunotherapy" Angew. Chem. Int. Ed., 2015, 26 pages; Supporting Information for 127(40):11926-11930.
Chen et al., "Anti-PD-1/PD-L1 therapy of human cancer: past, present, and future," J. Clin. Invest, Sep. 2015, 125(9):3384-3391.
Cheng et al., "Synthetic connections to the aromatic directed metalation reaction. Iterative ortho metalation-cross coupling tactics for the construction of polyphenyls," Tetrahedron Letters, 1978, 28(43):5097-5098.
Cheng et al., "Recent Advances in Small Molecule Based Cancer Immunotherapy," Eur J Med Chem., 2018, 157:582-598.
Cheng et al., "Structure and Interactions of the Human Programmed Cell Death 1 Receptor," J. Bio. Chem., Apr. 2013, 288(17):11771-11785.
Chilean Office Action in Chilean Application No. 201801685, dated Aug. 20, 2019, 18 pages.
Chilean Office Action in Chilean Application No. 201803701, dated Nov. 22, 2019, 18 page.
Chilean Office Action in Chilean Application No. 201901744, dated Apr. 14, 2020, 19 pages.
Clayden et al., "Conformational Preference and Remote (1,10) Stereocontrol in Biphenyl-2,2'-dicarboxamides," Org. Lett, 2001, 3(26):4133-4136.
Colombian Office Action in Colombian Application No. NC2019/0000386, dated Sep. 25, 2020, 18 pages.
Cram et al., "Host-guest complexation. 32. Spherands composed of cyclic urea and anisyl units," J Am Chem Soc., 1984, 106(23):7150-7167.
Cram et al., "Host-guest complexation. 29. Expanded hemispherands," J Am Chem Soc., 1984, 106(11):6386-3292.
Cram et al., "Host-guest complexation. 26. Cavitands composed of fluorobenzene units bonded in their 2,6-positions to form macrocycles," J Am Chem Soc., 1984, 106(3):695-701.
Cram et al., "Spherand hosts containing cyclic urea units," J Am Chem Soc., 1982, 104(24):6828-6830.
Curis, "Overview and Path for Growth," Aurigene Strategic Collaboration, Jan. 21, 2015, 13 slides.
Database Accession No. 1590700-72-3 abstract, Apr. 27, 2014, 1 page.
Database Accession No. 1581556-71-9 abstract, Apr. 8, 2014, 1 page.
Database Accession No. 1580823-55-7 abstract, Apr. 6, 2014, 1 page.
Database Accession No. 1568738-04-4 abstract, Mar. 14, 2014, 1 page.
Database accession No. 1478989-52-4 abstract, Nov. 22, 2013, 1 page.
Database accession No. 2013:447446 abstract, 2013, 1 page.
De Lucca et al., "Small Molecule Reversible Inhibitors of Bruton's Tyrosine Kinase (BTK): Structure-Activity Relationships Leading to the Identification of 7-(2-Hydroxypropan-2-yl)-4-[2-methyl-3-(4-oxo-3,4-dihydroquinazolin-3-yl)phenyl]-9H-carbazole-1-carboxamide (BMS-935177)," Journal of Medicinal Chemistiy, 2016, 59(17):7915-7935.
Differding, "AUNP-12—A Novel Peptide Therapeutic Targeting PD-1 Immune Checkpoint Pathway for Cancer Immunotherapy—Structure Activity Relationships & Peptide / Peptidomimetic Analogs," Differding Consulting s.p.r.l. (Belgium), Feb. 26, 2014, 12 pages.
Dhanunjayarao et al., "Synthesis and Optical Properties of Salicylaldimine-Based Diboron Complexes," Eur J Inorg Chem., 2014, 3:539-545.
Dolan et al., "PD-1 Pathway Inhibitors: Changing the Landscape of Cancer Immunotherapy," Cancer Control, Jul. 2014, 21(3):231-237.
Domling et al., "Programmed Death-1: Therapeutic Success after More than 100 Years of Cancer Immunotherapy," Angew. Chem. Int. Ed., 2014, 53:2283-2288.
Ecuador Opposition in Ecuador Application No. SENADI-2019-3773, dated Oct. 10, 2019, 29 pages.
Escarcega-Bobadilla et al., "A Recyclable Trinuclear Bifunctional Catalyst Derived from a Tetraoxo Bis-Zn(salphen) Metalloligand," Chemistry—A European Journal., 2013, 19(8):2641-2648.
Escarcega-Bobadilla et al., "Metal-directed assembly of chiral bis-Zn(II) Schiff base structures," Dalton Transactions, 2012, 41(32):9766-9772.
Escarcega-Bobadilla et al., "Versatile Switching in Substrate Topicity: Supramolecular Chirality Induction in Di- and Trinuclear Host Complexes," Chemistry—A European Journal, 2012:8(22):6805-6810.
Eurasian Office Action in Eurasian Application No. 201990074/28, dated Oct. 3, 2019, 5 pages.
European Communication in European Application No. 16805690.1, dated Jul. 10, 2018, 6 pages.

(56) References Cited

OTHER PUBLICATIONS

European Communication in European Application No. 16805690.1, dated Jan. 22, 2020, 5 pages.

European Communication in European Application No. 17743174.9, dated Jan. 31, 2020, 5 pages.

Fabris et al., "Central to Axial Transfer of Chirality in Menthone or Camphor-Derived 2,2'-Biphenols," J Org Chem., 1997, 62(21):7156-7164.

FDA Report, "22 Case Studies Where Phase 2 and Phase 3 Trials Had Divergent Results," U.S. Food and Drug Administration, Jan. 2017, 44 pages.

Francisco et al., "The PD-1 Pathway in Tolerance and Autoimmunity," Immunol. Rev., Jul. 2010, 236:219-242.

Freeman et al, "Engagement of the Pd-1 Immunoinhibitory Receptor by a Novel B7 Family Member Leads to Negative Regulation of Lymphocyte Activation," J. Exp. Med., Oct. 2000, 192(7):1027-34.

Freeman, "Structures of PD-1 with its ligands: Sideways and dancing cheek to cheek," PNAS, Jul. 2008, 105(30):10275-10276.

Freindorf, M., "Vibronic couplings in an excited state of hydrogen bond dimeric systems," Acta Physica Polonica, 1990, A78(6):825-839.

Gong et al., "Rhodium(I)-catalyzed regiospecific dimerization of aromatic acids: two direct C—H bond activations in water," Angewandte Chemie, 2015, 54(19):5718-5721.

Goswami et al., "A turn on ESIPT probe for rapid and ratiometric fluorogenic detection of homocysteine and cysteine in water with live cell-imaging," Tetrahedron Letters, 2014, 55(2):490-494.

Green et al., "Synthesis and investigation of the configurational stability of some dimethylammonium borate salts," J. Chem. Soc., Perkin Trans. 1, 2000, 24:4403-4408.

Greenwald et al, "The B7 Family Revisited," Annu. Rev. Immunol., 2005, 23:515-548.

Han et al., "Synthesis of binuclear phenoxyimino organoaluminum complexes and their use as the catalyst precursors for efficient ring-opening polymerisation of E-caprolactone," Dalton Transactions, 2013, 41:12346-12353.

Helgeson et al., "Host-guest complexation. 66. 18-Membered-ring spherands containing five anisyl groups," J Am Chem Soc., 1993, 1115(24):11506-11511.

Hilfiker "Relevance of Solid-state Properties for Pharmaceutical Products," Polymorphism in the Pharmaceutical Industry, Jan. 1, 2006, pp. 1-19.

Hu et al., "Syntheses and Ethylene Polymerization Behavior of Supported Salicylaldimine-Based Neutral Nickel(II) Catalysts," Organometallics, 2007, 26(10):2609-2615.

Hu et al., "Synthesis and Ethylene Polymerization Activity of a Novel, Highly Active Single-Component Binuclear Neutral Nickel(II) Catalyst," Organometallics, 2005, 24(11):2628-2632.

Hu et al., "Novel highly active binuclear neutral nickel and palladium complexes as precatalysts for norboernene polymerization," Journal of Molecular Catalysis A: Chemical 253, 2006, 155-164.

Huang et al, "The prognostic significance of PD-L1 in bladder cancer," Oncol. Rep., 2015, 33:3075-3084.

Huddle et al., "Reactions of alkyl-lithium compounds with aryl halides ," J Chem Soc., Perkin I, 1980, 12:2617-2625.

HuGEMM™ and HuCELL™ Models, "FactSheet," CrownBio, Oct. 2016, 8 pages.

Indian Office Action with Indian Application No. 201817026809, dated Apr. 29, 2020, 6 pages.

International Preliminary Report on Patentability in International Application No. PCT/US2016/057487, dated May 3, 2018, 7 pages.

International Preliminary Report on Patentability in International Application No. PCT/US2016/062730, dated May 31, 2018, 7 pages.

International Preliminary Report on Patentability in International Application No. PCT/US2016/067155, dated Jun. 19, 2018, 10 pages.

International Preliminary Report on Patentability in International Application No. PCT/US2016/067925, dated Jun. 26, 2018, 8 pages.

International Preliminary Report on Patentability in International Application No. PCT/US2017/031242, dated Nov. 6, 2018, 7 pages.

International Preliminary Report on Patentability in International Application No. PCT/US2017/034173, dated Nov. 27, 2018, 8 pages.

International Preliminary Report on Patentability in International Application No. PCT/US2017/038120, dated Dec. 25, 2018, 6 pages.

International Preliminary Report on Patentability in International Application No. PCT/US2017/041899, dated Jan. 15, 2019, 7 pages.

International Preliminary Report on Patentability in International Application No. PCT/US2017/048880, dated Mar. 5, 2019, 9 pages.

International Preliminary Report on Patentability in International Application No. PCT/US2017/067904, dated Jun. 25, 2019, 7 pages.

International Preliminary Report on Patentability in International Application No. PCT/US2017/067951, dated Jun. 25, 2019, 8 pages.

International Preliminary Report on Patentability in International Application No. PCT/US2017/067880, dated Jun. 25, 2019, 7 pages.

International Preliminary Report on Patentability in International Application No. PCT/US2017/067984, dated Jun. 25, 2019, 7 pages.

International Preliminary Report on Patentability in International Application No. PCT/US2017/067946, dated Jun. 25, 2019, 9 pages.

International Preliminary Report on Patentability in International Application No. PCT/US2017/067886, dated Jun. 25, 2019, 9 pages.

International Preliminary Report on Patentability in International Application No. PCT/US2019/025036, dated Oct. 15, 2020, 7 pages.

International Search Report and Written Opinion in International Application No. PCT/US2016/057487, dated Dec. 8, 2016, 11 pages.

International Search Report and Written Opinion in International Application No. PCT/US2016/062730, dated Feb. 9, 2017, 12 pages.

International Search Report and Written Opinion in International Application No. PCT/US2016/067925, dated Mar. 27, 2017, 13 pages.

International Search Report and Written Opinion in International Application No. PCT/US2016/067155, dated Apr. 24, 2017, 26 pages.

International Search Report and Written Opinion in International Application No. PCT/US2017/031242, dated Jun. 20, 2017, 22 pages.

International Search Report and Written Opinion in International Application No. PCT/US2017/034173, dated Aug. 8, 2017, 15 pages.

International Search Report and Written Opinion in International Application No. PCT/US2017/041899, dated Sep. 5, 2017, 12 pages.

International Search Report and Written Opinion in International Application No. PCT/US2017/038120, dated Aug. 1, 2017, 14 pages.

International Search Report and Written Opinion in International Application No. PCT/US2017/067904, dated Mar. 22, 2018, 14 pages.

International Search Report and Written Opinion in International Application No. PCT/US2017/067880, dated Mar. 21, 2018, 13 pages.

International Search Report and Written Opinion in International Application No. PCT/US2017/067984, dated Mar. 22, 2018, 14 pages.

International Search Report and Written Opinion in International Application No. PCT/US2017/067886, dated Mar. 23, 2018, 24 pages.

International Search Report and Written Opinion in International Application No. PCT/US2017/067946, dated May 22, 2018, 16 Pages.

(56) References Cited

OTHER PUBLICATIONS

International Search Report and Written Opinion in International Application No. PCT/US2017/067951, dated Mar. 27, 2018, 15 pages.
International Search Report and Written Opinion in International Application No. PCT/US2017/048880, dated Oct. 23, 2017, 15 pages.
International Search Report and Written Opinion in International Application No. PCT/US2019/031728, dated Jun. 25, 2019, 12 pages.
International Search Report and Written Opinion in International Application No. PCT/US2019/025036, dated Jul. 3, 2019, 12 pages.
International Search Report and Written Opinion in International Application No. PCT/US2020/045311, dated Oct. 2, 2020, 14 pages.
Israeli Office Action in Israeli Application No. 259,406, dated Mar. 11, 2020, 10 pages.
Israeli Office Action in Israeli Application No. 260,166, dated Jun. 2, 2020, 13 pages.
Iwai et al, "Involvement of PD-L1 on tumor cells in the escape from host immune system and tumor immunotherapy by PD-L1 blockade," PNAS, Sep. 2002, 99(19):12293-12297.
Japanese Office Action in Japanese Application No. 2018526213, dated Oct. 13, 2020, 10 pages.
Jiang et al., "Self-immobilizing binuclear neutral nickel catalyst for ethylene polymerization: Synthesis and catalytic studies," J Mol Cat., 2013, 380:139-143.
Kayal et al., "3,3'-Bis(triphenylsilyl)biphenoxide as a Sterically Hindered Ligand on Fe(II), Fe(III), and Cr(II)," Inorg Chem., 2002, 41(2):321-330.
Keir et al., "PD-1 and Its Ligands in Tolerance and Immunity," Annu. Rev. Immunol., 2008, 26:677-704.
Kerekes et al., "Aurora kinase inhibitors based on the imidazo[1,2-a]pyrazine core: fluorine and deuterium incorporation improve oral absorption and exposure," J Med Chem., 2011, 54(1):201-210.
Koch et al., "Nucleophilic reactions of pyridines and imidazoles with vinyl and aromatic halides," J Org Chem., 1993, 58(6):1409-1414.
Komiyama et al., "IL-17 Plays an Important Role in the Development of Experimental Autoimmune Encephalomyelitis," J. Immunol., Jul. 2006, 177:566-73.
Latchman et al, "PD-L2 is a second ligand for PD-1 and inhibits T cell activation," Nat. Immunol., Mar. 2001, 2(3):261-268.
Lazar-Molnar et al., "Crystal structure of the complex between programmed death-1 (PD-1) and its ligand PD-L2," PNAS, Jul. 2008, 105(30):10483-10488.
Legon'kova et al., "Interaction of o,o-dihalo o'-hydroxy azo compounds with metallic copper. II. Preparation of oligomeric azo compounds from monoazo compounds," Mosk Khim-Tekhnol Inst im Mendeleeva., 1968, 11(11):1281-1284 Machine Translation.
Legon'kova et al., "Interaction of o,o-dihalogeno o-hydroxy azo compounds with metallic copper," Trudy Instituta—Moskovskii Khimiko-Tekhnologicheskii Institut imeni D. I. Mendeleeva, 1965, 48:120-125 Machine Translation.
Lehtonen et al., "Comparison of quaternary methyl-, ethyl- and butylammonium hydroxides as alkylating reagents in pyrolysis-GC/MS studies of aquatic fulvic acid," Journal of Analytical and Applied Pyrolysis, 2003, 68-69:315-329.
Li et al., "A Mini-Review for Cancer Immunotherapy: Molecular Understanding of PD-1/PD-L1 Pathway & Translational Blockade of Immune Checkpoints," Int. J. Mol. Soc., 2016, 17:1151, 22 pages.
Li et al., "Analysis of Receptor Tyrosine Kinase Internalization Using Flow Cytometry," Methods Mol. Biol., 2008, 457:305-317.
Li et al., "Asymmetric Alternating Copolymerization of Meso-epoxides and Cyclic Anhydrides: Efficient Access to Enantiopure Polyesters," J. Am. Chem. Soc., 2016, 138(36):11493-11496.
Li et al., "A 3D Mesomeric Supramolecular Structure of a Cu(II) Coordination Polymer with 1,1'-Biphenyl-2,2',3,3'-tetracarboxylic Acid and 5,5'-Dimethyl-2,2'-bipyridine Ligands," J Inorg and Organomet Poly Mat., 2012, 22(6):1320-1324.
Li et al., "Discovery of peptide inhibitors targeting human programmed death 1 (PD-1) receptor," Oncotarget, Aug. 2016, 7(40):64967-64976.
Lin et al., "The PD-1/PD-L1 complex resembles the antigen-binding Fv domains of antibodies and T cell receptors," PNAS, Feb. 2008, 105(8):3011-3016.
Lipson et al., "From Discovery to Development: Blocking PD-1 and its Ligands," The Melanoma Letter, A Publication of The Skin Cancer Foundation, vol. 31, Summer 2013, 6 pages.
Liu et al., "Asymmetric Copolymerization of CO2 with meso-Epoxides Mediated by Dinuclear Cobalt(III) Complexes: Unprecedented Enantioselectivity and Activity," Angewandte Chemie, 2013, 52(44):11594-11598.
Liu et al., "Development of amino- and dimethylcarbamate-substituted resorcinol as programmed cell death-1 (PD-1) inhibitor," Eur J Pharm Sci, 2016, 88:50-58.
Mahoney et al., "The Next Immune-Checkpoint Inhibitors:PD-1/PD-L1 Blockade in Melanoma," Clin. Therapeutics, Nov. 2015, 37(4):761-782.
Maier et al., "Effects of the stationary phase and the solvent on the stereodynamics of biphep ligands quantified by dynamic three-column HPLC," Angewante Chemie, 2012, 51(12):2985-2988.
Manecke et al., "Preparation and properties of monomeric and polymeric Schiff bases derived from salicylaldehyde and 2,5-dihydroxyterephthalaldehyde. II. Electrical conductivity," Makromolekulare Chemie, 1972, 160:111-126 English Abstract.
Manecke et al., "Preparation and properties of chelate-forming monomeric and polymeric Schiff bases derived from salicylaldehyde and 2,5-dihydroxyterephthalaldehyde. I," Makromolekulare Chemie, 1970, 133:61-82 English Abstract.
Mochida et al., "Rhodium-Catalyzed Regioselective Olefination Directed by a Carboxylic Group," J Org Chem, 2011, 76(9):3024-3033.
Moneta et al., "Boron templated synthesis of macrocyclic hosts containing convergent hydroxy or methoxy groups," Bulletin de la Societe Chimique de France, 1988, 6:995-1004 (English Abstract).
Nallasivam et al., "Development of Unimolecular Tetrakis(piperidin-4-ol) as a Ligand for Suzuki-Miyaura Cross-Coupling Reactions: Synthesis of Incrustoporin and Preclamol," 2015, Eur J Org Chem., 2015(16):3558-3567.
Nero et al., "Oncogenic protein interfaces: small molecules, big challenges," Nature Reviews, Apr. 2014, 14:248-262.
Nishimura et al, "Autoimmune Dilated Cardiomyopathy in PD-1 Receptor-Deficient Mice," Science, Jan. 2001, 291:319-322.
Nishimura et al, "Development of Lupus-like Autoimmune Diseases by Disruption of the PD-1 Gene Encoding an ITIM Motif-Carrying Immunoreceptor," Immunity, Aug. 1999, 11:141-151.
Nishimura et al., "PD-1: an inhibitory immunoreceptor involved in peripheral tolerance," TRENDS in Immunology, May 2001, 22(5):365-268.
Nishino et al., "Copper-Mediated C—H/C—H Biaryl Coupling of Benzoic Acid Derivatives and 1,3-Azoles," Angew. Chem. Int. Ed., 2013, 52:4457-4461.
Normand et al., "Dinuclear vs. mononuclear complexes: accelerated, metal-dependent ring-opening polymerization of lactide," Chem. Commun., 2013, 49(99):11692-11694.
Okazaki and Honjo, "The PD-1-PD-L pathway in immunological tolerance," Trends Immunol., Apr. 2006, 4:195-201.
Okazaki et al., "A rheostat for immune responses: the unique properties of PD-1 and their advantages for clinical application," Nature Immunology, Dec. 2013, 14(12):1212-1218.
Paek et al.., "Facile syntheses and multi-orthofunctionalizations of tertiary benzamides," Bulletin of the Korean Chemical Society, 1993, 14(6):732-739.
Paek et al., "Chiral host. Attempted synthesis using McMurray reaction as a final ring closure method," Bulletin of the Korean Chemical Society, 1989, 10(6):572-577.
Pardoll, "The blockade of immune checkpoints in cancer immunotherapy," Nature, Apr. 2012, 12:252-264.

(56) References Cited

OTHER PUBLICATIONS

Parry et al., "CTLA-4 and PD-1 Receptors Inhibit T-Cell Activation by Distinct Mechanisms," Mol. Cell. Biol., Nov. 2005, 25(21):9543-9553.
Parsons et al., "Directed ortho metalation reactions. Expedient synthesis of 3,3'-disubstituted 1,1'-bi-(2-phenols) (BIPOLS)," Tetrahedron Letters, 1994, 35(41):7537-7540.
Pascolutti et al., "Structure and Dynamics of PD-L1 and an Ultra-High-Affinity PD-1 Receptor Mutant," Structure, Oct. 2016, 24:1719-1728.
Paulini et al., "Orthogonal Multipolar Interactions in Structural Chemistry and Biology," Angew. Chem. Int. Ed., 2005, 44:1788-1805.
Pearson et al., "The formation of complexes between aza-derivatives of crown ethers and primary alkylammonium salts. Part 5. Chiral macrocyclic diamines," J. Chem. Soc., Perkin I, 1979, 12:3113-3126.
Pfeiffer et al., "Inner complex salts of the aldimine and azo series," Journal fuer Praktische Chemie, 1937, 149:217-296 Machine Translation.
Pierre et al., "Synthesis of a new macrobicyclic siderophoric host molecule with six converging phenolate groups," Angewandte Chemie, 1991, 103(1):75-76 Machine Translation.
Postow et al, "Immune Checkpoint Blockade in Cancer Therapy," J. Clinical Oncology, Jun. 2015, 33(17):1974-1982.
Press Release Archive, "Boehringer Ingelheim and Yale University collaborate to investigate novel immunotherapy targets across several therapeutic areas," Boehringer Ingelheim, Jan. 13, 2015, 2 pages.
Puehlhofer et al., "SASAPOS cascades of perfluorinated aromatic carboxylic acids: low-temperature decarboxylation triggered by electrostatic effects of polycationic ligand sets," Euro J of Org Chem., 2004, 5:1002-1007.
Punniyamurthy et al., "Enantiomerically pure bicyclo[3.3.1]nona-2,6-diene as the sole source of enantioselectivity in BIPHEP-Rh asymmetric hydrogenation," Chem Comm., 2008, 41:5092-5094.
Sabatier et al, "Prognostic and predictive value of PDL1 expression in breast cancer," Oncotarget, Mar. 2015, 6(7):5449-5464.
Sharpe et al, "The function of programmed cell death 1 and its ligands in regulating autoimmunity and infection," Nat. Immunol., Mar. 2007 8(3):239-245.
Sharpe et al., "The B7-CD28 Superfamily," Nature Reviews, Feb. 2002, 2:116-126.
Sharma et al., "Palladium-Catalyzed Decarboxylative Acylation of O-Phenyl Carbamates with Alpha-Oxocarboxylic Acids at Room Temperature," Advanced Synthesis & Catalysis, 2013, 355(4):667-672.
STN Search Report dated Apr. 14, 2016, 79 pages.
STN Search Report dated Apr. 29, 2016, 69 pages.
STN Search Report dated Aug. 30, 2016, 4 pages.
STN Search Report dated Jun. 6, 2016, 115 pages.
STN Search Report dated Sep. 2, 2016, 115 pages.
STN Search Report, dated May 1, 2016, 12 pages.
STN Search Report dated May 24, 2016, 92 pages.
STN Search Report dated Sep. 12, 2016, 4 pages.
STN Search Report dated Jun. 16, 2016, 8 pages.
STN Search Report dated Sep. 12, 2016, 17 pages.
STN Search Report dated Jul. 12, 2016, 4 pages.
STN Search Report dated Aug. 19, 2016, 23 pages.
STN Search Report dated Dec. 15, 2016, 4 pages.
STN Search Report dated Dec. 19, 2016, 11 pages.
STN Search Report dated Dec. 16, 2016, 25 pages.
STN Search Report dated Dec. 16, 2016, 4 pages.
STN Search Report dated Dec. 20, 2016, 117 pages.
STN Search Report dated Sep. 27, 2017, 4 pages.
STN Search Report dated Mar. 27, 2018, 4 pages.
STN Search Report dated Apr. 30, 2018, 8 pages.
Sorrell et al., "3,3'-Disubstituted 2,2'-biphenols. Synthesis of nonplanar, tetradentate chelating ligands," J Org Chem., 1985, 50(26):5765-5769.
Storz, "Intellectual property issues of immune checkpoint inhibitors," mAbs, Jan. 2016, 8(1):10-26.
Sumrit et al., "Aluminum complexes containing salicylbenzoxazole ligands and their application in the ring-opening polymerization of rac-lactide and $\epsilon$-caprolactone," Dalton Transactions (2016), 45(22), 9250-9266.
Tang et al., "Facile synthesis of enantioenriched phenol-sulfoxides and their aluminum complexes," Org Biomol Chem., 2016, 14(24):5580-5585.
Thiel et al., "Small-Molecule Stabilization of Protein-Protein Interactions: An Underestimated Concept in Dmg Discoveiy?" Angew. Chem. Int. Ed., 2012, 51:2012-2018.
Tucker et al., "Host-guest complexation. 52. Bridged and chiral hemispheranids," J Org Chem., 1989, 54(23):5460-5482.
Unrau et al., "Directed ortho metalation. Suzuki cross coupling connections. Convenient regiospecific routes to functionalized m- and p-teraryls and m-quinquearyls," Tetrahedron Letters, 1992, 33(20):2773-2776.
Velcheti et al., "Programmed death-1/programmed death-1 ligand axis as a therapeutic target in oncology: current insights," Journal of Receptor Ligand and Channel Research, Dec. 2014, 8(23): 1-7.
Wang et al, "The prognostic value of PD-L1 expression for non-small cell lung cancer patients: A meta-analysis," Eur. J. Surg. Oncol., 2015, 41:450-456.
Wang et al., "A binuclear Zn(II)-Zn(II) complex from a 2-hydroxybenzohydrazide-derived Schiff base for selective detection of pyrophosphate," Dalton Transactions, Oct. 2014, 43(37):14142-14146.
Wang et al., "Molecular Modeling and Functional Mapping of B7-H1 and B7-DC Uncouple Costimulatory Function from PD-1 Interaction," J. Exp. Med., Apr. 2013, 197(3):1083-1091.
Wei et al., "Strength of PD-1 signaling differentially affects T-cell effector functions," PNAS, Apr. 2013, E2480-E2489.
Weinmann, "Cancer Immunotherapy: Selected Targets and Small-Molecule Modulators," Chem. Med. Chem., 2016, 11:450-466.
Weiss et al., "Electrostatics and color: Massive electrostatic perturbation of chromophores by ion cluster ligands," J Am Chem Soc., 2007, 129(3):547-553.
Weiss et al., "Electrostatic activation of SNAr-reactivity by sulfonylonio substituents," Zeitschrift fuer Naturforschung, 2001, 56(12): 1360-1368 English Abstract.
Weiss et al., "First-ever per(onio) substitution of benzene: the role of the counterion," Angewandte Chemie, 1995, 34(12):1319-1321.
Weiss et al., "Massive electrostatic effects on heteropolar C—C disconnections: Transforming a phenyl anion into a potent leaving group," Euro J Org Chem., 2005, 16:3530-3535.
Weiss et al., "Poly-onio substituted quinones as strong electron acceptors," Inst Org Chem., 1986, 98(10):925-926.
Weiss et al., "SASAPOS, not Sisyphus: highly efficient 20-step one-pot synthesis of a discrete organic-inorganic ion cluster with a porphyrin core," Angewandte Chemie International Edition, 2002, 41(20):3815-3817.
Weiss et al., "Syntheses and Reactions of Polycationically Substituted Azido- and Diazidobenzenes," Eur J Org Chem., Nov. 2007, 31:5270-5276.
Wells et al., "Reaching for high-hanging fruit in dmg discovery at protein-protein interfaces," Nature, Dec. 2007, 450:1001-1009.
Wu et al., "Targeting the BACE1 Active Site Flap Leads to a Potent Inhibitor That Elicits Robust Brain A$\beta$ Reduction in Rodents," ACS Medicinal Chemistry Letters, 2016, 7(3):271-276.
www.medscape.com' [online]. "The 'Family Business' Behind the Flurry of PD-1 Inhibitors," Sep. 10, 2014. [Retrieved on Jan. 29, 2015]. Retrieved from the Internet: URL<http://www.medscape.com/viewarticle/831448_print>. 3 pages.
Xiong et al., "Biaryl-Bridged Salalen Ligands and Their Application in Titanium-Catalyzed Asymmetric Epoxidation of Olefins with Aqueous H2O2," Eur J Org Chem., 2011, 23:4289-4292.
Xu et al., "Quantitative structure-activity relationship study on BTK inhibitors by modified multivariate adaptive regression spline and CoMSIA methods," SAR QSAR Environ Res., 2015, 26(4):279-300.

(56) References Cited

OTHER PUBLICATIONS

Xu et al., "Design, synthesis and biological evaluation of deuterated nintedanib for improving pharmacokinetic properties," J Label Compd RadioPharm., Jun. 15, 2015, 58(7):308-312.
Yin et al., "Strategies for Targeting Protein-Protein Interactions With Synthetic Agents," Angew. Chem. Int. Ed., 2005, 44:4130-4163.
Young et al., "Discovery of highly potent and selective Bruton's tyrosine kinase inhibitors: Pyridazinone analogs with improved metabolic stability," Bioorganic & Medicinal Chemistry Letters, 2016, 26(2):575-579.
Young et al., "Potent and selective Bruton's tyrosine kinase inhibitors: Discovery of GDC-0834," Bioorganic & Medicinal Chemistry Letters, 2015, 25(6):1333-1337.
Zarganes-Tzitzikas, "Inhibitors of programmed cell death 1 (PD-1): a patent review (2010-2015)," Expert Opinion on Therapeutic Patents, Sep. 19, 2016, 26(9):973-977.
Zak et al., "Structural basis for small molecule targeting of the programmed death ligand 1 (PD-L1)," Oncotarget, 2016, 7(21):30323-30335.
Zak et al., "Structural basis for small molecule targeting of the programmed death ligand 1 (PD-L1)" Oncotarget, Apr. 2016, 19 pages; Supplemental Material for 2016, 7(21):30323-30335.
Zak et al., "Structure of the Complex of Human Programmed Death 1, PD-1, and Its Ligand PD-L1: with Supplemental Information," Structure, Dec. 2015, 23:2341-2348.
Zang et al., "Four 2D metal-organic networks incorporating Cd-cluster SUBs: hydrothermal synthesis, structures and photoluminescent properties," CrystEngComm, 2009, 11(1):122-129.
Zhan et al., "From monoclonal antibodies to small molecules: the development of inhibitors targeting the PD-1/PD-L1 pathway," Drug Discovery Today, Apr. 2016, 10 pages.
Zhang et al., "Electrospray mass spectrum of a per(onio)-substituted benzene: retention of Coulombic charge upon collisionally activated decomposition," J Am Soc. Mass. Spectrom., 1998, 9(1):15-20.
Zhang et al., "Non-symmetrical diarylcarboxylic acids via rhodium(I)-catalyzed regiospecific cross-dehydrogenation coupling of aromatic acids: twofold direct C—H bond activations in water," RSC Advances, 2016, 6(64):91617-91620.
Zhang et al., "Structural and Functional Analysis of the Costimulatory Receptor Programmed Death-1," Immunity, Mar. 2004, 20:337-347.
Zhang et al., "Biaryl-Based Macrocyclic and Polymeric Chiral (Salophen)Ni(II) Complexes: Synthesis and Spectroscopic Study," J Org Chem., 2001, 66(2):481-487.
Zhao et al., "Design, synthesis and organocatalysis of 2,2'-biphenol-based prolinamide organocatalysts in the asymmetric direct aldol reaction in water," Synlett, 2013, 24(20):2743-2747.
Camara et al., "Multiple dermatofibromas: Dermoscopic patterns," Indian journal of dermatology, 2013, 58(3):243.
Chilean Office Action in Chilean Application No. 2922-2020, dated Dec. 8, 2021, 21 pages.
Gu et al., "Undo the brake of tumour immune tolerance with antibodies, peptide mimetics and small molecule compounds targeting PD-1/PD-L1 checkpoint at different locations for acceleration of cytotoxic immunity to cancer cells," Clinical and Experimental Pharmacology and Physiology, 2019, 46(2):105-115.
Huang et al., "Pharmacological treatment for keloids," Expert opinion on pharmacotherapy, 2013, 14(15):2087-2100.
International Preliminary Report on Patentability in International Application No. PCT/US2020/045311, dated Feb. 17, 2022, 8 pages.
Israeli Office Action in Israeli Application No. 287,267, dated Feb. 15, 2022, 4 pages.
Lexico.com, "Synonyms of Enhance," Oxford Dictionary, retrieved on Dec. 9, 2021, retrieved from URL <https://www.lexico.conn/synonynns/enhance>, 4 pages.
Suarez et al., "Inhibitors of TAM subfamily of tyrosine kinases: synthesis and biological evaluation," European Journal of Medicinal Chemistry, 2013, 61:2-25.
Yao et al., "PD-1 as an Immune Modulatory Receptor," Cancer J., 2014, 20(4):262-264.
Argentina Office Action in Argentina Application No. 20170103634, dated Jan. 27, 2022, 7 pages.
Australian Notice of Allowance in Australian Application No. 2017382870, dated Mar. 15, 2022, 4 pages.
Azuma et al., "B7-H1 is a ubiquitous antiapoptotic receptor on cancer cells," BLOOD, Apr. 1, 2018, 111(7):3635-3643.
Bastin et al., "Salt Selection and Optimisation for Pharmaceutical New Chemical Entities," Org Proc Res Dev., dated Jan. 1, 2000, pp. 4(5):427-435.
Caira, "Crystalline Polymorphism of Organic Compounds," Topics in Current Chemistry, Jan. 1, 1998, 198:163-208.
Cheng et al., "Cancer-associated fibroblasts induce PDL1+ neutrophils through the IL6-STAT3 pathway that foster immune suppression in hepatocellular carcinoma," Cell Death and Disease, 2018, 9:422.
Dong et al., "Tumor-associated B7-H1 promotes T-cell apoptosis: a potential mechanism of immune evasion," Nature Medicine, Aug. 2002, 8(8):793-800.
European Communication in European Application No. 20202254.7, dated Apr. 1, 2022, 4 pages.
Highlights Prescribing Information, "KEYTRUDA," Revised Feb. 2019, 66 pages.
Highlights Prescribing Information, "OPDIVO," Revised Apr. 2019, 90 pages.
Indian Office Action in Indian Application No. 202017053661, dated Jun. 3, 2022, 5 pages.
International Preliminary Report on Patentability in International Application No. PCT/US2020/053190, dated Apr. 5, 2022, 7 pages.
International Preliminary Report on Patentability in International Application No. PCT/US2020/059817, dated May 17, 2022, 12 pages.
International Search Report and Written Opinion in International Application No. PCT/US2021/058268, dated Apr. 21, 2022, 22 pages.
International Search Report and Written Opinion in International Application No. PCT/US2021/058334, dated Apr. 25, 2022, 23 pages.
International Search Report and Written Opinion in International Application No. PCT/US2021/058338, dated Feb. 9, 2022, 15 pages.
International Search Report and Written Opinion in International Application No. PCT/US2021/063965, dated Apr. 12, 2022, 20 pages.
Invitation to Pay Fee's in International Application No. PCT/US2021/058268, dated Jan. 31, 2022, 16 pages.
Invitation to Pay Fee's in International Application No. PCT/US2021/058334, dated Feb. 3, 2022, 12 pages.
Reck et al., "Pembrolizumab versus Chemotherapy for PD-L1-Positive Non-Small-Cell Lung Cancer," N Engl J Med., Nov. 10, 2016, 375(19):1823-1833.
Rowe et al., "Fumaric Acid" Handbook of pharmaceutical excipients, Jan. 1, 2009, pp. 276-277, 309-310, 393-396.
Sznol et al., "Antagonist Antibodies to PD-1 and B7-H1 (PD-L1) in the Treatment of Advanced Human Cancer," Clin Cancer Res., Mar. 1, 2013, 19(5):1021-1034.
Vaddepally et al., "Review of Indications of FDA-Approved Immune Checkpoint Inhibitors per NCCN Guidelines with the Level of Evidence," Cancers, 2020, 12(3):738.

* cited by examiner

SALTS OF A PD-1/PD-L1 INHIBITOR

CROSS-REFERENCE TO RELATED APPLICATIONS

The present application claims the benefit of U.S. Provisional Application No. 62/884,996, filed Aug. 9, 2019, which is incorporated herein by reference in its entirety.

FIELD OF THE INVENTION

This application relates to salt forms of the PD-1/PD-L1 inhibitor (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid, including methods of preparation thereof, where the compound is useful in the treatment of various diseases including infectious diseases and cancer.

BACKGROUND OF THE INVENTION

The immune system plays an important role in controlling and eradicating diseases such as cancer. However, cancer cells often develop strategies to evade or to suppress the immune system in order to favor their growth. One such mechanism is altering the expression of co-stimulatory and co-inhibitory molecules expressed on immune cells (Postow et al, J. Clinical Oncology 2015, 1-9). Blocking the signaling of an inhibitory immune checkpoint, such as PD-1, has proven to be a promising and effective treatment modality.

Programmed cell death-1 (PD-1), also known as CD279, is a cell surface receptor expressed on activated T cells, natural killer T cells, B cells, and macrophages (Greenwald et al, Annu. Rev. Immunol 2005, 23:515-548; Okazaki and Honjo, Trends Immunol 2006, (4):195-201). It functions as an intrinsic negative feedback system to prevent the activation of T-cells, which in turn reduces autoimmunity and promotes self-tolerance. In addition, PD-1 is also known to play a critical role in the suppression of antigen-specific T cell response in diseases like cancer and viral infection (Sharpe et al, *Nat Immunol* 2007 8, 239-245; Postow et al, J. Clinical Oncol 2015, 1-9).

The structure of PD-1 consists of an extracellular immunoglobulin variable-like domain followed by a transmembrane region and an intracellular domain (Parry et al, Mol Cell Biol 2005, 9543-9553). The intracellular domain contains two phosphorylation sites located in an immunoreceptor tyrosine-based inhibitory motif and an immunoreceptor tyrosine-based switch motif, which suggests that PD-1 negatively regulates T cell receptor-mediated signals. PD-1 has two ligands, PD-L1 and PD-L2 (Parry et al, Mol Cell Biol 2005, 9543-9553; Latchman et al, Nat Immunol 2001, 2, 261-268), and they differ in their expression patterns. PD-L1 protein is upregulated on macrophages and dendritic cells in response to lipopolysaccharide and GM-CSF treatment, and on T cells and B cells upon T cell receptor and B cell receptor signaling. PD-L1 is also highly expressed on almost all tumor cells, and the expression is further increased after IFN-γ treatment (Iwai et al, PNAS2002, 99(19):12293-7; Blank et al, Cancer Res 2004, 64(3):1140-5). In fact, tumor PD-L1 expression status has been shown to be prognostic in multiple tumor types (Wang et al, Eur J Surg Oncol 2015; Huang et al, Oncol Rep 2015; Sabatier et al, Oncotarget 2015, 6(7): 5449-5464). PD-L2 expression, in contrast, is more restricted and is expressed mainly by dendritic cells (Nakae et al, J Immunol 2006, 177:566-73). Ligation of PD-1 with its ligands PD-L1 and PD-L2 on T cells delivers a signal that inhibits IL-2 and IFN-γ production, as well as cell proliferation induced upon T cell receptor activation (Carter et al, Eur J Immunol 2002, 32(3):634-43; Freeman et al, J Exp Med 2000, 192(7):1027-34). The mechanism involves recruitment of SHP-2 or SHP-1 phosphatases to inhibit T cell receptor signaling such as Syk and Lck phosphorylation (Sharpe et al, Nat Immunol 2007, 8, 239-245). Activation of the PD-1 signaling axis also attenuates PKC-θ activation loop phosphorylation, which is necessary for the activation of NF-κB and AP1 pathways, and for cytokine production such as IL-2, IFN-γ and TNF (Sharpe et al, Nat Immunol 2007, 8, 239-245; Carter et al, Eur J Immunol 2002, 32(3):634-43; Freeman et al, J Exp Med 2000, 192(7):1027-34).

Several lines of evidence from preclinical animal studies indicate that PD-1 and its ligands negatively regulate immune responses. PD-1-deficient mice have been shown to develop lupus-like glomerulonephritis and dilated cardiomyopathy (Nishimura et al, Immunity 1999, 11:141-151; Nishimura et al, Science 2001, 291:319-322). Using an LCMV model of chronic infection, it has been shown that PD-1/PD-L1 interaction inhibits activation, expansion and acquisition of effector functions of virus-specific CD8 T cells (Barber et al, Nature 2006, 439, 682-7). Together, these data support the development of a therapeutic approach to block the PD-1-mediated inhibitory signaling cascade in order to augment or "rescue" T cell response. Accordingly, there is a need for new compounds and salts that block PD-1/PD-L1 protein/protein interaction.

SUMMARY OF THE INVENTION

The present disclosure is directed to salts of (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid.

The present disclosure is further directed to the mono-hydrobromic acid salt, the mono-oxalic acid salt, the mono-hydrochloric acid salt, the mono-L-tartaric acid salt, the di-hydrobromic acid salt, the di-oxalic acid salt, the L-tartaric acid salt (1:1.5), the hydrochloric acid salt (1:1.7), the mono-malonic acid salt, the phosphoric acid salt (~1:3), and the phosphoric acid salt (~1:2) of (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid.

The present disclosure is further directed to crystalline forms of the salts described herein.

The present disclosure is further directed to pharmaceutical compositions comprising a salt or crystalline form described herein, and at least one pharmaceutically acceptable carrier or excipient. The present disclosure is further directed to solid dosage forms comprising the pharmaceutical compositions.

The present disclosure is further directed to a method of inhibiting PD-1/PD-L1 interaction comprising administering to a patient the salts and crystalline forms described herein. The present disclosure also provides uses of the salts and crystalline forms described herein in the manufacture of a medicament for use in inhibiting PD-1/PD-L1 interaction. The present disclosure also provides the salts and crystalline forms described herein for use in inhibiting PD-1/PD-L1 interaction.

The present disclosure is further directed to treating a disease or disorder associated with inhibition of PD-1/PD-L1 interaction comprising administering to a patient the salts and crystalline forms described herein. The present disclosure also provides uses of the salts and crystalline forms described herein in the manufacture of a medicament for use in treating a disease or disorder associated with inhibition of PD-1/PD-L1 interaction. The present disclosure also provides the salts and crystalline forms described herein for use in treating a disease or disorder associated with inhibition of PD-1/PD-L1 interaction.

The present disclosure is further directed to enhancing, stimulating and/or increasing the immune response in a patient comprising administering to a patient the salts and crystalline forms described herein. The present disclosure also provides uses of the salts and crystalline forms described herein in the manufacture of a medicament for use in enhancing, stimulating and/or increasing the immune response in a patient. The present disclosure also provides the salts and crystalline forms described herein for use in enhancing, stimulating and/or increasing the immune response in a patient.

The present invention is further directed to processes for preparing the salts and crystalline forms described herein.

DETAILED DESCRIPTION

Figure 1:
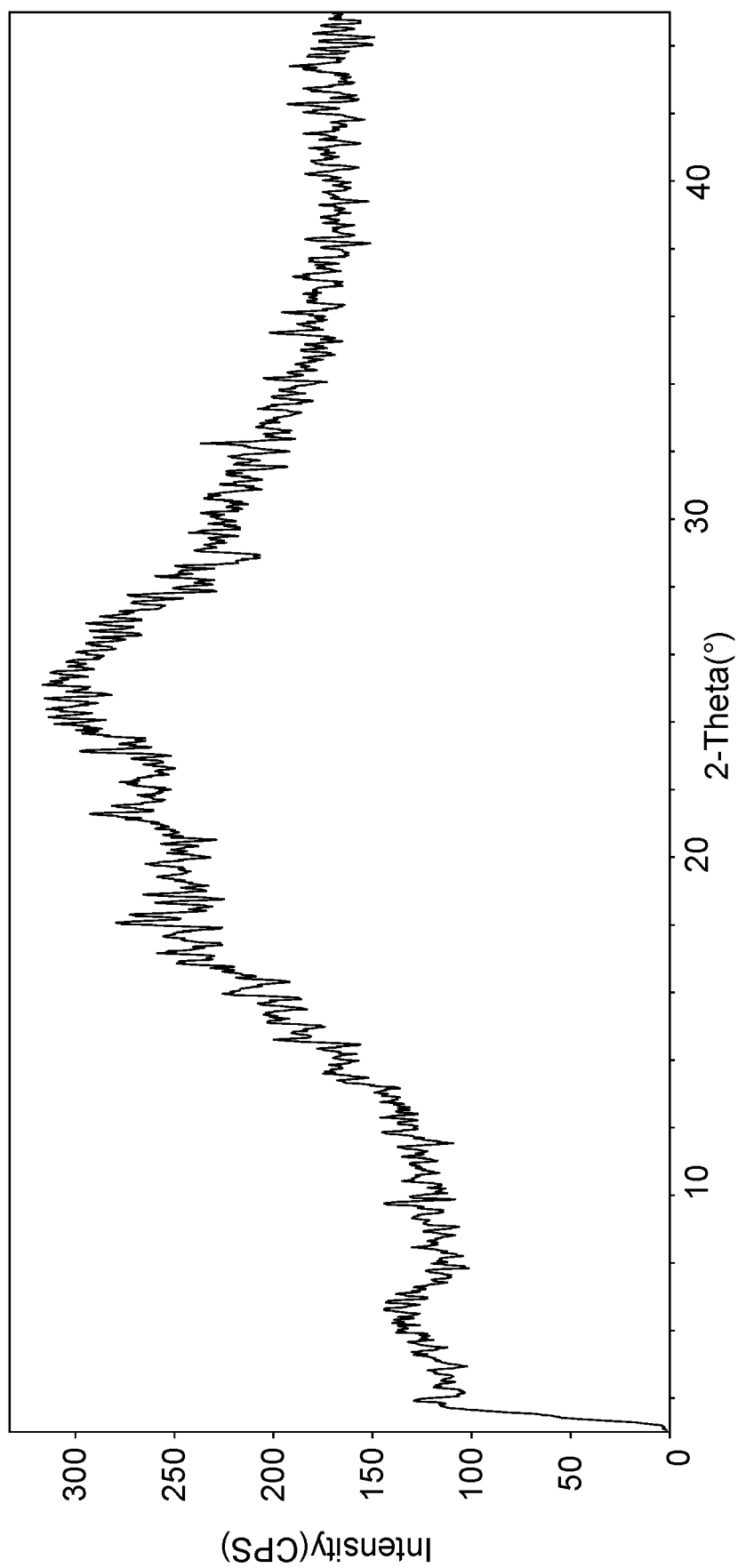
FIG. 1 shows an XRPD pattern of Compound 1 mono-hydrobromic acid salt.

The present disclosure is directed to, inter alia, a salt of (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid (Compound 1), wherein the salt is selected from:

(R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid hydrobromic acid salt (Compound 1 hydrobromic acid salt);

(R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid oxalic acid salt (Compound 1 oxalic acid salt);

(R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid hydrochloric acid salt (Compound 1 hydrochloric acid salt);

(R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid L-tartaric acid salt (Compound 1 L-tartaric acid salt);

(R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid malonic acid salt (Compound 1 malonic acid salt); and (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid phosphoric acid salt (Compound 1 phosphoric acid salt).

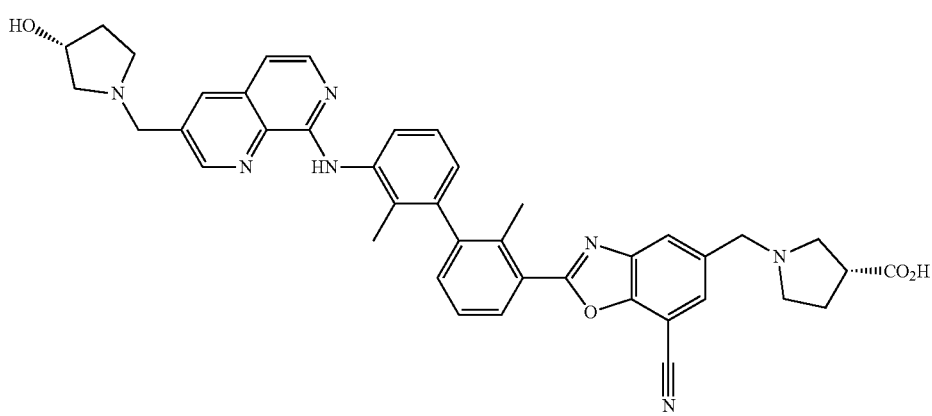

Compound 1

Compound 1 is described in US Patent Application Publication No. US 2018/0179197 A1, the entirety of which is incorporated herein by reference.

Hydrobromic Acid Salts

In some embodiments, the salt of Compound 1 is (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid hydrobromic acid salt (Compound 1 hydrobromic acid salt). In some embodiments, the Compound 1 hydrobromic acid salt is (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid mono-hydrobromic acid salt (Compound 1 mono-hydrobromic acid salt). In some embodiments, the Compound 1 hydrobromic acid salt is (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid di-hydrobromic acid salt (Compound 1 di-hydrobromic acid salt).

Compound 1 mono-hydrobromic acid salt can be prepared by any suitable method for the preparation of hydrobromic acid addition salts. For example, Compound 1 can be combined with hydrobromic acid (e.g., about 1.0 molar eq. or more) in a solvent and the resulting salt can be isolated by filtering the salt from solution. In certain embodiments, Compound 1 is combined with about 1 to about 2 molar equivalents of hydrobromic acid. In certain embodiments, Compound 1 is combined with about 1.0 to about 1.5 molar equivalents of hydrobromic acid. In certain embodiments, Compound 1 is combined with about 1.05 molar equivalents of hydrobromic acid.

The solvent can contain any solvent or mixture of solvents capable of at least partially dissolving Compound 1. In some embodiments, the solvent contains an alcohol. Suitable alcohols include methanol, ethanol, 2-nitroethanol, 2-fluoroethanol, 2,2,2-trifluoroethanol, ethylene glycol, 1-propanol, isopropanol (isopropyl alcohol, 2-propanol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol. In some embodiments, the solvent contains acetone, tetrahydrofuran, dichloromethane, methanol, ethanol, 1-propanol, or isopropanol. In some embodiments, the solvent contains dichloromethane. In some embodiments, the solvent contains tetrahydrofuran.

In some embodiments, the solvent is a mixture of isopropyl alcohol, methanol, water, and dichloromethane. In some embodiments, the solvent is a mixture of isopropyl alcohol, water, and tetrahydrofuran.

In some embodiments, the solvent is about room temperature. In some embodiments, the solvent is heated to a temperature of about 50° C. In some embodiments, the temperature is from about 50° C. to about 80° C. In some embodiments, the temperature is from about 40° C. to about 60° C. In some embodiments, the temperature is from about 45° C. to about 55° C. In some embodiments, the temperature is about 45° C., about 50° C., about 55° C., about 60° C., about 65° C., about 70° C., about 75° C. or about 80° C.

In some embodiments, the solvent is heated to a temperature that can induce precipitation at a practical rate. In some embodiments, precipitation is completed within about 12 to about 24 hours, but longer and shorter periods are possible depending on the choice of precipitation solvent and temperature. In some embodiments, precipitation is completed within about 12 hours. In some embodiments, precipitation is completed within about 2 hours.

The precipitation of Compound 1 mono-hydrobromic acid salt, in some embodiments, is carried out by filtering the salt from solution.

Figure 2:
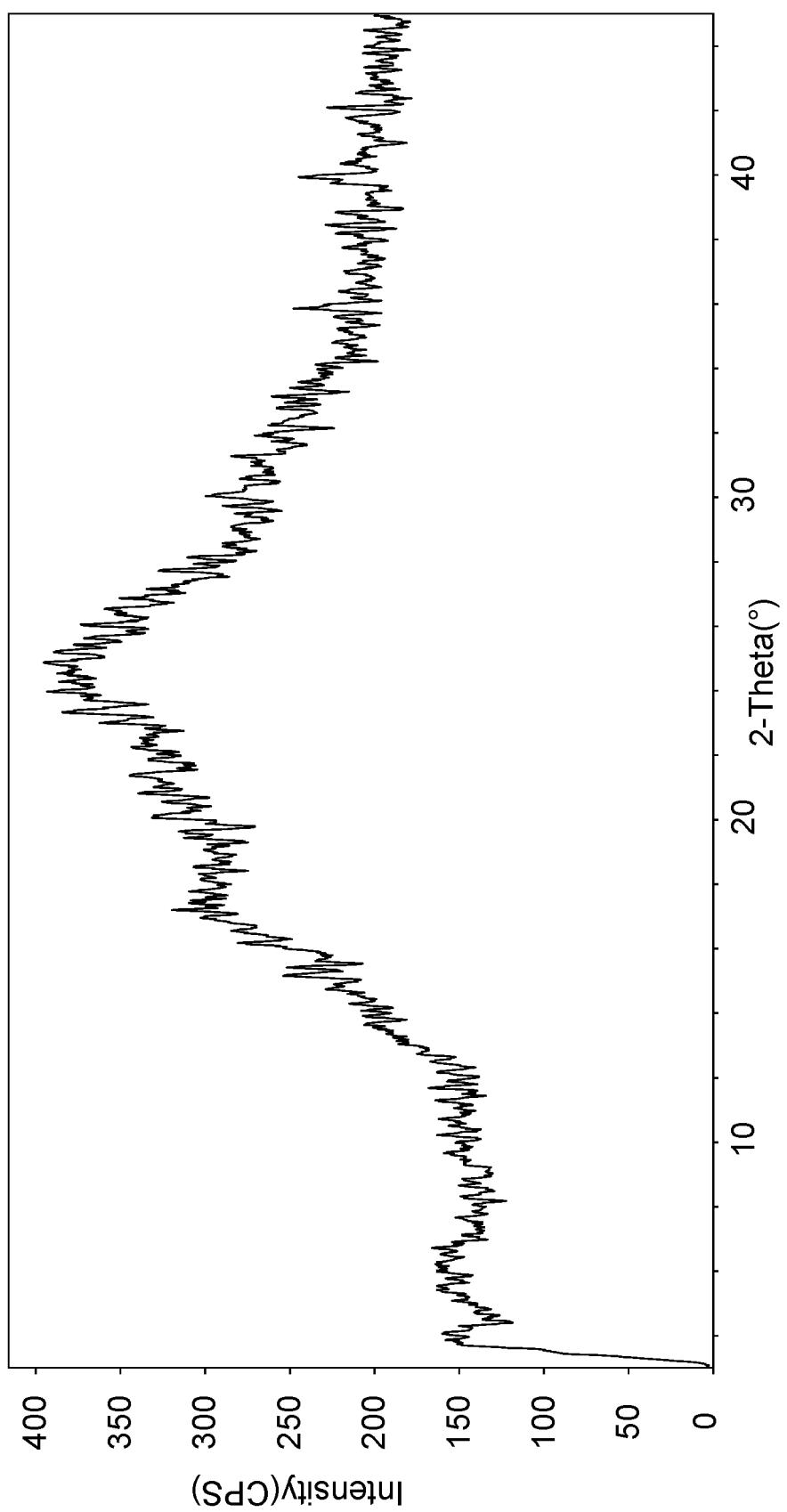
FIG. 2 shows an XRPD pattern of Compound 1 mono-hydrobromic acid salt prepared by an alternative method.

In some embodiments, Compound 1 mono-hydrobromic acid salt can be characterized by the X-ray powder diffraction (XRPD) pattern substantially as shown in FIG. 1. In some embodiments, Compound 1 mono-hydrobromic acid salt can be characterized by the X-ray powder diffraction (XRPD) pattern substantially as shown in FIG. 2.

In some embodiments, Compound 1 mono-hydrobromic acid salt is amorphous.

Compound 1 di-hydrobromic acid salt can be prepared by any suitable method for preparation of hydrobromic acid addition salts. For example, Compound 1 can be combined with hydrobromic acid (e.g., about 2.0 molar eq. or more) in a solvent and the resulting salt can be isolated by filtering the salt from solution. In certain embodiments, Compound 1 is combined with about 2 to about 3 molar equivalents of hydrobromic acid. In certain embodiments, Compound 1 is combined with about 2.0 to about 2.5 molar equivalents of hydrobromic acid. In certain embodiments, Compound 1 is combined with about 2.3 molar equivalents of hydrobromic acid. In certain embodiments, Compound 1 is combined with about 2.05 molar equivalents of hydrobromic acid.

The solvent can contain any solvent or mixture of solvents capable of at least partially dissolving Compound 1. In some embodiments, the solvent contains an alcohol. Suitable alcohols include methanol, ethanol, 2-nitroethanol, 2-fluoroethanol, 2,2,2-trifluoroethanol, ethylene glycol, 1-propanol, isopropanol (isopropyl alcohol, 2-propanol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol. In some embodiments, the solvent contains acetone, tetrahydrofuran, dichloromethane, methanol, ethanol, 1-propanol, or isopropanol. In some embodiments, the solvent contains methanol. In some embodiments, the solvent contains tetrahydrofuran.

In some embodiments, the solvent is a mixture of isopropyl alcohol, water and methanol. In some embodiments, the solvent is tetrahydrofuran. In some embodiments, the solvent is a mixture of isopropyl alcohol, water and tetrahydrofuran.

In some embodiments, the solvent is about room temperature. In some embodiments, the solvent is heated to a temperature of about 50° C. In some embodiments, the temperature is from about 50° C. to about 80° C. In some embodiments, the temperature is from about 40° C. to about 60° C. In some embodiments, the temperature is from about 45° C. to about 55° C. In some embodiments, the temperature is about 45° C., about 50° C., about 55° C., about 60° C., about 65° C., about 70° C., about 75° C. or about 80° C.

In some embodiments, the solvent is heated to a temperature that can induce precipitation at a practical rate. In some embodiments, precipitation is completed within about 12 to about 24 hours, but longer and shorter periods are possible depending on the choice of precipitation solvent and temperature. In some embodiments, the precipitation is completed within about 16 hours. In some embodiments, the precipitation is completed within about 12 hours. In some embodiments, the precipitation is completed within about 2.5 hours.

The precipitation and of the di-hydrobromic acid salt, in some embodiments, is carried out by filtering the salt from solution.

Figure 8:
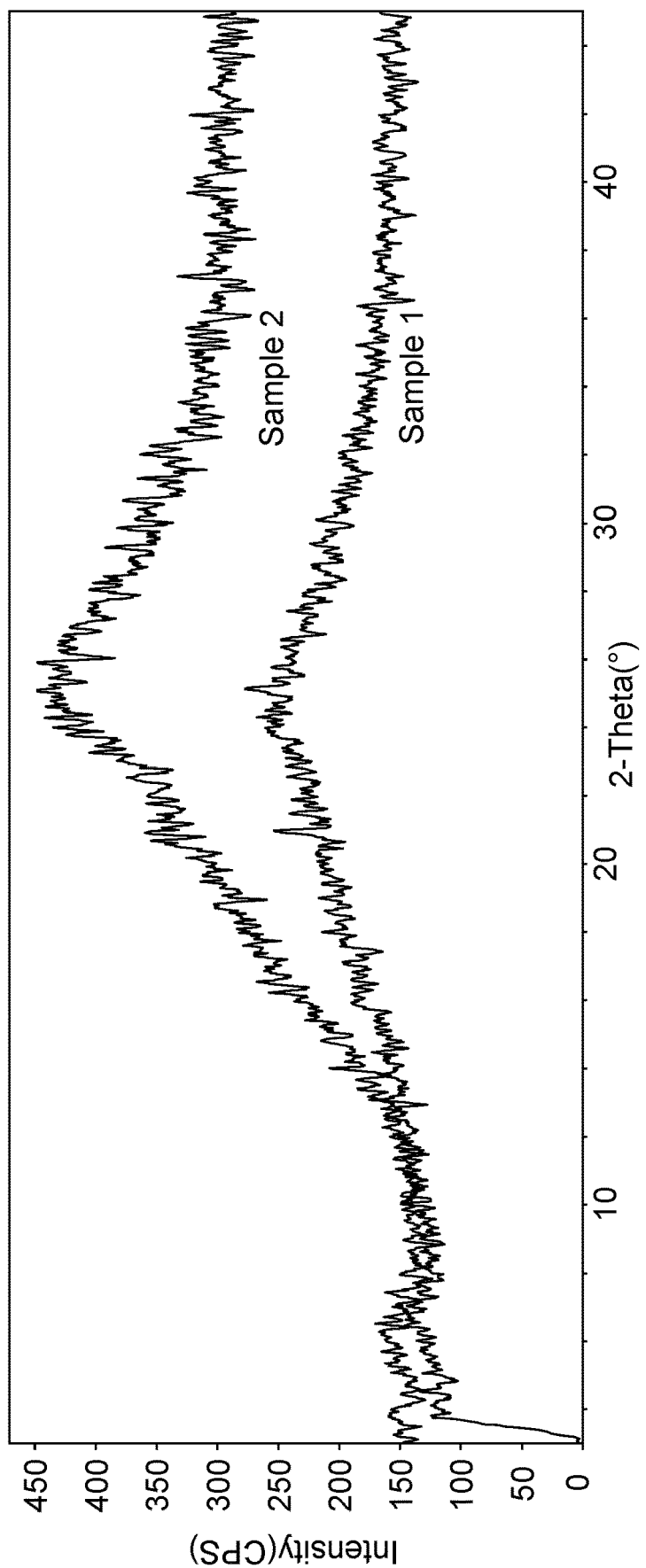
FIG. 8 shows an XRPD pattern of two samples of Compound 1 di-hydrobromic acid salt.
Figure 9:
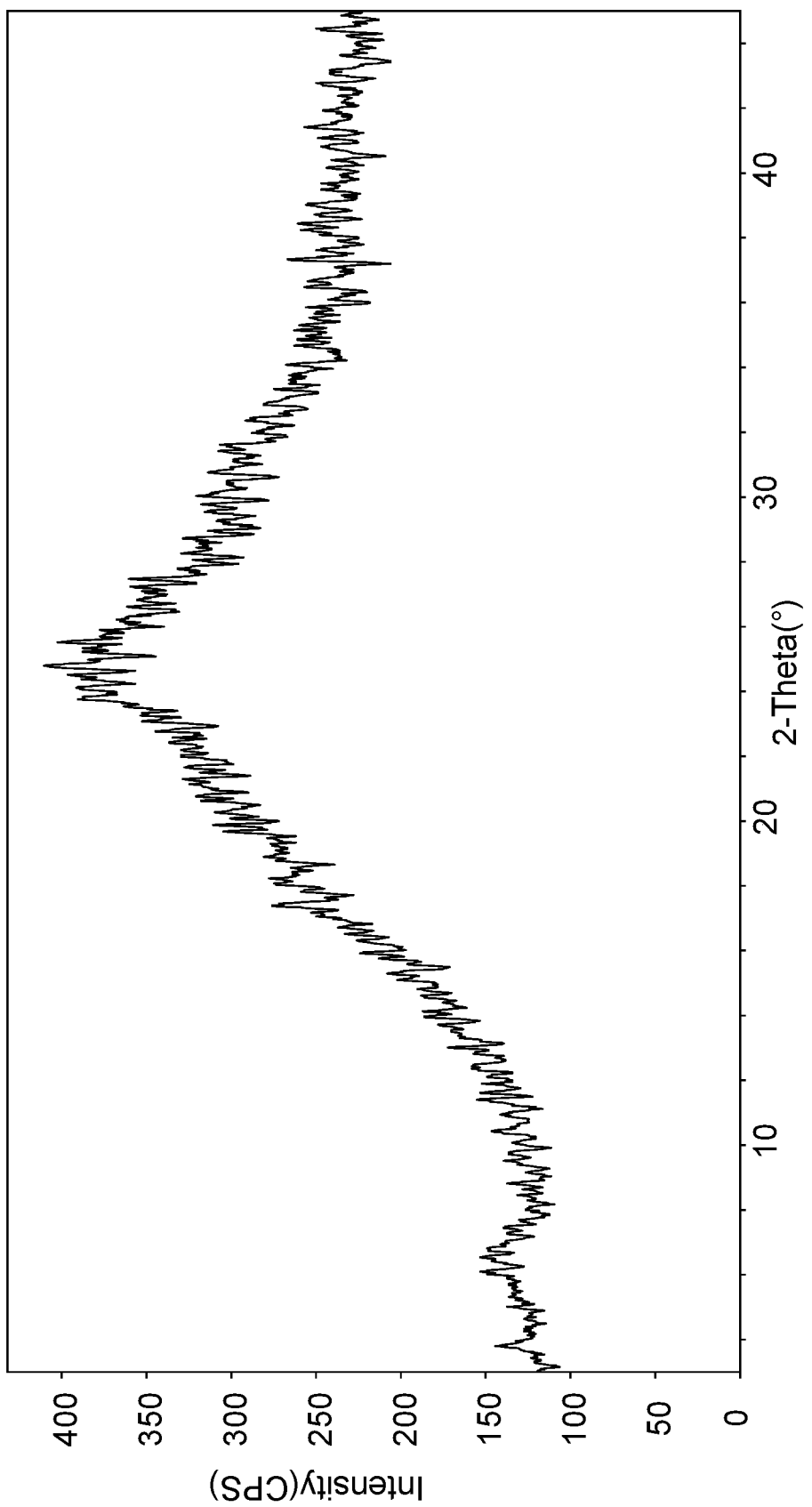
FIG. 9 shows an XRPD pattern of Compound 1 di-hydrobromic acid salt prepared by an alternative method.

In some embodiments, Compound 1 di-hydrobromic acid salt can be characterized by the X-ray powder diffraction (XRPD) pattern substantially as shown in FIG. 8. In some embodiments, Compound 1 di-hydrobromic acid salt can be characterized by the X-ray powder diffraction (XRPD) pattern substantially as shown in FIG. 9.

In some embodiments, Compound 1 di-hydrobromic acid salt is amorphous.

Oxalic Acid Salts

In some embodiments, the salt of Compound 1 is (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid oxalic acid salt (Compound 1 oxalic acid salt). In some embodiments, the Compound 1 oxalic acid salt is (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid mono-oxalic acid salt (Compound 1 mono-oxalic acid salt). In some embodiments, the Compound 1 oxalic acid salt is (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid di-oxalic acid salt (Compound 1 di-oxalic acid salt).

Compound 1 mono-oxalic acid salt can be prepared by any suitable method for preparation of oxalic acid addition salts. For example, Compound 1 can be combined with oxalic acid (e.g., about 1.0 molar eq. or more) in a solvent and the resulting salt can be isolated by filtering the salt from solution. In certain embodiments, Compound 1 is combined with about 1 to about 2 molar equivalents of oxalic acid. In certain embodiments, Compound 1 is combined with about 1.0 to about 1.5 molar equivalents of oxalic acid. In certain embodiments, Compound 1 is combined with about 1.05 molar equivalents of oxalic acid. In certain embodiments, Compound 1 is combined with about 1.1 molar equivalents of oxalic acid.

The solvent can contain any solvent or mixture of solvents capable of at least partially dissolving Compound 1. In some embodiments, the solvent contains an alcohol. Suitable alcohols include methanol, ethanol, 2-nitroethanol, 2-fluoroethanol, 2,2,2-trifluoroethanol, ethylene glycol, 1-propanol, isopropanol (isopropyl alcohol, 2-propanol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol. In some embodiments, the solvent contains acetone, tetrahydrofuran, dichloromethane, methanol, ethanol, 1-propanol, or isopropanol. In some embodiments, the solvent contains acetone.

In some embodiments, the solvent is tetrahydrofuran. In some embodiments, the solvent is a mixture of acetone, methanol and dichloromethane.

In some embodiments, the solvent is about room temperature. In some embodiments, the solvent is heated to a temperature of about 50° C. In some embodiments, the temperature is from about 50° C. to about 80° C. In some embodiments, the temperature is from about 40° C. to about 60° C. In some embodiments, the temperature is from about 45° C. to about 55° C. In some embodiments, the temperature is about 45° C., about 50° C., about 55° C., about 60° C., about 65° C., about 70° C., about 75° C. or about 80° C.

In some embodiments, the solvent is heated to a temperature that can induce precipitation at a practical rate. In some embodiments, precipitation is completed within about 12 to about 24 hours, but longer and shorter periods are possible depending on the choice of precipitation solvent and temperature. In some embodiments, the precipitation is completed within about 2 hours. In some embodiments, the precipitation is completed within about 90 minutes.

The precipitation of the mono-oxalic acid salt, in some embodiments, is carried out by filtering the salt from solution.

Figure 3:
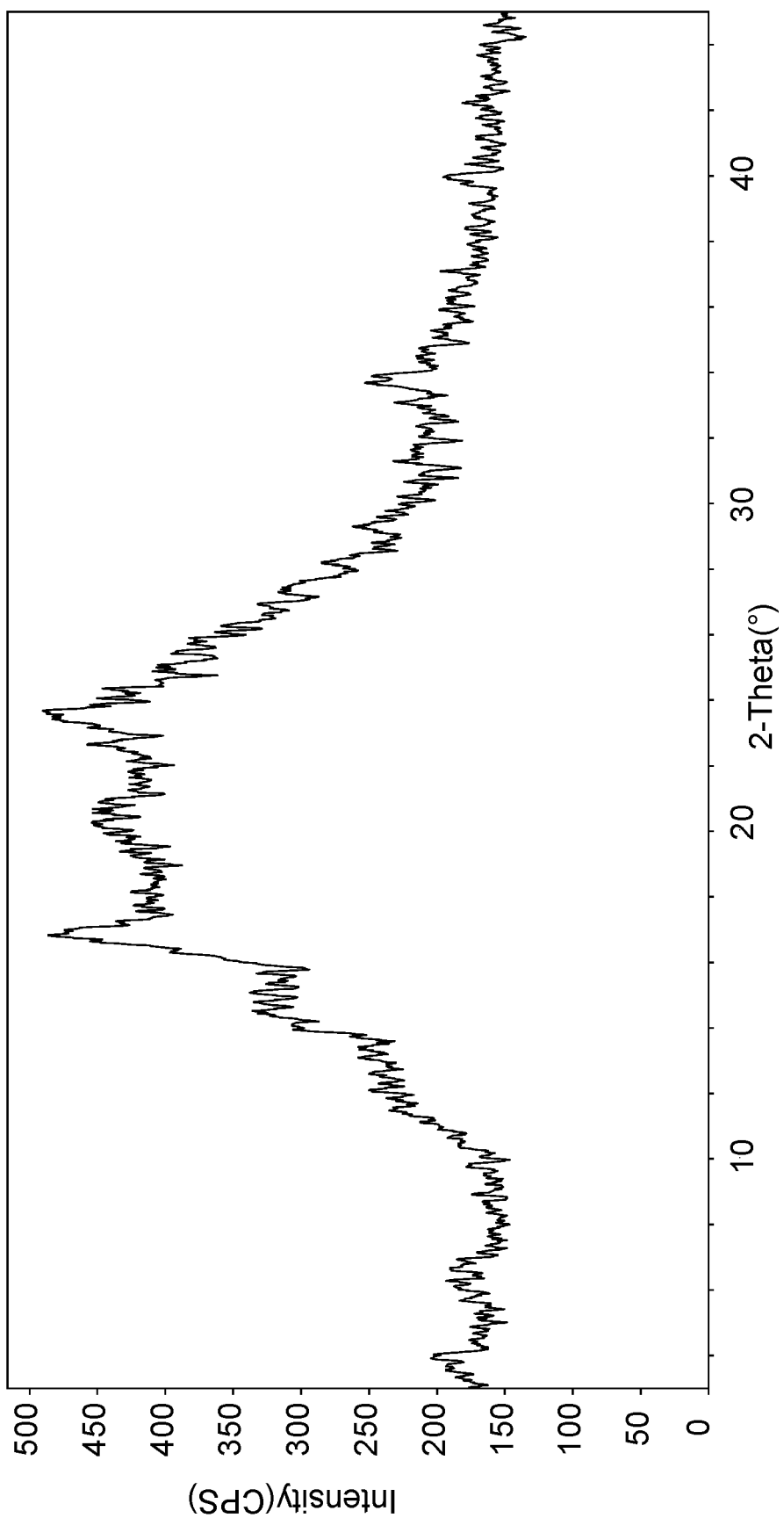
FIG. 3 shows an XRPD pattern of Compound 1 mono-oxalic acid salt.
Figure 4:
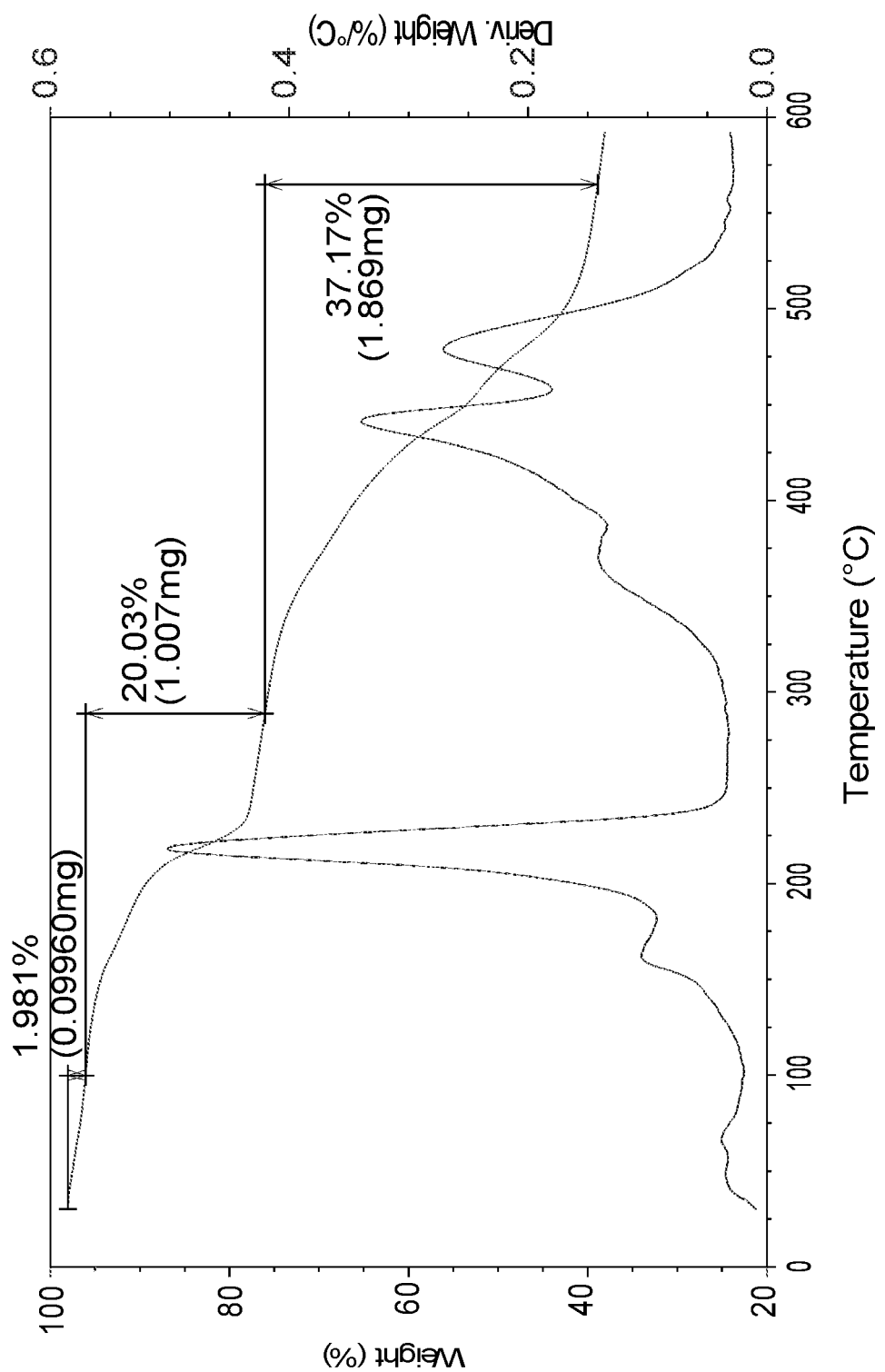
FIG. 4 shows a TGA thermogram of Compound 1 mono-oxalic acid salt.

In some embodiments, Compound 1 mono-oxalic acid salt can be characterized by the X-ray powder diffraction (XRPD) pattern substantially as shown in FIG. 3. In some embodiments, Compound 1 mono-oxalic acid salt can be characterized by the thermogravimetric analysis (TGA) spectrum substantially as shown in FIG. 4.

In some embodiments, Compound 1 mono-oxalic acid salt is amorphous.

Compound 1 di-oxalic acid salt can be prepared by any suitable method for preparation of oxalic acid addition salts. For example, Compound 1 can be combined with oxalic acid (e.g., about 2.0 molar eq. or more) in a solvent and the resulting salt can be isolated by filtering the salt from solution. In certain embodiments, Compound 1 is combined with about 2 to about 3 molar equivalents of oxalic acid. In certain embodiments, Compound 1 is combined with about 2.0 to about 2.5 molar equivalents of oxalic acid. In certain embodiments, Compound 1 is combined with about 2.05 molar equivalents of oxalic acid.

The solvent can contain any solvent or mixture of solvents capable of at least partially dissolving Compound 1. In some embodiments, the solvent contains an alcohol. Suitable alcohols include methanol, ethanol, 2-nitroethanol, 2-fluoroethanol, 2,2,2-trifluoroethanol, ethylene glycol, 1-propanol, isopropanol (isopropyl alcohol, 2-propanol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol. In some embodiments, the solvent contains acetone, tetrahydrofuran, dichloromethane, methanol, ethanol, 1-propanol, or isopropanol. In some embodiments, the solvent contains dichloromethane.

In some embodiments, the solvent is tetrahydrofuran.

In some embodiments, the solvent is about room temperature. In some embodiments, the solvent is heated to a temperature of about 50° C. In some embodiments, the temperature is from about 50° C. to about 80° C. In some embodiments, the temperature is from about 40° C. to about 60° C. In some embodiments, the temperature is from about 45° C. to about 55° C. In some embodiments, the temperature is about 45° C., about 50° C., about 55° C., about 60° C., about 65° C., about 70° C., about 75° C. or about 80° C.

In some embodiments, the solvent is heated to a temperature that can induce precipitation and/or crystallization at a practical rate. In some embodiments, precipitation and/or crystallization is completed within about 12 to about 24 hours, but longer and shorter periods are possible depending on the choice of precipitation/crystallizing solvent and temperature. In some embodiments, the precipitation and/or crystallization is completed within about 2 hours.

The precipitation and/or crystallization of the di-oxalic acid salt, in some embodiments, is carried out by filtering the salt from solution.

Figure 10:
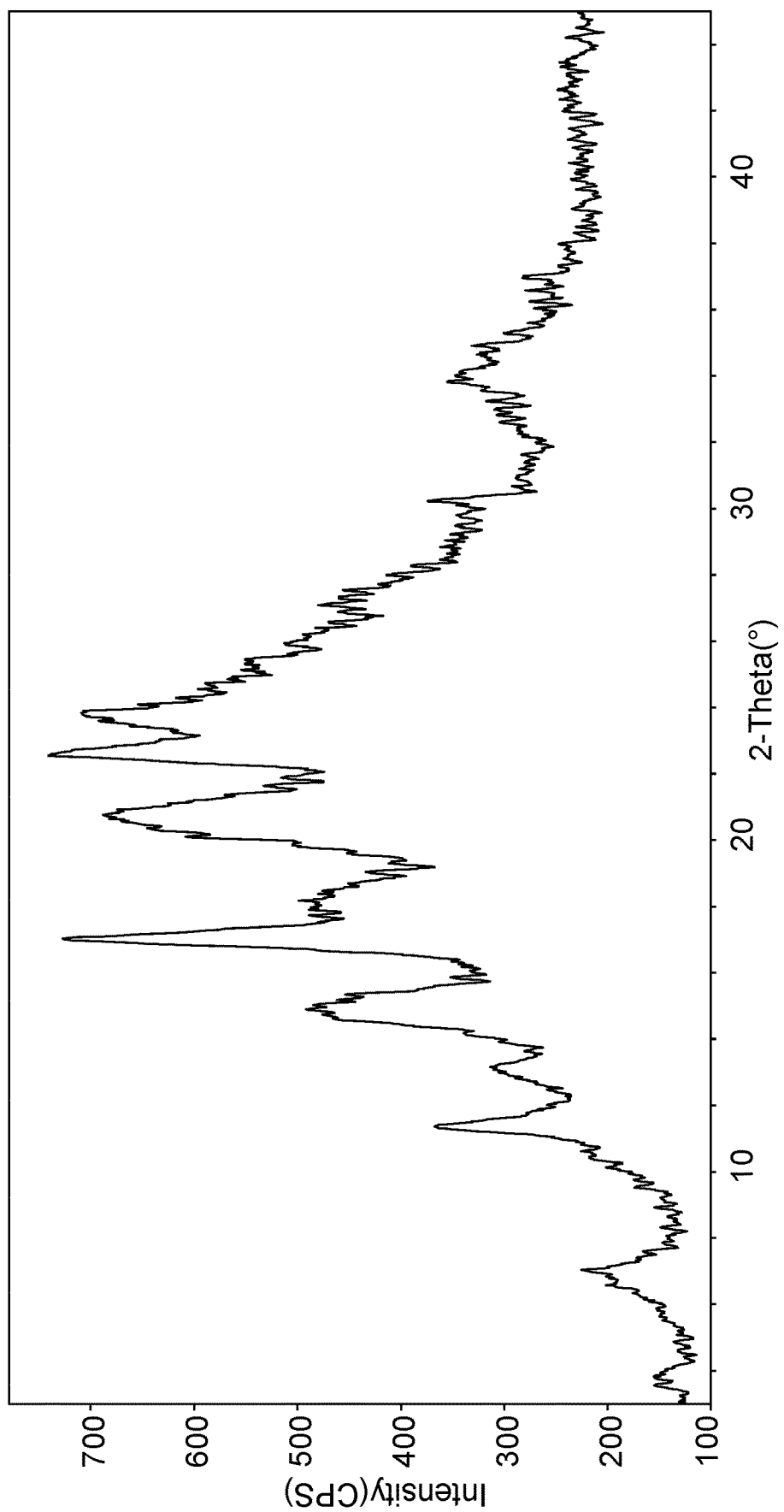
FIG. 10 shows an XRPD pattern of Compound 1 di-oxalic acid salt.

In some embodiments, Compound 1 di-oxalic acid salt can be characterized by the X-ray powder diffraction (XRPD) pattern substantially as shown in FIG. 10.

In some embodiments, Compound 1 di-oxalic acid salt has a characteristic X-ray powder diffraction (XRPD) peak at 7.0±0.2 degrees 2-theta. In some embodiments, Compound 1 di-oxalic acid salt has a characteristic X-ray powder diffraction (XRPD) peak at 11.4±0.2 degrees 2-theta. In some embodiments, Compound 1 di-oxalic acid salt has a characteristic X-ray powder diffraction (XRPD) peak at 13.2±0.2 degrees 2-theta. In some embodiments, Compound 1 di-oxalic acid salt has a characteristic X-ray powder diffraction (XRPD) peak at 14.9±0.2 degrees 2-theta. In some embodiments, Compound 1 di-oxalic acid salt has a characteristic X-ray powder diffraction (XRPD) peak at 17.0±0.2 degrees 2-theta.

In some embodiments, the di-oxalic acid salt of Compound 1 has characteristic X-ray powder diffraction (XRPD) peaks at 7.0±0.2, 11.4±0.2, and 14.9±0.2 degrees 2-theta. In some embodiments, the di-oxalic acid salt of Compound 1 has characteristic X-ray powder diffraction (XRPD) peaks at 7.0±0.2, 11.4±0.2, 14.9±0.2, and 17.0±0.2 degrees 2-theta. In some embodiments, the di-oxalic acid salt of Compound 1 has characteristic X-ray powder diffraction (XRPD) peaks at 7.0±0.2, 11.4±0.2, 13.2±0.2, 14.9±0.2, and 17.0±0.2 degrees 2-theta.

In some embodiments, Compound 1 di-oxalic acid salt has at least one X-ray powder diffraction (XRPD) peak selected from 7.0±0.2, 11.4±0.2, 13.2±0.2, 14.9±0.2, and 17.0±0.2 degrees 2-theta. In some embodiments, Compound 1 di-oxalic acid salt has at least two X-ray powder diffraction (XRPD) peaks selected from 7.0±0.2, 11.4±0.2, 13.2±0.2, 14.9±0.2, and 17.0±0.2 degrees 2-theta. In some embodiments, Compound 1 di-oxalic acid salt has at least three X-ray powder diffraction (XRPD) peaks selected from 7.0±0.2, 11.4±0.2, 13.2±0.2, 14.9±0.2, and 17.0±0.2 degrees 2-theta. In some embodiments, Compound 1 di-oxalic acid salt has at least four X-ray powder diffraction (XRPD) peaks selected from 7.0±0.2, 11.4±0.2, 13.2±0.2, 14.9±0.2, and 17.0±0.2 degrees 2-theta.

Figure 11:
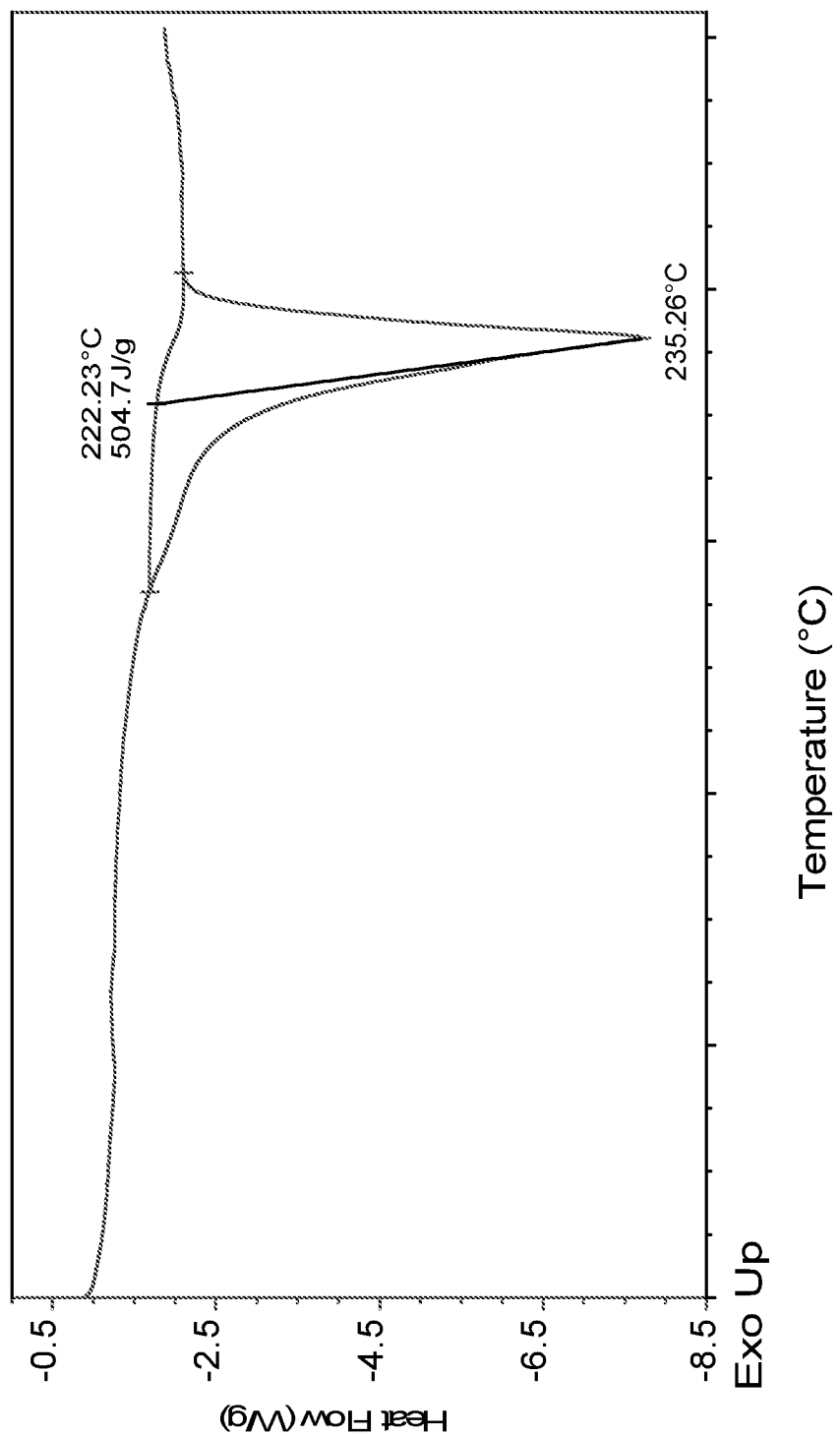
FIG. 11 shows a DSC thermogram of Compound 1 di-oxalic acid salt.
Figure 12:
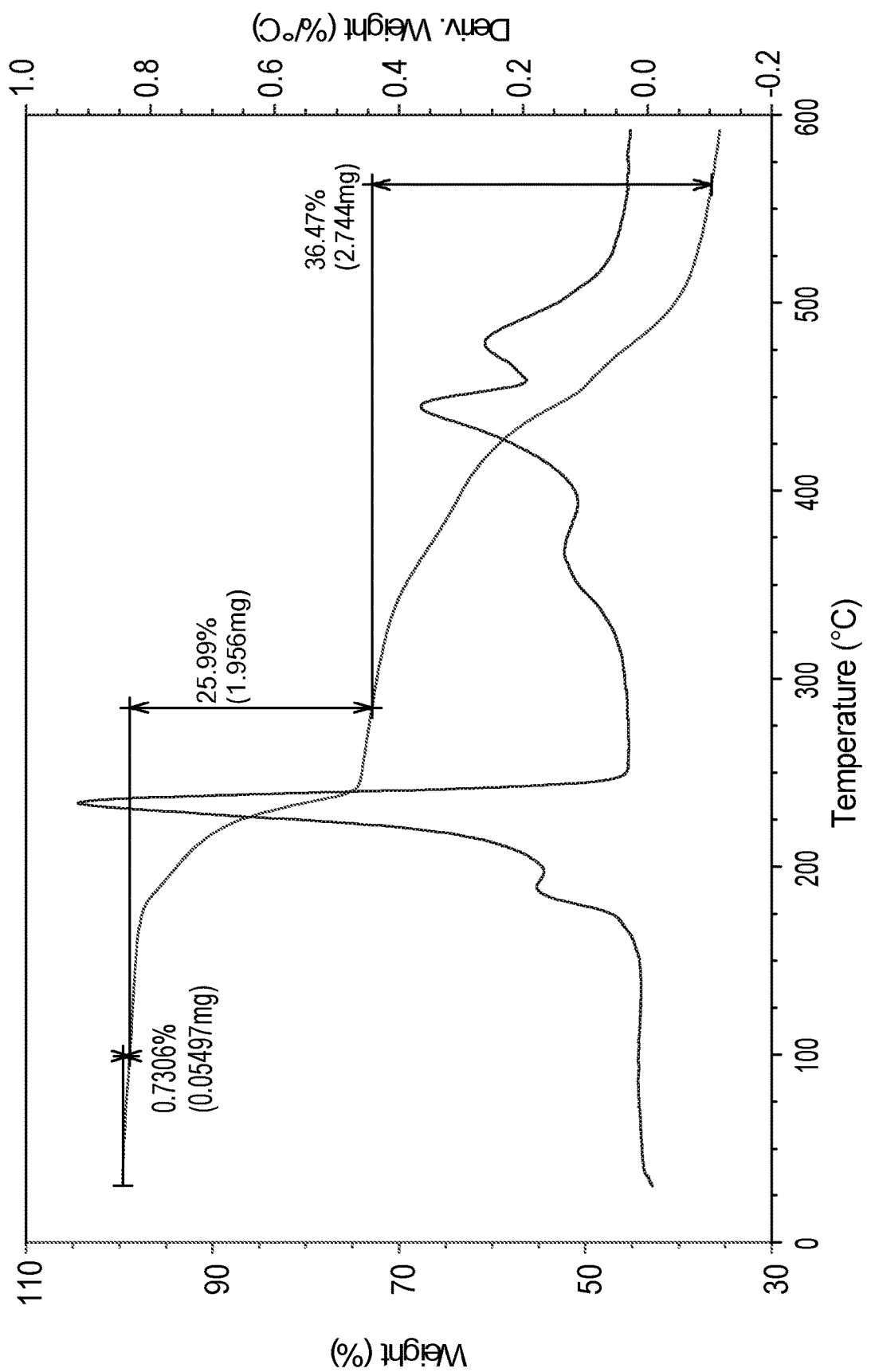
FIG. 12 shows a TGA thermogram of Compound 1 di-oxalic acid salt.

In some embodiments, Compound 1 di-oxalic acid salt exhibits a DSC thermogram having an endothermic peak at a temperature of 235±3° C. In some embodiments, the di-oxalic acid salt of Compound 1 has a DSC thermogram substantially as depicted in FIG. 11. In some embodiments, the di-oxalic acid salt of Compound 1 has a TGA thermogram substantially as depicted in FIG. 12.

In some embodiments, Compound 1 di-oxalic acid salt has at least one characteristic XRPD peak selected from 7.0±0.2, 11.4±0.2, 13.2±0.2, 14.9±0.2, and 17.0±0.2 degrees 2-theta; and the di-oxalic acid salt of Compound 1 exhibits a DSC thermogram having an endothermic peak at a temperature of 235±3° C.

In some embodiments, Compound 1 di-oxalic acid salt is amorphous. In some embodiments, Compound 1 di-oxalic acid salt is crystalline. In some embodiments, Compound 1 di-oxalic acid salt is a mixture comprising crystalline and amorphous forms.

Hydrochloric Acid Salts

In some embodiments, the salt of Compound 1 is (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid hydrochloric acid salt (Compound 1 hydrochloric acid salt).

In some embodiments, the Compound 1 hydrochloric acid salt is (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid mono-hydrochloric acid salt (Compound 1 mono-hydrochloric acid salt). In some embodiments, the Compound 1 hydrochloric acid salt is (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid tri-hydrochloric acid salt (Compound 1 tri-hydrochloric acid salt).

Compound 1 mono-hydrochloric acid salt can be prepared by any suitable method for preparation of mono-hydrochloric acid addition salts. For example, Compound 1 can be combined with hydrochloric acid (e.g., about 1.0 molar eq. or more) in a solvent and the resulting salt can be isolated by filtering the salt from solution. In certain embodiments, Compound 1 is combined with about 1 to about 2 molar equivalents of hydrochloric acid. In certain embodiments, Compound 1 is combined with about 1 to about 1.5 molar equivalents of hydrochloric acid. In certain embodiments, Compound 1 is combined with about 1.05 molar equivalents of hydrochloric acid.

The solvent can contain any solvent or mixture of solvents capable of at least partially dissolving Compound 1. In some embodiments, the solvent contains an alcohol. Suitable alcohols include methanol, ethanol, 2-nitroethanol, 2-fluoroethanol, 2,2,2-trifluoroethanol, ethylene glycol, 1-propanol, isopropanol (isopropyl alcohol, 2-propanol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol. In some embodiments, the solvent contains acetone, tetrahydrofuran, dichloromethane, methanol, ethanol, 1-propanol, or isopropanol. In some embodiments, the solvent contains dichloromethane. In some embodiments, the solvent contains methanol.

In some embodiments, the solvent is a mixture of isopropanol, water, methanol and dichloromethane. In some embodiments, the solvent is a mixture of isopropanol, water and methanol.

In some embodiments, the solvent is about room temperature. In some embodiments, the solvent is heated to a temperature of about 50° C. In some embodiments, the temperature is from about 50° C. to about 80° C. In some embodiments, the temperature is from about 40° C. to about 60° C. In some embodiments, the temperature is from about 45° C. to about 55° C. In some embodiments, the temperature is about 45° C., about 50° C., about 55° C., about 60° C., about 65° C., about 70° C., about 75° C. or about 80° C.

In some embodiments, the solvent is heated to a temperature that can induce precipitation at a practical rate. In some embodiments, precipitation is completed within about 12 to about 24 hours, but longer and shorter periods are possible depending on the choice of precipitation solvent and temperature. In some embodiments, precipitation is completed within about 12 hours.

The precipitation of the mono-hydrochloric acid salt, in some embodiments, is carried out by filtering the salt from solution.

Figure 5:
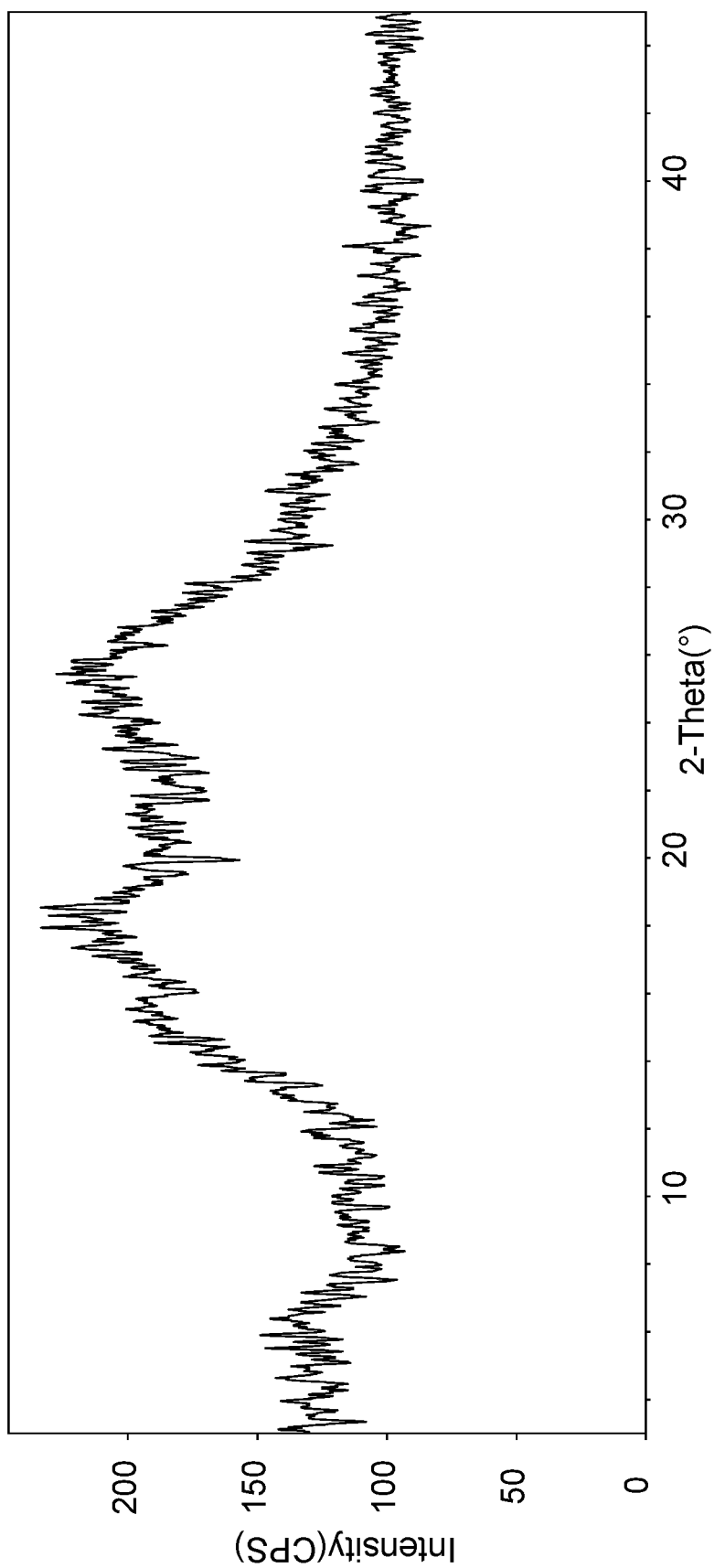
FIG. 5 shows an XRPD pattern of Compound 1 mono-hydrochloric acid salt.

In some embodiments, Compound 1 mono-hydrochloric acid salt can be characterized by the X-ray powder diffraction (XRPD) pattern substantially as shown in FIG. 5.

In some embodiments, Compound 1 mono-hydrochloric acid salt is amorphous.

Compound 1 tri-hydrochloric acid salt can be prepared by any suitable method for preparation of tri-hydrochloric acid addition salts. For example, Compound 1 can be combined with hydrochloric acid (e.g., about 3.0 molar eq. or more) in a solvent and the resulting salt can be isolated by filtering the salt from solution. In certain embodiments, Compound 1 is combined with about 3 to about 5 molar equivalents of hydrochloric acid. In certain embodiments, Compound 1 is combined with about 3 to about 4 molar equivalents of hydrochloric acid. In certain embodiments, Compound 1 is combined with about 4 molar equivalents of hydrochloric acid.

The solvent can contain any solvent or mixture of solvents capable of at least partially dissolving Compound 1. In some embodiments, the solvent contains an alcohol. Suitable alcohols include methanol, ethanol, 2-nitroethanol, 2-fluoroethanol, 2,2,2-trifluoroethanol, ethylene glycol, 1-propanol, isopropanol (isopropyl alcohol, 2-propanol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol. In some embodiments, the solvent contains dioxane, dimethylsulfoxide, acetone, tetrahydrofuran, dichloromethane, methanol, ethanol, 1-propanol, or isopropanol. In some embodiments, the solvent contains tetrahydrofuran.

In some embodiments, the solvent is a mixture of dimethylsulfoxide, tetrahydrofuran and dioxane.

In some embodiments, the solvent is about room temperature. In some embodiments, the solvent is heated to a temperature of about 50° C. In some embodiments, the temperature is from about 50° C. to about 80° C. In some embodiments, the temperature is from about 40° C. to about 60° C. In some embodiments, the temperature is from about 45° C. to about 55° C. In some embodiments, the temperature is about 45° C., about 50° C., about 55° C., about 60° C., about 65° C., about 70° C., about 75° C. or about 80° C.

In some embodiments, the solvent is heated to a temperature that can induce precipitation at a practical rate. In some embodiments, precipitation is completed within about 12 to about 24 hours, but longer and shorter periods are possible depending on the choice of precipitation solvent and temperature. In some embodiments, precipitation is completed within about 12 hours.

The precipitation of the tri-hydrochloric acid salt, in some embodiments, is carried out by filtering the salt from solution.

In some embodiments, Compound 1 tri-hydrochloric acid salt is amorphous.

L-Tartaric Acid Salts

In some embodiments, the salt of Compound 1 is (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid L-tartaric acid salt (Compound 1 L-tartaric acid salt). In some embodiments, the Compound 1 L-tartaric acid salt is (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid L-tartaric acid salt (1:1.5) (Compound 1 L-tartaric acid salt (1:1.5)), wherein the ratio of Compound 1 to L-tartaric acid is about 1 to 1.5. In some embodiments, the Compound 1 L-tartaric acid salt is (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid L-tartaric acid salt (1:1.7) (Compound 1 L-tartaric acid salt (1:1.7)), wherein the ratio of Compound 1 to L-tartaric acid is about 1 to 1.7.

Compound 1 L-tartaric acid salt (1:1.5) can be prepared by any suitable method for preparation of L-tartaric acid addition salts. For example, Compound 1 can be combined with L-tartaric acid in a solvent and the resulting salt can be isolated by filtering the salt from solution. In certain embodiments, Compound 1 is combined with about 0.8 to about 2.5 molar equivalents of L-tartaric acid. In certain embodiments, Compound 1 is combined with about 1.5 to about 2.5 molar equivalents of L-tartaric acid. In certain embodiments, Compound 1 is combined with about 1.9 to about 2.1 molar equivalents of L-tartaric acid. In certain embodiments, Compound 1 is combined with about 1.8 to about 2.2 molar equivalents of L-tartaric acid. In certain embodiments, Compound 1 is combined with about 0.9 to about 1.1 molar equivalents of L-tartaric acid. In certain embodiments, Compound 1 is combined with about 0.8 to about 1.2 molar equivalents of L-tartaric acid. In certain embodiments, Compound 1 is combined with about 0.5 to about 1.5 molar equivalents of L-tartaric acid. In certain embodiments, Compound 1 is combined with about 1.5 to about 2.0 molar equivalents of L-tartaric acid. In certain embodiments, Compound 1 is combined with about 1.5 molar equivalents of L-tartaric acid. In certain embodiments, Compound 1 is combined with about 1.05 molar equivalents of L-tartaric acid. In certain embodiments, Compound 1 is combined with about 2.05 molar equivalents of L-tartaric acid.

The solvent can contain any solvent or mixture of solvents capable of at least partially dissolving Compound 1. In some embodiments, the solvent contains an alcohol. Suitable alcohols include methanol, ethanol, 2-nitroethanol, 2-fluoroethanol, 2,2,2-trifluoroethanol, ethylene glycol, 1-propanol, isopropanol (isopropyl alcohol, 2-propanol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol. In some embodiments, the solvent contains acetone, tetrahydrofuran, dichloromethane, methanol, ethanol, 1-propanol, or isopropanol. In some embodiments, the solvent contains dichloromethane.

In some embodiments, the solvent is tetrahydrofuran.

In some embodiments, the solvent is about room temperature. In some embodiments, the solvent is heated to a temperature of at least about 50° C. In some embodiments, the temperature is from about 50° C. to about 80° C. In some embodiments, the temperature is from about 40° C. to about 60° C. In some embodiments, the temperature is from about 45° C. to about 55° C. In some embodiments, the temperature is about 45° C., about 50° C., about 55° C., about 60° C., about 65° C., about 70° C., about 75° C. or about 80° C.

In some embodiments, the solvent is heated to a temperature that can induce precipitation at a practical rate. In some embodiments, precipitation is completed within about 12 to about 24 hours, but longer and shorter periods are possible depending on the choice of precipitation solvent and temperature. In some embodiments, precipitation is completed within about 2 hours.

The precipitation of the L-tartaric acid salt (1:1.5), in some embodiments, is carried out by filtering the salt from solution.

Figure 6:
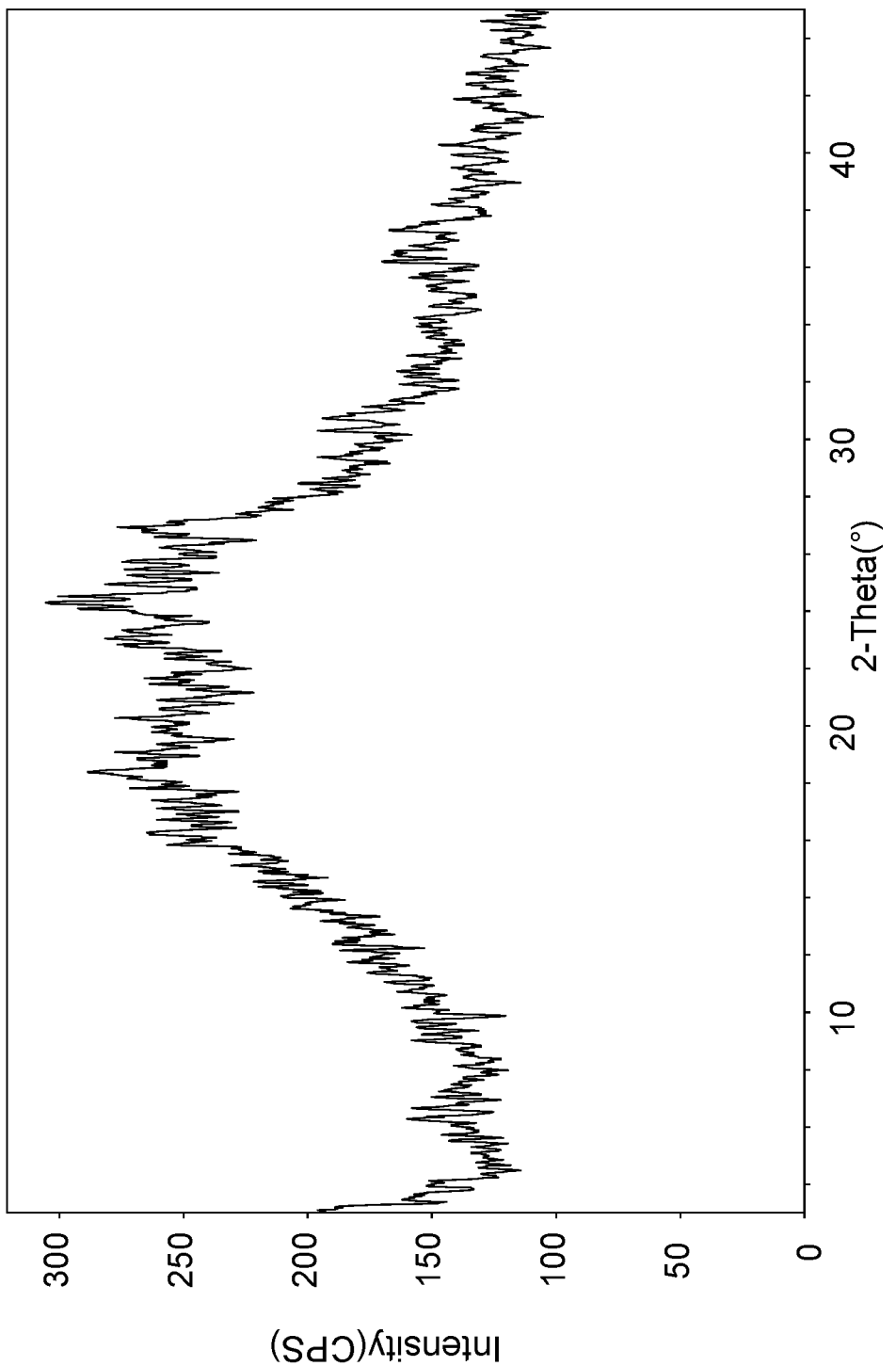
FIG. 6 shows an XRPD pattern of Compound 1 L-tartaric acid salt (1:1.5).
Figure 7:
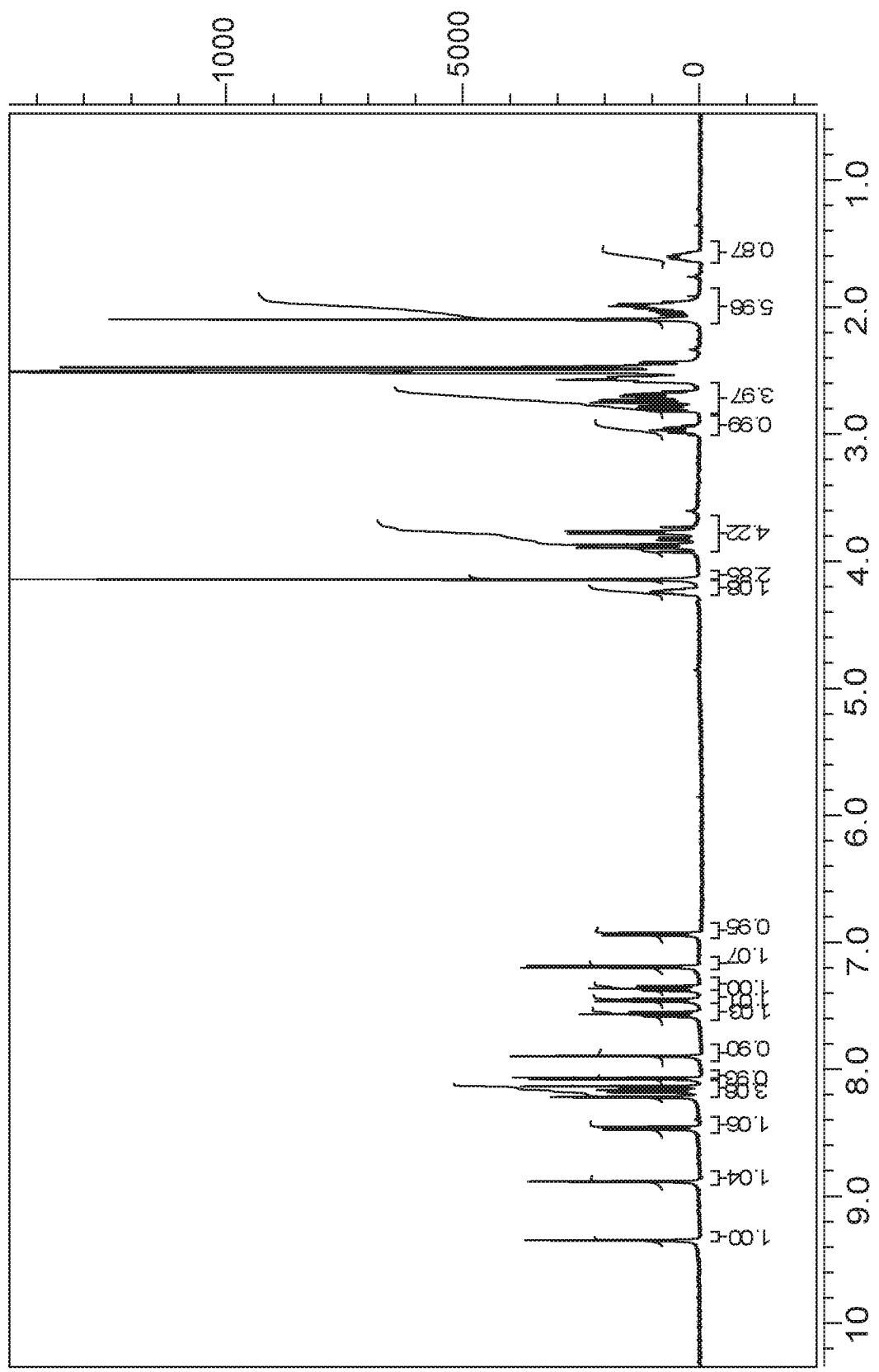
FIG. 7 shows a $^1$H NMR of Compound 1 L-tartaric acid salt (1:1.5).

In some embodiments, Compound 1 L-tartaric acid salt (1:1.5) can be characterized by the X-ray powder diffraction (XRPD) pattern substantially as shown in FIG. 6. In some embodiments, Compound 1 L-tartaric acid salt (1:1.5) can be characterized by the $^1$H NMR spectrum substantially as depicted in FIG. 7.

In some embodiments, Compound 1 L-tartaric acid salt (1:1.5) is amorphous.

Compound 1 L-tartaric acid salt (1:1.7) can be prepared by any suitable method for preparation of L-tartaric acid addition salts. For example, Compound 1 can be combined with L-tartaric acid (e.g., about 1.7 molar eq. or more) in a solvent and the resulting salt can be isolated by filtering the salt from solution. In certain embodiments, Compound 1 is combined with about 1.7 to about 3 molar equivalents of L-tartaric acid. In certain embodiments, Compound 1 is combined with about 1.7 to about 2.5 equivalents of molar L-tartaric acid. In certain embodiments, Compound 1 is combined with about 2.05 molar equivalents of L-tartaric acid. In certain embodiments, Compound 1 is combined with about 1.7 molar equivalents of L-tartaric acid.

The solvent can contain any solvent or mixture of solvents capable of at least partially dissolving Compound 1. In some embodiments, the solvent contains an alcohol. Suitable alcohols include methanol, ethanol, 2-nitroethanol, 2-fluoroethanol, 2,2,2-trifluoroethanol, ethylene glycol, 1-propanol, isopropanol (isopropyl alcohol, 2-propanol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol. In some embodiments, the solvent contains acetone, tetrahydrofuran, dichloromethane, methanol, ethanol, 1-propanol, or isopropanol. In some embodiments, the solvent contains dichloromethane.

In some embodiments, the solvent is tetrahydrofuran.

In some embodiments, the solvent is about room temperature. In some embodiments, the solvent is heated to a temperature of at least about 50° C. In some embodiments, the temperature is from about 50° C. to about 80° C. In some embodiments, the temperature is from about 40° C. to about 60° C. In some embodiments, the temperature is from about 45° C. to about 55° C. In some embodiments, the temperature is about 45° C., about 50° C., about 55° C., about 60° C., about 65° C., about 70° C., about 75° C. or about 80° C.

In some embodiments, the solvent is heated to a temperature that can induce precipitation at a practical rate. In some embodiments, precipitation is completed within about 12 to about 24 hours, but longer and shorter periods are possible depending on the choice of precipitation solvent and temperature. In some embodiments, precipitation is completed within about 2 hours.

The precipitation of the L-tartaric acid salt (1:1.7), in some embodiments, is carried out by filtering the salt from solution.

Figure 13:
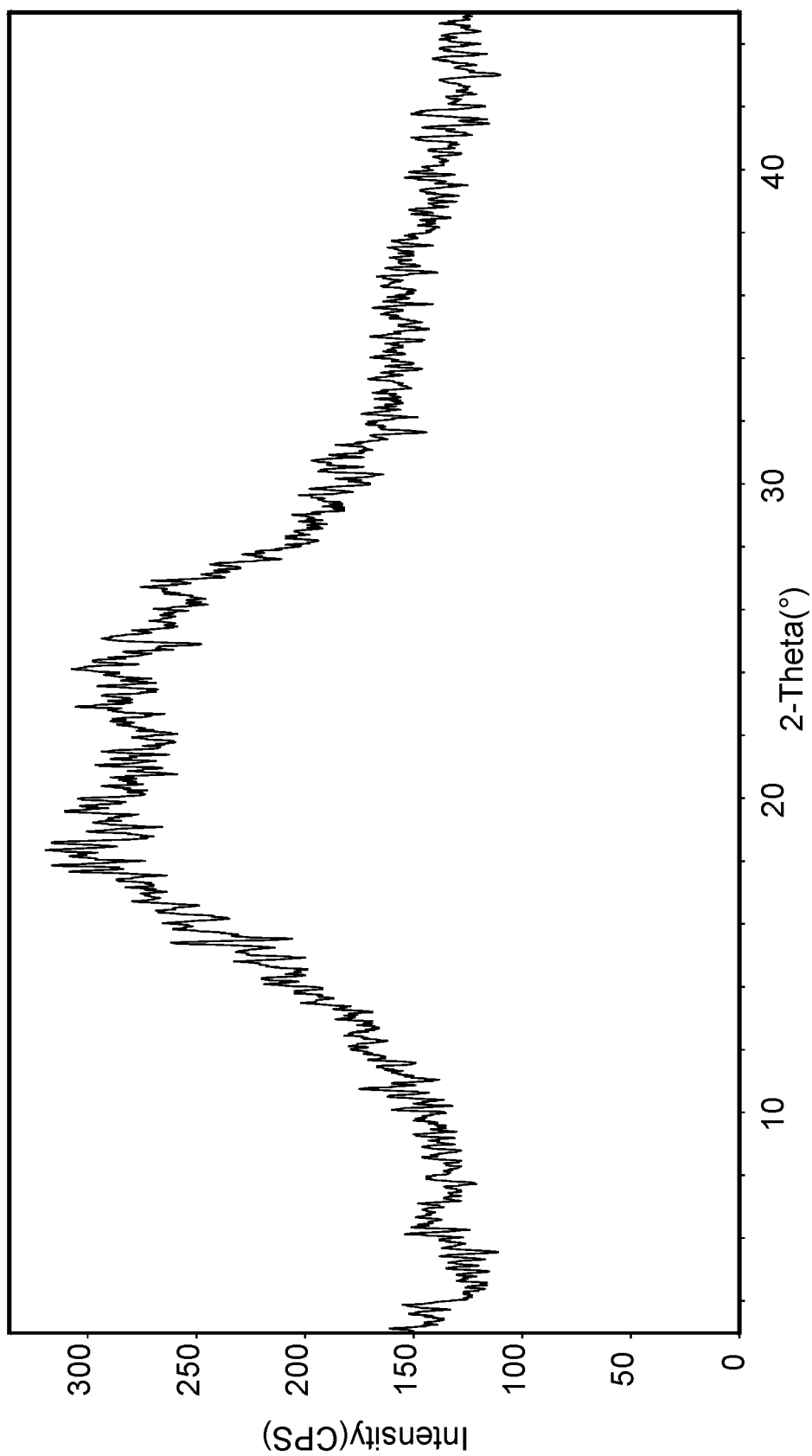
FIG. 13 shows an XRPD pattern of Compound 1 L-tartaric acid salt (1:1.7).
Figure 14:
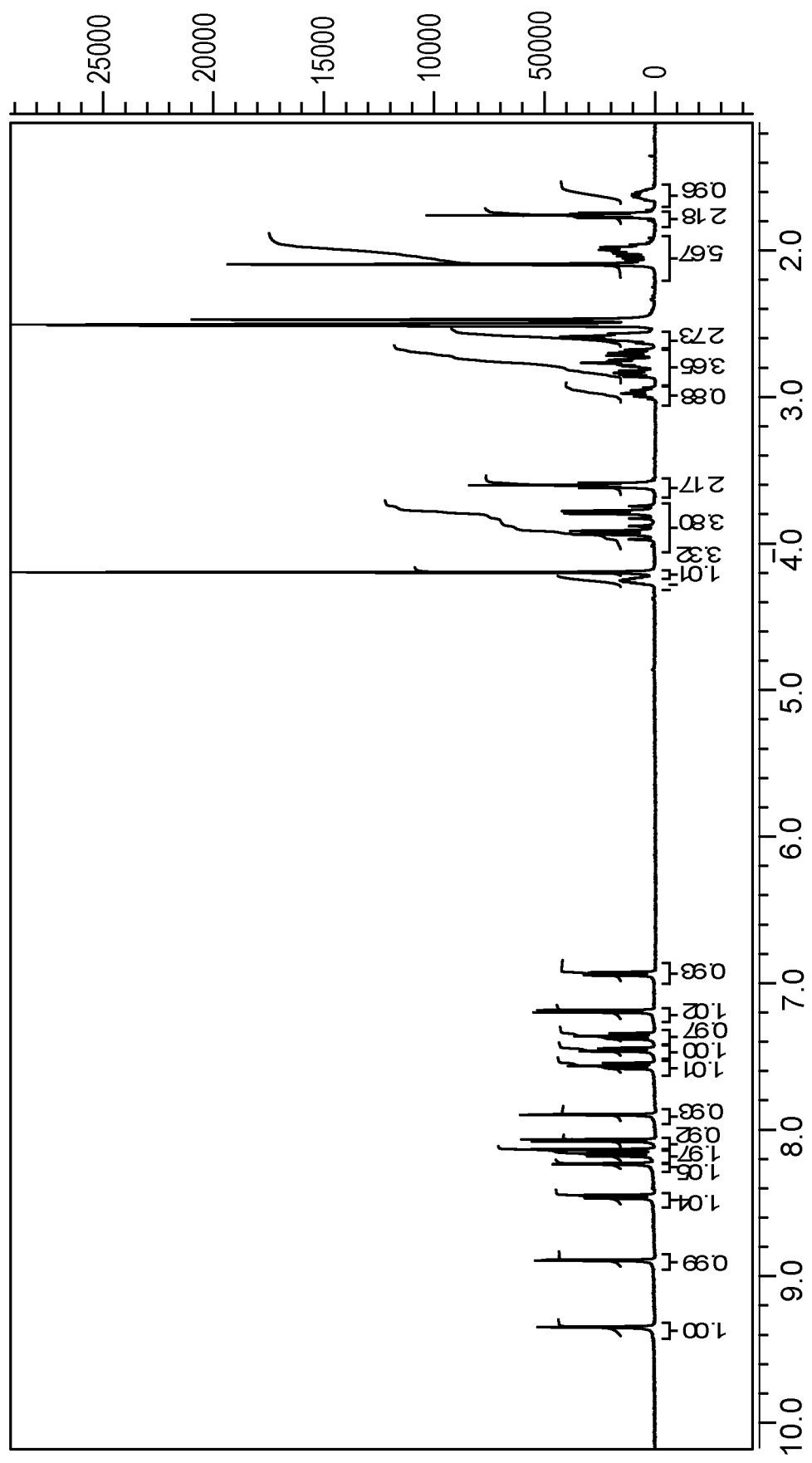
FIG. 14 shows a $^1$H NMR of Compound 1 L-tartaric acid salt (1:1.7).

In some embodiments, Compound 1 L-tartaric acid salt (1:1.7) can be characterized by the X-ray powder diffraction (XRPD) pattern substantially as shown in FIG. 13. In some embodiments, Compound 1 L-tartaric acid salt (1:1.7) can be characterized by the $^1$H NMR spectrum substantially as depicted in FIG. 14.

In some embodiments, Compound 1 L-tartaric acid salt (1:1.7) is amorphous.

Malonic Acid Salts

In some embodiments, the salt of Compound 1 is (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid malonic acid salt (Compound 1 malonic acid salt). In some embodiments, the Compound 1 malonic acid salt is (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid mono-malonic acid salt (Compound 1 mono-malonic acid salt).

Compound 1 mono-malonic acid salt can be prepared by any suitable method for preparation of mono-malonic acid addition salts. For example, Compound 1 can be combined with malonic acid (e.g., about 1.0 molar eq. or more) in a solvent and the resulting salt can be isolated by filtering the salt from solution. In certain embodiments, Compound 1 is combined with about 1 to about 2 molar equivalents of malonic acid. In certain embodiments, Compound 1 is combined with about 1 to about 1.5 molar equivalents of malonic acid. In certain embodiments, Compound 1 is combined with about 1.1 molar equivalents of malonic acid.

The solvent can contain any solvent or mixture of solvents capable of at least partially dissolving Compound 1. In some embodiments, the solvent contains an alcohol. Suitable alcohols include methanol, ethanol, 2-nitroethanol, 2-fluoroethanol, 2,2,2-trifluoroethanol, ethylene glycol, 1-propanol, isopropanol (isopropyl alcohol, 2-propanol), 2-methoxyethanol, 1-butanol, 2-butanol, 1-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol. In some embodiments, the solvent contains acetone, tetrahydrofuran, dichloromethane, methanol, ethanol, 1-propanol, or isopropanol. In some embodiments, the solvent contains dichloromethane.

In some embodiments, the solvent is a mixture of acetone, methanol and dichloromethane.

In some embodiments, the solvent is about room temperature. In some embodiments, the solvent is heated to a temperature of about 50° C. In some embodiments, the temperature is from about 50° C. to about 80° C. In some embodiments, the temperature is from about 40° C. to about 60° C. In some embodiments, the temperature is from about 45° C. to about 55° C. In some embodiments, the temperature is about 45° C., about 50° C., about 55° C., about 60° C., about 65° C., about 70° C., about 75° C. or about 80° C.

In some embodiments, the solvent is heated to a temperature that can induce precipitation at a practical rate. In some embodiments, precipitation is completed within about 12 to about 24 hours, but longer and shorter periods are possible depending on the choice of precipitation solvent and temperature. In some embodiments, precipitation is completed within about 1 to about 2 hours. In some embodiments, precipitation is completed within about 90 minutes.

The precipitation of the mono-malonic acid salt, in some embodiments, is carried out by filtering the salt from solution.

In some embodiments, Compound 1 mono-malonic acid salt is amorphous.

Phosphoric Acid Salts

In some embodiments, the salt of Compound 1 is (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid phosphoric acid salt (Compound 1 phosphoric acid salt). In some embodiments, the Compound 1 phosphoric acid salt is (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid phosphoric acid salt (~1:2) (Compound 1 phosphoric acid salt (~1:2)), wherein the ratio of Compound 1 to phosphoric acid is about 1 to 2. In some embodiments, the Compound 1 phosphoric acid salt is (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid phosphoric acid salt (~1:3) (Compound 1 phosphoric acid salt (~1:3) wherein the ratio of Compound 1 to phosphoric acid is about 1 to 3.

Compound 1 phosphoric acid salt (~1:2) can be prepared by any suitable method for preparation of phosphoric acid (~1:2) addition salts. For example, Compound 1 can be combined with phosphoric acid (e.g., about 2.0 molar eq. or more) in a solvent and the resulting salt can be isolated by filtering the salt from solution. In certain embodiments, Compound 1 is combined with about 2 to about 3 molar equivalents of phosphoric acid. In certain embodiments, Compound 1 is combined with about 2 to about 2.5 molar equivalents of phosphoric acid. In certain embodiments, Compound 1 is combined with about 2 molar equivalents of phosphoric acid.

The solvent can contain any solvent or mixture of solvents capable of at least partially dissolving Compound 1. In some embodiments, the solvent contains an alcohol. Suitable alcohols include methanol, ethanol, 2-nitroethanol, 2-fluoroethanol, 2,2,2-trifluoroethanol, ethylene glycol, 1-propanol, isopropanol (isopropyl alcohol, 2-propanol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol. In some embodiments, the solvent contains acetone, tetrahydrofuran, dichloromethane, methanol, ethanol, 1-propanol, or isopropanol. In some embodiments, the solvent contains dichloromethane. In some embodiments, the solvent contains acetone.

In some embodiments, the solvent is a mixture of acetone, methanol and dichloromethane.

In some embodiments, the solvent is about room temperature. In some embodiments, the solvent is heated to a temperature of about 50° C. In some embodiments, the temperature is from about 50° C. to about 80° C. In some embodiments, the temperature is from about 40° C. to about 60° C. In some embodiments, the temperature is from about 45° C. to about 55° C. In some embodiments, the temperature is about 45° C., about 50° C., about 55° C., about 60° C., about 65° C., about 70° C., about 75° C. or about 80° C.

In some embodiments, the solvent is heated to a temperature that can induce precipitation at a practical rate. In some embodiments, precipitation is completed within about 12 to about 24 hours, but longer and shorter periods are possible depending on the choice of precipitation solvent and temperature. In some embodiments, the precipitation is completed within about 90 minutes.

The precipitation of the phosphoric acid salt (~1:2), in some embodiments, is carried out by filtering the salt from solution.

In some embodiments, Compound 1 phosphoric acid salt (~1:2) is amorphous.

Compound 1 phosphoric acid salt (~1:3) can be prepared by any suitable method for preparation of phosphoric acid (~1:3) addition salts. For example, Compound 1 can be combined with phosphoric acid (e.g., about 3.0 molar eq. or more) in a solvent and the resulting salt can be isolated by filtering the salt from solution. In certain embodiments, Compound 1 is combined with about 3 to about 5 molar equivalents of phosphoric acid. In certain embodiments, Compound 1 is combined with about 3 to about 4 molar equivalents of phosphoric acid. In certain embodiments, Compound 1 is combined with about 3 molar equivalents of phosphoric acid.

The solvent can contain any solvent or mixture of solvents capable of at least partially dissolving Compound 1. In some embodiments, the solvent contains an alcohol. Suitable alcohols include methanol, ethanol, 2-nitroethanol, 2-fluoroethanol, 2,2,2-trifluoroethanol, ethylene glycol, 1-propanol, isopropanol (isopropyl alcohol, 2-propanol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol. In some embodiments, the solvent contains acetone, tetrahydrofuran, dichloromethane, methanol, ethanol, 1-propanol, or isopropanol. In some embodiments, the solvent contains acetone.

In some embodiments, the solvent is a mixture of acetone, methanol and dichloromethane.

In some embodiments, the solvent is about room temperature. In some embodiments, the solvent is heated to a temperature of about 50° C. In some embodiments, the temperature is from about 50° C. to about 80° C. In some embodiments, the temperature is from about 40° C. to about 60° C. In some embodiments, the temperature is from about 45° C. to about 55° C. In some embodiments, the temperature is about 45° C., about 50° C., about 55° C., about 60° C., about 65° C., about 70° C., about 75° C. or about 80° C.

In some embodiments, the solvent is heated to a temperature that can induce precipitation at a practical rate. In some embodiments, precipitation is completed within about 12 to about 24 hours, but longer and shorter periods are possible depending on the choice of precipitation solvent and temperature. In some embodiments, the precipitation is completed within about 90 minutes.

The precipitation of the phosphoric acid salt (~1:3), in some embodiments, is carried out by filtering the salt from solution.

In some embodiments, Compound 1 phosphoric acid salt (~1:3) is amorphous.

Different forms of the same substance have different bulk properties relating to, for example, hygroscopicity, solubility, stability, and the like. Forms with high melting points often have good thermodynamic stability which is advantageous in prolonging shelf-life drug formulations containing the solid form. Forms with lower melting points often are less thermodynamically stable, but are advantageous in that they have increased water solubility, translating to increased drug bioavailability. Forms that are weakly hygroscopic are desirable for their stability to heat and humidity and are resistant to degradation during long storage.

In some embodiments, a Compound 1 salt provided herein is crystalline. As used herein, "crystalline" or "crystalline form" is meant to refer to a certain lattice configuration of a crystalline substance. Different crystalline forms of the same substance typically have different crystalline lattices (e.g., unit cells) which are attributed to different physical properties that are characteristic of each of the crystalline forms. In some instances, different lattice configurations have different water or solvent content.

The different salt forms can be identified by solid state characterization methods such as by X-ray powder diffraction (XRPD). Other characterization methods such as differential scanning calorimetry (DSC), thermogravimetric analysis (TGA), dynamic vapor sorption (DVS), solid state NMR, and the like further help identify the form as well as help determine stability and solvent/water content.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, various filters used, the sample mounting procedure, and the particular instrument employed. In some instances, new peaks may be observed or existing peaks may disappear, depending on the type of the instrument or the settings. As used herein, the term "peak" refers to a reflection having a relative height/intensity of at least about 4% of the maximum peak height/intensity. Moreover, instrument variation and other factors can affect the 2-theta values. Thus, peak assignments, such as those reported herein, can vary by plus or minus about 0.2° (2-theta), and the term "substantially" and "about" as used in the context of XRPD herein is meant to encompass the above-mentioned variations.

In the same way, temperature readings in connection with DSC, TGA, or other thermal experiments can vary about 3° C. depending on the instrument, particular settings, sample preparation, etc. Accordingly, a crystalline form reported herein having a DSC thermogram "substantially" as shown in any of the Figures or the term "about" is understood to accommodate such variation.

In some embodiments, the term "about" means±10%. In some embodiments, the term "about" means±5%.

In some embodiments, the salts described herein are substantially isolated. By "substantially isolated" is meant that the salt is at least partially or substantially separated from the environment in which it was formed or detected. Partial separation can include, for example, a composition enriched in the salts described herein. Substantial separation can include compositions containing at least about 50%, at least about 60%, at least about 70%, at least about 80%, at least about 90%, at least about 95%, at least about 97%, or at least about 99% by weight of the salts described herein, or salt thereof. Methods for isolating salts are routine in the art.

Salts of the invention can also include all isotopes of atoms occurring in the final salts or Compound 1. Isotopes include those atoms having the same atomic number but different mass numbers. For example, isotopes of hydrogen include tritium and deuterium.

In some embodiments, the salts can be found together with other substances such as water and solvents (e.g., hydrates and solvates) or can be isolated.

The phrase "pharmaceutically acceptable" is employed herein to refer to those salts, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The salt forming reactions described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures).

The expressions, "ambient temperature" and "room temperature" or "rt" as used herein, are understood in the art, and refer generally to a temperature, e.g., a reaction temperature, that is about the temperature of the room in which the salt forming reaction is carried out, for example, a temperature from about 20° C. to about 30° C.

The salt forming reactions described herein can be carried out in air or under an inert atmosphere. Typically, reactions containing reagents or products that are substantially reactive with air can be carried out using air-sensitive synthetic techniques that are well known to the skilled artisan.

Methods of Use

Salts of the present disclosure can inhibit the activity of PD-1/PD-L1 protein/protein interaction and, thus, are useful in treating diseases and disorders associated with activity of PD-1 and the diseases and disorders associated with PD-L1 including its interaction with other proteins such as PD-1 and B7-1 (CD80). In certain embodiments, the salts of the present disclosure are useful for therapeutic administration to enhance, stimulate and/or increase immunity in cancer, chronic infection or sepsis, including enhancement of response to vaccination. In some embodiments, the present disclosure provides a method for inhibiting the PD-1/PD-L1 protein/protein interaction. The method includes administering to an individual or a patient a salt of Compound 1, or of a salt as recited in any of the claims and described herein, or a pharmaceutically acceptable salt or a stereoisomer thereof. The salts of the present disclosure can be used alone, in combination with other agents or therapies or as an adjuvant or neoadjuvant for the treatment of diseases or disorders, including cancer or infection diseases. For the uses described herein, any of the salts of the disclosure, including any of the embodiments thereof, may be used.

The salts of the present disclosure inhibit the PD-1/PD-L1 protein/protein interaction, resulting in a PD-1 pathway blockade. The blockade of PD-1 can enhance the immune response to cancerous cells and infectious diseases in mammals, including humans. In some embodiments, the present disclosure provides treatment of an individual or a patient in vivo using a salt of Compound 1 such that growth of cancerous tumors is inhibited. A salt of Compound 1, or a salt as recited in any of the claims and described herein, can be used to inhibit the growth of cancerous tumors. Alternatively, a salt of Compound 1, or a salt as recited in any of the claims and described herein, can be used in conjunction with other agents or standard cancer treatments, as described below. In one embodiment, the present disclosure provides a method for inhibiting growth of tumor cells in vitro. The method includes contacting the tumor cells in vitro with a salt of Compound 1, or of a salt as recited in any of the claims and described herein. In another embodiment, the present disclosure provides a method for inhibiting growth of tumor cells in an individual or a patient. The method includes administering to the individual or patient in need thereof a therapeutically effective amount of a salt of Compound 1, or of a salt as recited in any of the claims and described herein.

In some embodiments, provided herein is a method for treating cancer. The method includes administering to a patient in need thereof, a therapeutically effective amount of a salt of Compound 1, or a salt as recited in any of the claims and described herein. Examples of cancers include those whose growth may be inhibited using salts of the disclosure and cancers typically responsive to immunotherapy.

In some embodiments, the present disclosure provides a method of enhancing, stimulating and/or increasing the immune response in a patient. The method includes administering to the patient in need thereof a therapeutically effective amount of a salt of Compound 1, or a salt or composition as recited in any of the claims and described herein.

Examples of cancers that are treatable using the salts of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The salts of the present disclosure are also useful for the treatment of metastatic cancers, especially metastatic cancers that express PD-L1.

In some embodiments, cancers treatable with salts of the present disclosure include melanoma (e.g., metastatic malignant melanoma, cutaneous melanoma), renal cancer (e.g., clear cell carcinoma), prostate cancer (e.g., hormone refractory prostate adenocarcinoma), breast cancer (e.g., breast invasive carcinoma), colon cancer, lung cancer (e.g., non-small cell lung cancer and small cell lung cancer), squamous cell head and neck cancer (e.g., squamous cell carcinoma of the head and neck), urothelial cancer (e.g., bladder cancer, nonmuscle invasive bladder cancer (NMIBC)) and cancers with high microsatellite instability ($MSI^{high}$). Additionally, the disclosure includes refractory or recurrent malignancies whose growth may be inhibited using the salts of the disclosure.

In some embodiments, cancers that are treatable using the salts of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In some embodiments, cancers that are treatable using the salts of the present disclosure include, but are not limited to, cholangiocarcinoma, bile duct cancer, biliary tract cancer, triple negative breast cancer, rhabdomyosarcoma, small cell lung cancer, leiomyosarcoma, hepatocellular carcinoma, Ewing's sarcoma, brain cancer, brain tumor, astrocytoma, neuroblastoma, neurofibroma, basal cell carcinoma, chondrosarcoma, epithelioid sarcoma, eye cancer, Fallopian tube cancer, gastrointestinal cancer, gastrointestinal stromal tumors, hairy cell leukemia, intestinal cancer, islet cell cancer, oral cancer, mouth cancer, throat cancer, laryngeal cancer, lip cancer, mesothelioma, neck cancer, nasal cavity cancer, ocular cancer, ocular melanoma, pelvic cancer, rectal cancer, renal cell carcinoma, salivary gland cancer, sinus cancer, spinal cancer, tongue cancer, tubular carcinoma, urethral cancer, and ureteral cancer.

In some embodiments, the salts of the present disclosure can be used to treat sickle cell disease and sickle cell anemia.

In some embodiments, diseases and indications that are treatable using the salts of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), and essential thrombocytosis (ET)), myelodysplasia syndrome (MDS), T-cell acute lymphoblastic lymphoma (T-ALL) and multiple myeloma (MM).

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC) (e.g., squamous cell NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (carcinoma, squamous cell carcinoma, adenocarcinoma, leiomyosarcoma, lymphoma), stomach (carcinoma, lymphoma, leiomyosarcoma, adenocarcinoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer (e.g., colorectal adenocarcinoma).

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma). In some embodiments, the cancer is a urological cancer (e.g., papillary kidney carcinoma, testicular germ cell cancer, chromophobe renal cell carcinoma, clear cell renal carcinoma, or prostate adenocarcinoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors.

Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, serous adenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma (e.g., cutaneous squamous cell carcinoma), Kaposi's sarcoma, moles dysplastic nevi, lipoma, angioma, dermatofibroma, and keloids. In some embodiments, diseases and indications that are treatable using the salts of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

PD-1 pathway blockade with salts of the present disclosure can also be used for treating infections such as viral, bacteria, fungus and parasite infections. The present disclosure provides a method for treating infections such as viral infections. The method includes administering to a patient in need thereof, a therapeutically effective amount of a salt of Compound 1, or a salt as recited in any of the claims and described herein. Examples of viruses causing infections treatable by methods of the present disclosure include, but are not limited to, human immunodeficiency virus, human papillomavirus, influenza, hepatitis A, B, C or D viruses, adenovirus, poxvirus, herpes simplex viruses, human cytomegalovirus, severe acute respiratory syndrome virus, ebola virus, and measles virus. In some embodiments, viruses causing infections treatable by methods of the present disclosure include, but are not limited to, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus, tuberculosis and arboviral encephalitis virus.

The present disclosure provides a method for treating bacterial infections. The method includes administering to a patient in need thereof, a therapeutically effective amount of a salt of Compound 1, or a salt as recited in any of the claims and described herein. Non-limiting examples of pathogenic bacteria causing infections treatable by methods of the disclosure include *chlamydia*, rickettsial bacteria, mycobacteria, staphylococci, streptococci, pneumococci, meningococci and conococci, *klebsiella, proteus, serratia, pseudomonas, legionella, diphtheria, salmonella*, bacilli, cholera, tetanus, botulism, anthrax, plague, leptospirosis, and Lyme's disease bacteria.

The present disclosure provides a method for treating fungus infections. The method includes administering to a patient in need thereof, a therapeutically effective amount of a salt of Compound 1, or a salt as recited in any of the claims and described herein. Non-limiting examples of pathogenic fungi causing infections treatable by methods of the disclosure include *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*.

The present disclosure provides a method for treating parasite infections. The method includes administering to a patient in need thereof, a therapeutically effective amount of a salt of Compound 1, or a salt as recited in any of the claims and described herein. Non-limiting examples of pathogenic parasites causing infections treatable by methods of the disclosure include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

The present disclosure provides a method for treating neurodegenerative diseases or disorders. The method includes administering to a patient in need thereof, a therapeutically effective amount of a salt of Compound 1, or a salt as recited in any of the claims and described herein. Non-limiting examples of neurodegenerative diseases or disorders include Alzheimer's disease, Parkinson's disease, Huntington's disease, prion disease, Motor neurone diseases, Spinocerebellar ataxia and Spinal muscular atrophy.

It is believed that salts of Compound 1, or any of the embodiments thereof, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active salt that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the salts of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

Immune-Checkpoint Therapies

Salts of the present disclosure can be used in combination with one or more immune checkpoint inhibitors for the treatment of diseases, such as cancer or infections. Exemplary immune checkpoint inhibitors include inhibitors against immune checkpoint molecules such as CBL-B, CD20, CD122, CD96, CD73, CD47, CSF1R, JAK, PI3K delta, PI3K gamma, TAM, arginase, HPK1, A2AR, B7-H3, B7-H4, BTLA, CTLA-4, LAG3, TIM3, TIGIT, CD112R, VISTA, PD-1, PD-L1 and PD-L2. In some embodiments, the immune checkpoint molecule is a stimulatory checkpoint molecule selected from CD27, CD28, CD40, ICOS, OX40, GITR and CD137 (4-1BB). In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the salts provided herein can be used in combination with one or more agents selected from KIR inhibitors, TIGIT inhibitors, LAIR1 inhibitors, CD160 inhibitors, 2B4 inhibitors and TGF beta inhibitors.

In some embodiments, the salts provided herein can be used in combination with one or more agonists of immune checkpoint molecules, e.g., OX40, CD27, GITR, and CD137 (also known as 4-1B).

In some embodiments, the agonist of an immune checkpoint molecule is an agonist of OX40, CD27, CD28, GITR, ICOS, CD40, TLR7/8, and CD137 (also known as 4-1B).

In some embodiments, the agonist of CD137 is urelumab. In some embodiments, the agonist of CD137 is utomilumab.

In some embodiments, the agonist of an immune checkpoint molecule is an agonist of CD40. In some embodiments, the agonist of CD40 is CP-870893, ADC-1013, CDX-1140, SEA-CD40, RO7009789, JNJ-64457107, APX-005M, or Chi Lob 7/4.

In some embodiments, the agonist of an immune checkpoint molecule is an agonist of ICOS. In some embodiments, the agonist of ICOS is GSK-3359609, JTX-2011, or MEDI-570.

In some embodiments, the agonist of an immune checkpoint molecule is an agonist of CD28. In some embodiments, the agonist of CD28 is theralizumab.

In some embodiments, the agonist of an immune checkpoint molecule is an agonist of CD27. In some embodiments, the agonist of CD27 is varlilumab.

In some embodiments, the agonist of an immune checkpoint molecule is an agonist of TLR7/8. In some embodiments, the agonist of TLR7/8 is MEDI9197.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, cemiplimab, spartalizumab, camrelizumab, cetrelimab, toripalimab, sintilimab, SHR-1210, PDR001, MGA012, PDR001, AB122, AMP-224, JTX-4014, BGB-108, BCD-100, BAT1306, LZM009, AK105, HLX10, or TSR-042. In some embodiments, the anti-PD-1 monoclonal antibody is nivolumab or pembrolizumab. In some embodiments, the anti-PD1 antibody is pembrolizumab. In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g. urelumab, utomilumab).

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), durvalumab (Imfinzi®), atezolizumab (Tecentriq®), Avelumab (Bavencio®), MSB0010718C, tislelizumab, FAZ053, KN035, CS1001, SHR-1316, CBT-502, A167, STI-A101, CK-301, BGB-A333, MSB-2311, HLX20, or LY3300054. In some embodiments, the anti-PD-L1 monoclonal antibody is MPDL3280A or MEDI4736.

In some embodiments, the inhibitor of an immune checkpoint molecule is an inhibitor of PD-1 and PD-L1, e.g., an anti-PD-1/PD-L1 bispecific antibody. In some embodiments, the anti-PD-1/PD-L1 bispecific antibody is MCLA-136.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of PD-1 and CTLA-4, e.g., an anti-PD-1/CTLA-4 bispecific antibody. In some embodiments, the anti-PD-1/CTLA-4 antibody is AK104.

In some embodiments, the inhibitor of an immune checkpoint molecule is an inhibitor of LAG3, e.g., an anti-LAG3 antibody. In some embodiments, the anti-LAG3 antibody is BMS-986016, LAG525, INCAGN2385, or eftilagimod alpha (IMP321).

In some embodiments, the inhibitor of an immune checkpoint molecule is an inhibitor of CD73. In some embodiments, the inhibitor of CD73 is oleclumab. In some embodiments, the inhibitor of CD73 is MEDI9447.

In some embodiments, the inhibitor of an immune checkpoint molecule is an inhibitor of TIGIT. In some embodiments, the inhibitor of TIGIT is OMP-31M32.

In some embodiments, the inhibitor of an immune checkpoint molecule is an inhibitor of VISTA. In some embodiments, the inhibitor of VISTA is JNJ-61610588 or CA-170.

In some embodiments, the inhibitor of an immune checkpoint molecule is an inhibitor of B7-H3. In some embodiments, the inhibitor of B7-H3 is enoblituzumab, MGD009, or 8H9.

In some embodiments, the inhibitor of an immune checkpoint molecule is an inhibitor of KIR. In some embodiments, the inhibitor of KIR is lirilumab or IPH4102.

In some embodiments, the inhibitor of an immune checkpoint molecule is an inhibitor of A2aR. In some embodiments, the inhibitor of A2aR is CPI-444.

In some embodiments, the inhibitor of an immune checkpoint molecule is an inhibitor of TGF-beta. In some embodiments, the inhibitor of TGF-beta is trabedersen, galusertinib, or M7824.

In some embodiments, the inhibitor of an immune checkpoint molecule is an inhibitor of PI3K-gamma. In some embodiments, the inhibitor of PI3K-gamma is IPI-549.

In some embodiments, the inhibitor of an immune checkpoint molecule is an inhibitor of CD47. In some embodiments, the inhibitor of CD47 is Hu5F9-G4 or TTI-621.

In some embodiments, the inhibitor of an immune checkpoint molecule is an inhibitor of CD70. In some embodiments, the inhibitor of CD70 is cusatuzumab or BMS-936561.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the agonist of an immune checkpoint molecule is an agonist of GITR, e.g., an anti-GITR antibody. In some embodiments, the agonist is TRX518, MK-4166, INCAGN1876, MK-1248, AMG228, BMS-986156, GWN323, MEDI1873, or MEDI6469.

In some embodiments, the agonist of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, BMS-986178, or 9B12. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The salts of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor. In some embodiments, the bispecific antibody binds to PD-1 and PD-L1. In some embodiments, the bispecific antibody that binds to PD-1 and PD-L1 is MCLA-136. In some embodiments, the bispecific antibody binds to PD-L1 and CTLA-4. In some embodiments, the bispecific antibody that binds to PD-L1 and CTLA-4 is AK104.

In some embodiments, the salts of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

As provided throughout, the additional compounds, inhibitors, agents, etc. can be combined with the present salt in a single or continuous dosage form, or they can be administered simultaneously or sequentially as separate dosage forms.

Cancer Therapies

Cancer cell growth and survival can be impacted by dysfunction in multiple biological pathways. Thus, it may be useful to combine inhibitors of different mechanisms, such as enzyme inhibitors, signal transduction inhibitors, inhibitors of chromatin dynamics or modulators of immune responses, to treat such conditions. Targeting more than one signaling pathway (or more than one biological molecule involved in a given signaling pathway) may reduce the likelihood of drug-resistance arising in a cell population, or reduce the toxicity of treatment.

The salts of the present disclosure can be used in combination with one or more other therapies for the treatment of diseases, such as cancer or infections. Examples of diseases and indications treatable with combination therapies include those as described herein. Examples of cancers include solid tumors and non-solid tumors, such as liquid tumors, blood cancers. Examples of infections include viral infections, bacterial infections, fungus infections or parasite infections. For example, the salts of the present disclosure can be combined with one or more inhibitors of the following kinases for the treatment of cancer: Akt1, Akt2, Akt3, BCL2, CDK, TGF-βR, PKA, PKG, PKC, CaM-kinase, phosphorylase kinase, MEKK, ERK, MAPK, mTOR, EGFR, HER2, HER3, HER4, INS-R, IDH2, IGF-1R, IR-R, PDGFαR, PDGFβR, PI3K (alpha, beta, gamma, delta, and multiple or selective), CSF1R, KIT, FLK-II, KDR/FLK-1, FLK-4, fit-1, FGFR1, FGFR2, FGFR3, FGFR4, c-Met, PARP, Ron, Sea, TRKA, TRKB, TRKC, TAM kinases (Axl, Mer, Tyro3), FLT3, VEGFR/Flt2, Flt4, EphA, EphA2, EphA3, EphB2, EphB4, Tie2, Src, Fyn, Lck, Fgr, Btk, Fak, SYK, FRK, JAK, ABL, ALK and B-Raf. In some embodiments, the salts of the present disclosure can be combined with one or more of the following inhibitors for the treatment of cancer or infections. Non-limiting examples of inhibitors that can be combined with the salts of the present disclosure for treatment of cancer and infections include an FGFR inhibitor (FGFR1, FGFR2, FGFR3 or FGFR4, e.g., pemigatinib (INCY54828), INCB62079), an EGFR (also known as ErB-1 or HER-1) inhibitor (e.g., erlotinib, gefitinib, vandetanib, orsimertinib, cetuximab, necitumumab, or panitumumab), a VEGFR inhibitor or pathway blocker (e.g., bevacizumab, pazopanib, sunitinib, sorafenib, axitinib, regorafenib, ponatinib, cabozantinib, vandetanib, ramucirumab, lenvatinib, ziv-aflibercept), a PARP inhibitor (e.g., olaparib, rucaparib, veliparib or niraparib), a JAK inhibitor (JAK1 and/or JAK2, e.g., ruxolitinib, baricitinib or itacitinib (INCB39110)), an IDO inhibitor (e.g., epacadostat, NLG919, or BMS-986205, MK7162), an LSD1 inhibitor (e.g., INCB59872 and INCB60003), a TDO inhibitor, a PI3K-delta inhibitor (e.g., Parsaclisib (INCB50465) and INCB50797), a PI3K-gamma inhibitor such as PI3K-gamma selective inhibitor, a Pim inhibitor (e.g., INCB53914), an EGFR inhibitor (also known as ErB-1 or HER-1; e.g., erlotinib, gefitinib, vandetanib, orsimertinib, cetuximab, necitumumab, or panitumumab), a VEGFR inhibitor or pathway blocker (e.g., bevacizumab, pazopanib, sunitinib, sorafenib, axitinib, regorafenib, ponatinib, cabozantinib, vandetanib, ramucirumab, lenvatinib, ziv-aflibercept), a PARP inhibitor (e.g., olaparib, rucaparib, veliparib, talazoparib, or niraparib), a CSF1R inhibitor, a TAM receptor tyrosine kinase (Tyro-3, Axl, and Mer), an adenosine receptor antagonist (e.g., A2a/A2b receptor antagonist), an HPK1 inhibitor, a chemokine receptor inhibitor (e.g., CCR2 or CCR5 inhibitor), a SHP1/2 phosphatase inhibitor, a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643), an arginase inhibitor (INCB001158), a PARP inhibitor (such as rucaparib or olaparib), sitravatinib, a B-Raf inhibitor-MEK inhibitor combination (such as encorafenib plus binimetinib, dabrafenib plus trametinib, or cobimetinib plus vemurafenib), and an adenosine receptor antagonist or combinations thereof.

In some embodiments, the salts of the present disclosure can be combined with a TLR7 agonist (e.g., imiquimod).

The salts of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, bispecific or multi-specific antibody, antibody drug conjugate, adoptive T cell transfer, Toll receptor agonists, STING agonists, RIG-I agonists, oncolytic virotherapy and immunomodulating small molecules, including thalidomide or JAK1/2 inhibitor, PI3Kδ inhibitor and the like. The salts can be administered in combination with one or more anti-cancer drugs, such as a chemotherapeutic agent. Examples of chemotherapeutics include any of abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

Other anti-cancer agent(s) include antibody therapeutics such as trastuzumab (Herceptin), antibodies to costimulatory molecules such as CTLA-4 (e.g., ipilimumab), 4-1BB (e.g., urelumab, utomilumab), antibodies to PD-1 and PD-L1, antibodies to cytokines (IL-10, TGF-β, etc.). Examples of antibodies to PD-1 and/or PD-L1 that can be combined with salts of the present disclosure for the treatment of cancer or infections such as viral, bacteria, fungus and parasite infections include, but are not limited to nivolumab, pembrolizumab, atezolizumab, durvalumab, avelumab and SHR-1210.

The salts of the present disclosure can further be used in combination with one or more anti-inflammatory agents, steroids, immunosuppressants or therapeutic antibodies.

The salts of Compound 1, or a salt as recited in any of the claims and described herein, can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The salts of Compound 1, or a salt as recited in any of the claims and described herein, can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the salts of the present disclosure can be used in combination with tumor specific antigen such as heat shock proteins isolated from tumor tissue itself. In some embodiments, the salts of Compound 1, or a salt as recited in any of the claims and described herein, can be combined with dendritic cells immunization to activate potent anti-tumor responses.

The salts of the present disclosure can be used in combination with bispecific macrocyclic peptides that target Fc alpha or Fc gamma receptor-expressing effectors cells to tumor cells. The salts of the present disclosure can also be combined with macrocyclic peptides that activate host immune responsiveness.

The salts of the present disclosure can be used in combination with bone marrow transplant for the treatment of a variety of tumors of hematopoietic origin.

The salts of Compound 1, or a salt as recited in any of the claims and described herein, can be used in combination with vaccines, to stimulate the immune response to pathogens, toxins, and self antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, Giardia, Malaria, *Leishmania, Staphylococcus aureus, Pseudomonas Aeruginosa.*

Viruses causing infections treatable by methods of the present disclosure include, but are not limited to human papillomavirus, influenza, hepatitis A, B, C or D viruses, adenovirus, poxvirus, herpes simplex viruses, human cytomegalovirus, severe acute respiratory syndrome virus, ebola virus, measles virus, herpes virus (e.g., VZV, HSV-1, HAV-6, HSV-II, and CMV, Epstein Barr virus), flaviviruses, echovirus, rhinovirus, coxsackie virus, coronavirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, *chlamydia*, rickettsial bacteria, mycobacteria, staphylococci, streptococci, pneumococci, meningococci and conococci, *klebsiella, proteus, serratia, pseudomonas, legionella, diphtheria, salmonella,* bacilli, cholera, tetanus, botulism, anthrax, plague, leptospirosis, and Lyme's disease bacteria.

Pathogenic fungi causing infections treatable by methods of the disclosure include, but are not limited to, *Candida* (*albicans, krusei, glabrata, tropicalis,* etc.), *Cryptococcus neoformans, Aspergillus* (*fumigatus, niger,* etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum.*

Pathogenic parasites causing infections treatable by methods of the disclosure include, but are not limited to, *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi,* and *Nippostrongylus brasiliensis.*

When more than one pharmaceutical agent is administered to a patient, they can be administered simultaneously, separately, sequentially, or in combination (e.g., for more than two agents).

Formulation, Dosage Forms and Administration

When employed as pharmaceuticals, the salts of the present disclosure can be administered in the form of pharmaceutical compositions. Thus the present disclosure provides a composition comprising a salt of Compound 1, or a salt as recited in any of the claims and described herein, or any of the embodiments thereof, and at least one pharmaceutically acceptable carrier or excipient. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the salt of the present disclosure, in combination with one or more pharmaceutically acceptable carriers or excipients. In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active salt, soft and hard gelatin capsules, suppositories, sterile injectable solutions and sterile packaged powders.

In preparing a formulation, the active salt can be milled to provide the appropriate particle size prior to combining with the other ingredients. If the active salt is substantially insoluble, it can be milled to a particle size of less than 200 mesh. If the active salt is substantially water soluble, the particle size can be adjusted by milling to provide a substantially uniform distribution in the formulation, e.g., about 40 mesh.

The salts of the invention may be milled using known milling procedures such as wet milling to obtain a particle size appropriate for tablet formation and for other formulation types. Finely divided (nanoparticulate) preparations of the salts of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one salt described herein. In some embodiments, the silicified microcrystalline cellulose comprises about 98% microcrystalline cellulose and about 2% silicon dioxide w/w.

In some embodiments, the composition is a sustained release composition comprising at least one salt described herein, and at least one pharmaceutically acceptable carrier or excipient. In some embodiments, the composition comprises at least one salt described herein, and at least one component selected from microcrystalline cellulose, lactose monohydrate, hydroxypropyl methylcellulose and polyethylene oxide. In some embodiments, the composition comprises at least one salt described herein, and microcrystalline cellulose, lactose monohydrate and hydroxypropyl methylcellulose. In some embodiments, the composition comprises at least one salt described herein, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel KOOLV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active salt may be effective over a wide dosage range and is generally administered in a therapeutically effective amount. It will be understood, however, that the amount of the salt actually administered will usually be determined by a physician, according to the relevant circumstances, including the condition to be treated, the chosen route of administration, the actual salt administered, the age, weight, and response of the individual patient, the severity of the patient's symptoms and the like.

The therapeutic dosage of a salt of the present invention can vary according to, e.g., the particular use for which the treatment is made, the manner of administration of the salt, the health and condition of the patient, and the judgment of the prescribing physician. The proportion or concentration of a salt of the invention in a pharmaceutical composition can vary depending upon a number of factors including dosage, chemical characteristics (e.g., hydrophobicity), and the route of administration. For example, the salts of the invention can be provided in an aqueous physiological buffer solution containing about 0.1 to about 10% w/v of the salt for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the salt selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a salt of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the salts and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the salt of the invention. The topical formulations can be suitably packaged in tubes of, e.g., 100 g which are optionally associated with instructions for the treatment of the select indication, e.g., psoriasis or other skin condition.

The amount of salt or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the preparations typically will be between 3 and 11, more preferably from 5 to 9 and most preferably from 7 to 8.

The therapeutic dosage of a salt of the present invention can vary according to, e.g., the particular use for which the treatment is made, the manner of administration of the salt, the health and condition of the patient, and the judgment of the prescribing physician. The proportion or concentration of a salt of the invention in a pharmaceutical composition can vary depending upon a number of factors including dosage, chemical characteristics (e.g., hydrophobicity), and the route of administration. For example, the salts of the invention can be provided in an aqueous physiological buffer solution containing about 0.1 to about 10% w/v of the salt for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the salt selected, formulation of the excipient, and its route of administration. Effective doses can be extrapolated from dose-response curves derived from in vitro or animal model test systems.

Labeled Compounds and Assay Methods

The salts of the present disclosure can further be useful in investigations of biological processes in normal and abnormal tissues. Thus, another aspect of the present invention relates to labeled salts of the invention (radio-labeled, fluorescent-labeled, etc.) that would be useful not only in imaging techniques but also in assays, both in vitro and in vivo, for localizing and quantitating PD-1 or PD-L1 protein in tissue samples, including human, and for identifying PD-L1 ligands by inhibition binding of a labeled compound. Accordingly, the present invention includes PD-1/PD-L1 binding assays that contain such labeled salts.

The present invention further includes isotopically-substituted salts of the disclosure. An "isotopically-substituted" salt is a salt of the invention where one or more atoms are replaced or substituted by an atom having the same atomic number but a different atomic mass or mass number, e.g., a different atomic mass or mass number from the atomic mass or mass number typically found in nature (i.e., naturally occurring). It is to be understood that a "radio-labeled" salt is a salt that has incorporated at least one isotope that is radioactive (e.g., radionuclide). Suitable radionuclides that may be incorporated in salts of the present invention include but are not limited to $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled salts will depend on the specific application of that radio-labeled salt. For example, for in vitro PD-L1 protein labeling and competition assays, salts that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

In some embodiments the radionuclide is selected from the group consisting of $^{3}H$, $^{14}C$, $^{125}I$, $^{35}S$ and $^{82}Br$. Synthetic methods for incorporating radio-isotopes into organic compounds and salts are known in the art.

Specifically, a labeled salt of the invention can be used in a screening assay to identify and/or evaluate compounds. For example, a newly synthesized or identified salt (i.e., test salt) which is labeled can be evaluated for its ability to bind a PD-L1 protein by monitoring its concentration variation when contacting with the PD-L1 protein, through tracking of the labeling. For example, a test salt (labeled) can be evaluated for its ability to reduce binding of another compound which is known to bind to a PD-L1 protein (i.e., standard compound). Accordingly, the ability of a test salt to compete with the standard compound for binding to the PD-L1 protein directly correlates to its binding affinity. Conversely, in some other screening assays, the standard salt is labeled and test compounds are unlabeled. Accordingly, the concentration of the labeled standard compound is monitored in order to evaluate the competition between the standard compound and the test salt, and the relative binding affinity of the test salt is thus ascertained.

Kits

The present disclosure also includes pharmaceutical kits useful, e.g., in the treatment or prevention of diseases or disorders associated with the activity of PD-L1 including its interaction with other proteins such as PD-1 and B7-1 (CD80), such as cancer or infections, which include one or more containers containing a pharmaceutical composition comprising a therapeutically effective amount of a salt of Compound 1, or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The following abbreviations may be used herein: aq. (aqueous); br (broad); d (doublet); dd (doublet of doublets); DCM (dichloromethane); DMF (N, N-dimethylformamide); Et (ethyl); EtOAc (ethyl acetate); g (gram(s)); h (hour(s)); HPLC (high performance liquid chromatography); Hz (hertz); J (coupling constant); LCMS (liquid chromatography-mass spectrometry); m (multiplet); M (molar); MS (Mass spectrometry); Me (methyl); MeCN (acetonitrile); MeOH (methanol); mg (milligram(s)); min. (minutes(s)); mL (milliliter(s)); mmol (millimole(s)); nM (nanomolar); NMR (nuclear magnetic resonance spectroscopy); Ph (phenyl); r.t. (room temperature), s (singlet); t (triplet or tertiary); TBS (tert-butyldimethylsilyl); tert (tertiary); tt (triplet of triplets); TFA (trifluoroacetic acid); THF (tetrahydrofuran); μg (microgram(s)); μL (microliter(s)); μM (micromolar); wt % (weight percent).

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The salts of the Examples have been found to inhibit the activity of PD-1/PD-L1 protein/protein interaction according to at least one assay described herein.

EXAMPLES

Experimental Methods

In the below examples, X-Ray Powder Diffraction analysis was carried out on a Rigaku MiniFlex X-ray Powder Diffractometer (XRPD) instrument. The general experimental procedures for XRPD were: (1) X-ray radiation from copper at 1.054056 Å with $K_\beta$ filter; (2) X-ray power at 30 KV, 15 mA; and (3) the sample powder was dispersed on a zero-background sample holder. The general measurement conditions for XRPD were: Start Angle 3 degrees; Stop Angle 45 degrees; Sampling 0.02 degrees; and Scan speed 2 degree/min.

Differential Scanning Calorimetry (DSC) was carried out on a TA Instruments Differential Scanning Calorimetry, Model Q200 with autosampler. The DSC instrument conditions were as follows: 30-300° C. at 10° C./min; Tzero aluminum sample pan and lid; and nitrogen gas flow at 50 mL/min.

Thermogravimetric analysis (TGA) was carried out on a TA Instrument Thermogravimetric Analyzer, Model Q500. The general experimental conditions for TGA were: ramp from 20° C.-600° C. at 20° C./min; nitrogen purge, gas flow at 40 mL/min followed by balance of the purge flow; sample purge flow at 60 mL/min; platinum sample pan.

Purity was determined by HPLC using the conditions shown below.

| | |
|---|---|
| Instrument | Agilent 1100 |
| Column | Zorbax SB-C18, 3.5 μm, 4.6 × 150 mm |
| Column Temperature | 40° C. |
| Mobile Phase A | 0.05% TFA in water |
| Mobile Phase B | 0.05% TFA In acetonitrile |
| Flow Rate | 1 mL/min |
| Injection Volume | 5 μL |
| Total Run Time | 24 min |
| UV Detector Wavelength | 254 nm |

Gradient Table:

| Time (min) | Mobile Phase A | Mobile Phase B |
|---|---|---|
| 0 | 95 | 5 |
| 15 | 5 | 95 |
| 18 | 5 | 95 |
| 18.5 | 95 | 5 |
| 24 | 95 | 5 |

Example 1. Preparation of the Compound 1 Mono-Malonic Acid Salt

Into a 500 mL round bottom flask with stir bar and was charged acetone (200 mL) followed by malonic acid (0.825 g, 7.93 mmol). The mixture was stirred at room temperature until completely homogeneous.

Into a 100 mL round bottom flask with stir bar was charged Compound 1 (5.0 g, 7.21 mmol), methanol (5.0 mL) and dichloromethane (45.0 mL). The mixture was stirred until homogeneous.

The solution (slightly turbid) was polish filtered directly into a 60 mL addition funnel using a syringe and filter disks. The round bottom flask was rinsed with 6 mL 10% methanol/dichloromethane solution and the solution was filtered into the addition funnel. The Compound 1 solution was added over 29 minutes. The addition funnel was rinsed with 4 mL 10% methanol/dichloromethane, and added to the slurry. The slurry was stirred for 90 minutes at room temperature.

The filter cake was rinsed with acetone (100 mL), and the solids were dried in a desiccator for 3.5 hours under high vacuum. The recovered solid was 5.2 g, and placed in a 50° C. vacuum oven under nitrogen atmosphere for 16 hours. 5.1 g of product was recovered. HPLC purity 98.69%. Residual acetone (NMR): 940 ppm.

Example 2. Preparation of the Compound 1 Mono-Hydrobromic Acid Salt

Hydrobromic acid (0.322 mL, 0.322 mmol, 1.0 M in isopropyl alcohol/water from 48% aqueous solution, 1.05 eq.) was added to a solution of Compound 1 (212.62 mg, 0.306 mmol, 1.0 eq.) in a 3:2 v/v mixture of methanol and dichloromethane (7.0 mL). The reaction mixture was stirred to give a thin slurry. The thin slurry was stirred for 1 h to give a slurry, and continuously stirred overnight. The slurry was filtered to give a mother liquid and a solid. The solid was dried under vacuum at 45-46° C. overnight to provide Compound 1 mono-hydrobromic acid salt as an amorphous solid (195 mg, 82% yield).

The stoichiometric ratio between Compound 1 and hydrobromic acid was determined as 1:1 by HPLC. Compound 1 mono-hydrobromic acid salt was characterized by XRPD (FIG. 1). Analytical data collected on the product were obtained. The purity of the mono-hydrobromic acid salt was determined by HPLC as 99.4%.

Example 3. Alternative Preparation of the Compound 1 Mono-Hydrobromic Acid Salt

Hydrobromic acid (0.097 mL, 0.097 mmol, 1.0 M in isopropyl alcohol/water from 48% aqueous solution, 1.05 eq.) was added dropwise to a solution of Compound 1 (63.79 mg, 0.092 mmol, 1.0 eq.) in tetrahydrofuran (1.6 mL). The reaction mixture was stirred to give a good slurry. The slurry was stirred for 2 h, and filtered. The solid was dried under vacuum at 40-41° C. overnight to provide Compound 1 mono-hydrobromic acid salt as an amorphous solid (63.70 mg, 89% yield).

The stoichiometric ratio between Compound 1 and hydrobromic acid was determined as 1:1 by HPLC. Compound 1 mono-hydrobromic acid salt was characterized by XRPD (FIG. 2). Analytical data collected on the product were obtained. The purity of the mono-hydrobromic acid salt was determined by HPLC as 99.7%.

Example 4. Preparation of the Compound 1 Mono-Oxalic Acid Salt

Oxalic acid (7.41 mg, 0.082 mmol, 1.05 eq.) was added to a solution of Compound 1 (54.36 mg, 0.076 mmol, 1.0 eq.) in tetrahydrofuran (2.0 mL). The reaction mixture was stirred to give a slurry. The slurry was stirred for 2 h, and filtered to give a mother liquid and a solid. The solid was dried under vacuum at 40-41° C. overnight to provide Compound 1 mono-oxalic acid salt as an amorphous solid (54.5 mg, 89% yield).

The stoichiometric ratio between Compound 1 and oxalic acid was determined as 1:1 by elemental analysis (calculated for $C_{43}H_{41}N_7O_8 \cdot 2H_2O$: C, 62.99; H, 5.53; N, 11.96 and analysis found C, 62.48; H, 5.33; N, 11.44). Compound 1 mono-oxalic acid salt was characterized by XRPD (FIG. 3). TGA of the salt is provided in FIG. 4. Analytical data collected on the product were obtained. The purity of the mono-oxalic acid salt was determined by HPLC as 99.3%.

Example 5. Alternate Preparation of the Compound 1 Mono-Oxalic Acid Salt

Into a 50 mL round bottom flask with stir bar and was charged acetone (10.7 mL) followed by oxalic acid (77 mg, 0.851 mmol). The mixture was stirred at room temperature until completely homogeneous.

Into a scintillation vial with stir bar was charged Compound 1 (537 mg, 0.774 mmol), methanol (537 μL) and dichloromethane (4.83 mL). The mixture was stirred until homogeneous.

The Compound 1 solution was polish filtered directly into a clean scintillation vial using a syringe and filter disks. The Compound 1 solution was added dropwise over 3 minutes via pipet. The slurry was stirred for 90 minutes at room temperature, and the solids were filtered. The filter cake was rinsed with acetone (10 mL), and the solids were dried under high vacuum for 18 hours. 565 mg of product was recovered having a purity 98.58%

Example 6. Preparation of the Compound 1 Mono-Hydrochloric Acid Salt

Hydrochloric acid (0.504 mL, 0.504 mmol, 1.0 M in isopropyl alcohol/water from 37% aqueous solution, 1.05 eq.) was added to a solution of Compound 1 (332.80 mg, 0.480 mmol, 1.0 eq.) in a 3:2 v/v mixture of methanol and dichloromethane (9.0 mL). The reaction mixture was stirred to give a clear solution, and continuously stirred for 1 h. Dichloromethane was removed to give a slurry, and the slurry was stirred overnight. The slurry was filtered to give a mother liquid and a solid. The solid was dried under vacuum at 45-46° C. overnight to provide Compound 1 mono-hydrochloric acid salt as an amorphous solid (287.7 mg, 82% yield).

The stoichiometric ratio between Compound 1 and hydrochloric acid was determined as 1:1 by HPLC. Compound 1 mono-hydrochloric acid salt was characterized by XRPD (FIG. 5). Analytical data collected on the product were obtained. The purity of the mono-hydrochloric acid salt was determined by HPLC as 99.0%.

Example 7. Preparation of the Compound 1 L-Tartaric Acid Salt (1:1.5)

L-tartaric acid (11.74 mg, 0.078 mmol, 1.05 eq.) was added to a solution of Compound 1 (51.58 mg, 0.074 mmol) in tetrahydrofuran (1.6 mL). The reaction mixture was stirred for 25 minutes to give a slurry. The slurry was stirred continuously for 2 hours, and then filtered to give a mother liquid and a solid. The solid was dried under vacuum at 40-41° C. overnight to provide Compound 1 L-tartaric acid salt as an amorphous solid (46.5 mg, 97% yield based on the moles of L-tartaric acid used (limiting reagent)).

The stoichiometric ratio between Compound 1 and L-tartaric acid was 1:1.5 by $^1$H NMR (FIG. 7). Compound 1 L-tartaric acid salt was characterized by XRPD (FIG. 6). Analytical data collected on the product were obtained. The purity of the L-tartaric acid salt was determined by HPLC as 99.3%.

Example 8. Preparation of the Compound 1 Di-Hydrobromic Acid Salt

Hydrobromic acid (0.32 mL, 0.320 mmol, 1.0 M in isopropyl alcohol/water from 48% aqueous solution, 2.30

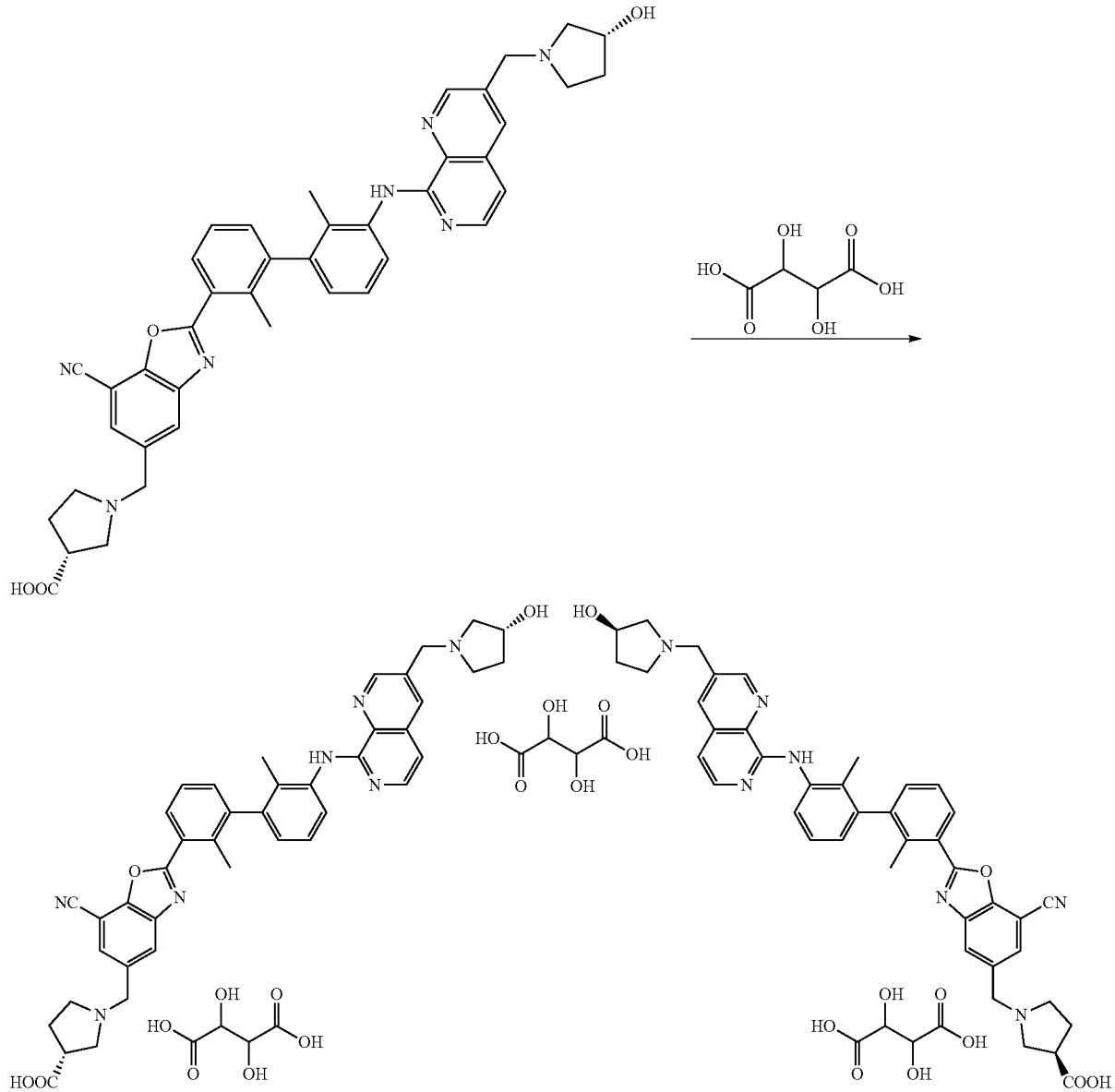

eq.) was added to a slurry of Compound 1 (100 mg, 0.141 mmol, 1.0 eq.) in methanol (2.0 mL). The reaction mixture was stirred to give a clear solution, and was then continuously stirred overnight. 0.5 mL of the slurry was filtered to give a mother liquid and a solid sample 1. Isopropyl alcohol (1.0 mL) was added to the remainder of the slurry, and continuously stirred for 4 h. The slurry was filtered to give a mother liquid and a solid sample 2. The solid samples 1 and 2 were dried under vacuum at 45-46° C. overnight to provide Compound 1 di-hydrobromic acid salt (32 mg of sample 1 and 70 mg of sample 2, 85% total yield) as amorphous solids.

The stoichiometric ratio between Compound 1 and hydrobromic acid was determined as 1:2 by HPLC (sample 2). Compound 1 di-hydrobromic acid salt was characterized by XRPD (FIG. 8, samples 1 and 2). Analytical data collected on the product were obtained. The purity of the di-hydrobromic acid salt was determined by HPLC as 97.8% (sample 1) and 97.2% (sample 2).

Example 9. Alternative Preparation of the Compound 1 Di-Hydrobromic Acid Salt Hydrobromic acid (0.149 mL, 0.149 mmol, 1.0 M in IPA/water from 48% aqueous solution, 2.04 eq.) was added dropwise to a solution of Compound 1 (50.59 mg, 0.073 mmol, 1.0 eq.) in tetrahydrofuran (2.0 mL). The reaction mixture was stirred to give a good slurry. The slurry was stirred for 2.5 h at 25° C., and filtered to give a mother liquid and a solid. The solid was dried under vacuum at 40-41° C. overnight to provide Compound 1 di-hydrobromic acid salt (56.5 mg, 91% yield) as an amorphous solid.

The stoichiometric ratio between Compound 1 and hydrobromic acid was determined as 1:2 by HPLC. Compound 1 di-hydrobromic acid salt was characterized by XRPD (FIG. 9). Analytical data collected on the product were obtained. The purity of the di-hydrobromic acid salt was determined by HPLC as 99.7%.

Example 10. Preparation of the Compound 1 Di-Oxalic Acid Salt

Oxalic acid (20.11 mg, 0.223 mmol, 2.05 eq.) was added to a solution of Compound 1 (75.58 mg, 0.109 mmol, 1.0 eq.) in tetrahydrofuran (2.0 mL). The reaction mixture was stirred to give a slurry. The slurry was stirred continuously for 2 h, and filtered to give a mother liquid and a solid. The solid was dried under vacuum at 40-41° C. overnight to provide Compound 1 di-oxalic acid salt (89.5 mg, 94% yield) as a crystalline solid.

The stoichiometric ratio between Compound 1 and oxalic acid was determined as 1:2 by elemental analysis (calculated for $C_{45}H_{43}N_7O_{12}$; C, 61.85; H, 4.96; N, 11.22 and analysis found C, 60.91; H, 5.21; N, 10.73). The crystallinity of the di-oxalic acid salt was confirmed by XRPD (FIG. 10, Table 1) and further supported by DSC (FIG. 11), indicating the salt with an onset temperature at 222.23° C. and a peak at 235.26° C. TGA of the di-oxalic acid salt is provided in FIG. 12, and exhibited approximately 0.7% of weight loss up to about 100° C. Analytical data collected on the product were obtained. The purity of the di-oxalic acid salt was determined by HPLC as 96.10%.

TABLE 1

| XRPD Peak Data for the Di-Oxalic Acid Salt | | | | | | | |
|---|---|---|---|---|---|---|---|
| 2-Theta | d(A) | BG | Height | I % | Area | I % | FWHM |
| 7.038 | 12.5487 | 138 | 87 | 28.2 | 69.4 | 23.7 | 0.678 |
| 11.36 | 7.7828 | 216 | 151 | 49 | 96.2 | 32.9 | 0.541 |
| 13.16 | 6.7222 | 257 | 56 | 18.2 | 34 | 11.6 | 0.516 |
| 14.9 | 5.9408 | 301 | 191 | 62 | 197.5 | 67.6 | 0.879 |
| 17.02 | 5.2053 | 420 | 308 | 100 | 142.6 | 48.8 | 0.393 |
| 20.839 | 4.259 | 454 | 222 | 72.1 | 292.2 | 100 | 1.119 |
| 22.56 | 3.9379 | 539 | 203 | 65.9 | 99 | 33.9 | 0.415 |
| 23.84 | 3.7294 | 581 | 129 | 41.9 | 94.2 | 32.3 | 0.621 |
| 34 | 2.6346 | 282 | 65 | 21.1 | 68.3 | 23.4 | 0.893 |

Example 11. Preparation of the Compound 1 L-Tartaric Acid Salt (1:1.7)

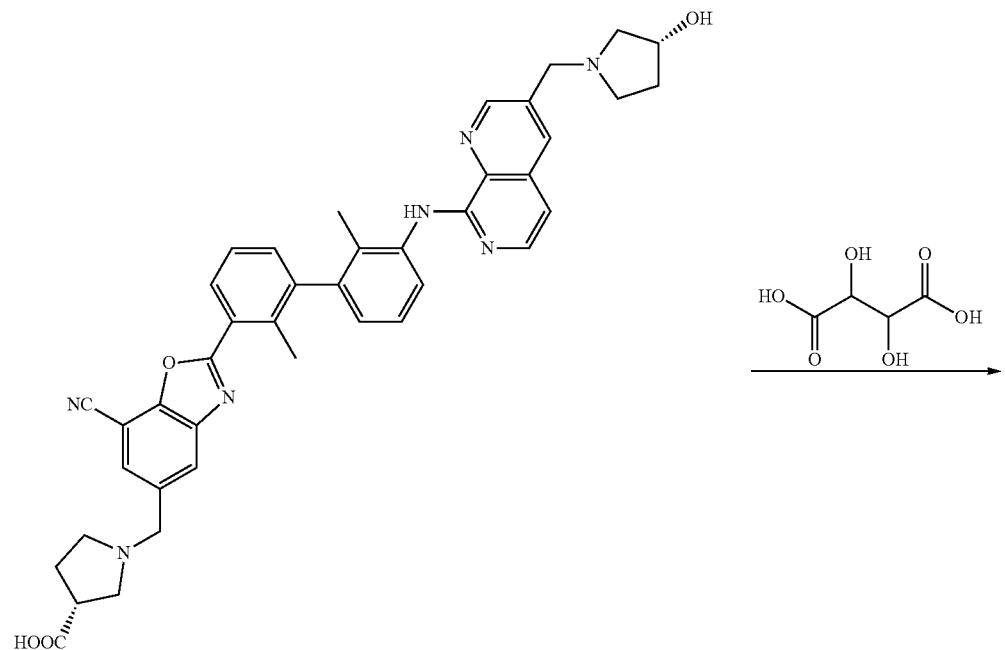

-continued

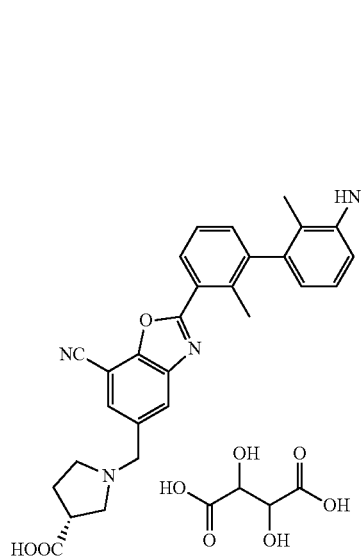
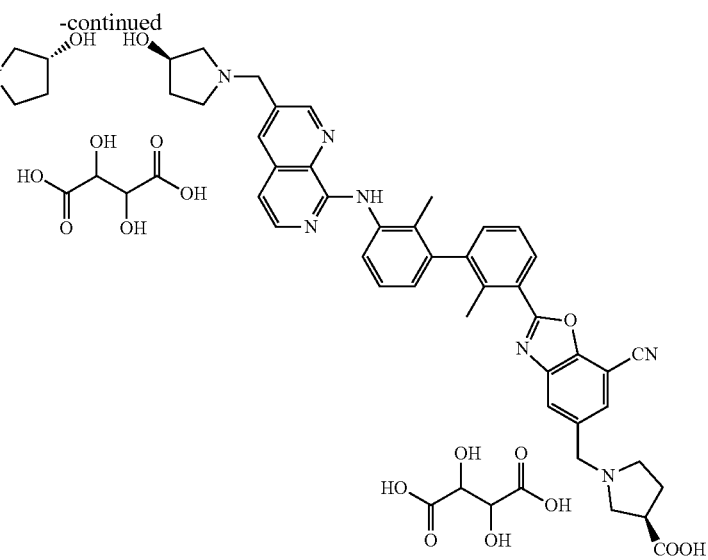

L-tartaric acid (31.52 mg, 0.210 mmol, 2.05 eq.) was added to a solution of Compound 1 (71.02 mg, 0.102 mmol) in tetrahydrofuran (2.0 mL). The reaction mixture was stirred for 30 min. to give a slurry. The slurry was stirred continuously for 2 hours, and then filtered to give a mother liquid and a solid. The solid was dried under vacuum at 40-41° C. overnight to provide Compound 1 L-tartaric acid salt (90.5 mg, 96% yield).

The stoichiometric ratio between Compound 1 and L-tartaric acid was 1:1.7 by $^1$H NMR (FIG. 14). Compound 1 L-tartaric acid salt was characterized by XRPD (FIG. 13). Analytical data collected on the product were obtained. The purity of the L-tartaric acid salt was determined by HPLC as 96.4%.

Example 12. Preparation of the Compound 1 Tri-Hydrochloric Acid Salt

Into a scintillation vial was charged Compound 1 (500 mg, 0.721 mmol) and dimethylsulfoxide (4.0 mL).

Into a 50 mL round bottom flask with stir bar was charged tetrahydrofuran (30.0 mL) and 4N hydrochloric acid/dioxane (721 uL, 4 eq.). With stirring the Compound 1 solution was added via pipetor to the tetrahydrofuran solution dropwise over 3 minutes. Solids precipitated out of solution, and the slurry was light yellow in color. The mixture was stoppered and stirred overnight at room temperature.

The slurry was filtered and the filter cake rinsed with tetrahydrofuran (10.0 mL). The resulting solid was dried under vacuum. 598 mg of salt was recovered. IPLC purity was 98.5085%. Chloride analysis gave 2.89 eq. of hydrochloric acid.

Example 13. Preparation of the Compound 1 Phosphoric Acid Salt (~1:3)

Into a 40 mL scintillation vial with stir bar was charged acetone (15.0 mL) and phosphoric acid (0.151 mL, 2.162 mmol, 3 eq.). The mixture was stirred to give a clear solution. In a 20 mL scintillation vial was charged Compound 1 (500 mg, 0.721 mmol), dichloromethane (4.50 mL) and methanol (0.50 mL). The mixture was agitated until homogeneous, then added dropwise to the phosphoric acid solution over 3-4 minutes. Yellow solids precipitated out of solution, and the mixture was stirred at room temperature for 90 minutes, then filtered. The filter cake was washed with acetone (5.00 mL), and the solids were dried under high vacuum.

722 mg of product was recovered. IPLC purity was 98.7%. Salt ratio was determined by acid-base titration for phosphoric acid content to be 1:2.78.

Example 14. Preparation of the Compound 1 Phosphoric Acid Salt (~1:2)

Into a 40 mL scintillation vial with stir bar was charged acetone (15.0 mL) and phosphoric acid (0.103 mL, 1.477 mmol, 2 eq.). The mixture was stirred to give a clear solution. In a 20 mL scintillation vial was charged Compound 1 (500 mg, 0.721 mmol), dichloromethane (4.50 mL) and methanol (0.50 mL). The mixture was agitated until homogeneous, then added dropwise to the phosphoric acid solution over 3-4 minutes. Yellow solids precipitated out of solution, and the mixture was stirred at room temperature for 90 minutes, then filtered. The filter cake was washed with acetone (5.00 mL), and the solids were dried under high vacuum.

640 mg of product was recovered. IPLC purity was 98.7%. Salt ratio was determined by acid-base titration for phosphoric acid content to be 1:2.29.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A salt, wherein the salt is (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid di-oxalic acid salt, and wherein the salt is crystalline.

2. The salt of claim 1, having an X-ray powder diffraction pattern as substantially shown in FIG. 10.

3. The salt of claim 1, having a DSC thermogram substantially as depicted in FIG. 11.

4. The salt of claim 1, having a thermogravimetric analysis (TGA) thermogram substantially as depicted in FIG. 12.

5. The salt of claim 1, having at least one X-ray powder diffraction (XRPD) peak selected from 7.0±0.2, 11.4±0.2, 13.2±0.2, 14.9±0.2, and 17.0±0.2 degrees 2-theta.

6. The salt of claim 1, having at least two X-ray powder diffraction (XRPD) peaks selected from 7.0±0.2, 11.4±0.2, 13.2±0.2, 14.9±0.2, and 17.0±0.2 degrees 2-theta.

7. The salt of claim 1, having at least three X-ray powder diffraction (XRPD) peaks selected from 7.0±0.2, 11.4±0.2, 13.2±0.2, 14.9±0.2, and 17.0±0.2 degrees 2-theta.

8. The salt of claim 1, having at least four X-ray powder diffraction (XRPD) peaks selected from 7.0±0.2, 11.4±0.2, 13.2±0.2, 14.9±0.2, and 17.0±0.2 degrees 2-theta.

9. The salt of claim 1, having characteristic X-ray powder diffraction (XRPD) peaks at 7.0±0.2, 11.4±0.2, 13.2±0.2, 14.9±0.2, and 17.0±0.2 degrees 2-theta.

10. The salt of claim 1, having a characteristic X-ray powder diffraction (XRPD) peak at 7.0±0.2 degrees 2-theta.

11. The salt of claim 1, having a characteristic X-ray powder diffraction (XRPD) peak at 11.4±0.2 degrees 2-theta.

12. The salt of claim 1, having a characteristic X-ray powder diffraction (XRPD) peak at 13.2±0.2 degrees 2-theta.

13. The salt of claim 1, having a characteristic X-ray powder diffraction (XRPD) peak at 14.9±0.2 degrees 2-theta.

14. The salt of claim 1, having a characteristic X-ray powder diffraction (XRPD) peak at 17.0±0.2 degrees 2-theta.

15. The salt of claim 1, having an endothermic peak at a temperature of 235±3° C. in a differential scanning calorimetry (DSC) thermogram.

16. A pharmaceutical composition comprising a salt of claim 1, and a pharmaceutically acceptable carrier or excipient.

17. A solid oral dosage form comprising the pharmaceutical composition of claim 16.

18. A method of inhibiting PD-1/PD-L1 interaction, said method comprising administering to a patient a salt of claim 1.

19. A method of treating a disease or disorder associated with inhibition of PD-1/PD-L1 interaction, said method comprising administering to a patient in need thereof a therapeutically effective amount of a salt of claim 1.

20. A method of enhancing, stimulating and/or increasing the immune response in a patient, said method comprising administering to the patient in need thereof a therapeutically effective amount of a salt of claim 1.

21. The method according to claim 19, wherein the disease or disorder is cancer or infection diseases.

22. The method according to claim 21, wherein the disease or disorder is cancer.

23. The method according to claim 22, wherein the cancer is selected from a metastatic cancer that expresses PD-L1, lung cancer, small cell lung cancer, non-small cell lung cancer, hepatic cancer, hepatocellular carcinoma, melanoma, cancer of the bladder, cancer of the urethra, renal cancer, renal clear cell carcinoma, and cutaneous squamous cell carcinoma.

* * * * *